US008889862B2

(12) United States Patent
Kumar et al.

(10) Patent No.: US 8,889,862 B2
(45) Date of Patent: Nov. 18, 2014

(54) 2-AMINO-4-ARYLTHIAZOLE COMPOUNDS AS TRPA1 ANTAGONISTS

(71) Applicant: Glenmark Pharmaceuticals, S.A., La Chaux-de-Fonds (CH)

(72) Inventors: Sukeerthi Kumar, Navi Mumbai (IN); Abraham Thomas, Navi Mumbai (IN); Sachin Sundarlal Chaudhari, Navi Mumbai (IN); Bipin Parsottam Kansagra, Ahmedabad (IN); Venkata Ramana Yemireddy, Navi Mumbai (IN); Neelima Khairatkar-Joshi, Thane (IN); Indranil Mukhopadhyay, Navi Mumbai (IN); Girish Gudi, Mumbai (IN)

(73) Assignee: Glenmark Pharmaceuticals, S.A., La Chaux-de-Fonds (CH)

( * ) Notice: Subject to any disclaimer, the term of this patent is extended or adjusted under 35 U.S.C. 154(b) by 0 days.

(21) Appl. No.: 14/058,509

(22) Filed: Oct. 21, 2013

(65) Prior Publication Data

US 2014/0045865 A1 Feb. 13, 2014

Related U.S. Application Data

(63) Continuation of application No. 13/327,128, filed on Dec. 15, 2011, now Pat. No. 8,592,398.

(60) Provisional application No. 61/428,327, filed on Dec. 30, 2010, provisional application No. 61/466,535, filed on Mar. 23, 2011, provisional application No. 61/495,002, filed on Jun. 9, 2011, provisional application No. 61/552,076, filed on Oct. 27, 2011.

(30) Foreign Application Priority Data

| Dec. 20, 2010 | (IN) | ................. 3451/MUM/2010 |
| Mar. 16, 2011 | (IN) | ................. 748/MUM/2011 |
| May 25, 2011 | (IN) | ................. 1569/MUM/2011 |
| Sep. 28, 2011 | (IN) | ................. 2741/MUM/2011 |

(51) Int. Cl.

| C07D 491/00 | (2006.01) |
| C07D 211/60 | (2006.01) |
| C07D 277/00 | (2006.01) |
| A61K 31/519 | (2006.01) |
| A61K 31/445 | (2006.01) |
| A61K 31/425 | (2006.01) |
| C07D 513/04 | (2006.01) |
| C07D 491/048 | (2006.01) |
| C07D 495/04 | (2006.01) |
| C07D 491/04 | (2006.01) |
| C07F 9/6561 | (2006.01) |
| C07D 487/04 | (2006.01) |

(52) U.S. Cl.
CPC ............ *C07F 9/6561* (2013.01); *C07D 513/04* (2013.01); *C07D 491/048* (2013.01); *C07D 495/04* (2013.01); *C07D 491/04* (2013.01); *C07F 9/65616* (2013.01); *C07D 487/04* (2013.01)
USPC ........... 544/278; 546/245; 548/184; 548/185; 514/260.1; 514/330; 514/371

(58) Field of Classification Search
USPC ............... 544/278; 546/245; 548/184, 185; 514/260.1, 330, 371
See application file for complete search history.

(56) References Cited

U.S. PATENT DOCUMENTS

| 7,662,977 | B2 | 2/2010 | Garlich et al. |
| 7,951,814 | B2 | 5/2011 | Muthuppalniappan et al. |
| 8,163,761 | B2 | 4/2012 | Ng et al. |
| 8,362,025 | B2 | 1/2013 | Ng et al. |

(Continued)

FOREIGN PATENT DOCUMENTS

| IN | 2512/MUM/2008 A | 8/2010 |
| WO | 2009/118596 A2 | 10/2009 |

(Continued)

OTHER PUBLICATIONS

Heimbach et al., "Absorption Rate Limit Considerations for Oral Phosphate Prodrugs", Pharmaceutical Research, Jun. 2003, pp. 848-856, vol. 20-issue No. 6, Plenum Publishing Corporation.

MacPherson et al., "Noxious compounds activate TRPA1 ion channels through covalent modification of cysteines", Letters, Feb. 1, 2007, pp. 541-545, vol. 445, Nature Publishing Group.

McMahon and Wood, "Increasingly Irritable and Close to Tears: TRPA1 in Inflammatory Pain", Cell, Mar. 24, 2006, pp. 1123-1125, vol. 124, Elsevier Inc.

(Continued)

*Primary Examiner* — Paul Zarek
*Assistant Examiner* — George W Kosturko
(74) *Attorney, Agent, or Firm* — Pergament Gilman & Cepeda LLP; Milagros A. Cepeda; Edward D. Pergament

(57) ABSTRACT

The present invention is related to 2-amino-4-arylthiazole derivatives as TRPA (Transient Receptor Potential subfamily A) modulators. In particular, compounds described herein are useful for treating or preventing diseases, conditions and/or disorders modulated by TRPA1 (Transient Receptor Potential subfamily A, member 1). Also provided herein are processes for preparing compounds described herein, intermediates used in their synthesis, pharmaceutical compositions thereof, and methods for treating or preventing diseases, conditions and/or disorders modulated by TRPA1.

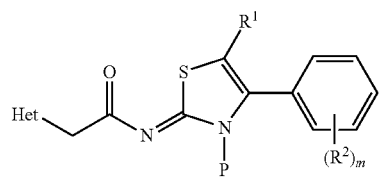

6 Claims, No Drawings

(56) References Cited

U.S. PATENT DOCUMENTS

| | | | |
|---|---|---|---|
| 8,507,503 | B2 | 8/2013 | Kumar et al. |
| 8,541,423 | B2 | 9/2013 | Moran et al. |
| 2012/0010223 | A1 | 1/2012 | Kumar et al. |
| 2012/0041004 | A1 | 2/2012 | Chaudhari et al. |
| 2012/0157411 | A1 | 6/2012 | Kumar et al. |
| 2012/0178766 | A1 | 7/2012 | Chaudhari et al. |

FOREIGN PATENT DOCUMENTS

| | | | |
|---|---|---|---|
| WO | 2009/144548 A1 | 12/2009 | |
| WO | 2009/158719 A2 | 12/2009 | |
| WO | 2010/109287 A1 | 9/2010 | |
| WO | WO 2010109329 A1 * | 9/2010 | |
| WO | WO 2010109334 A2 * | 9/2010 | |
| WO | 2010/125469 A1 | 11/2010 | |
| WO | 2010/132838 A1 | 11/2010 | |
| WO | 2011/114184 A1 | 9/2011 | |
| WO | 2011/132017 A1 | 10/2011 | |

OTHER PUBLICATIONS

Kathleen M. Foley, "Problems of Overarching Importance Which Transcend Organ Systems", Pain, Cecil Textbook of Medicine, 1996, pp. 100-107, vol. 1, 20th Edition, W.B. Saunders Company.

Story et al., "ANKTM1, a TRP-like Channel Expressed in Nociceptive Neurons, Is Activated by Cold Temperatures", Cell, Mar. 21, 2003, pp. 819-829, vol. 112, Cell Press.

Voorhoeve et al., "A Genetic Screen Implicates miRNA-372 and miRNA-373 As Oncogenes in Testicular Germ Cell Tumors", Cell, Mar. 24, 2006, pp. 1169-1181, vol. 124, Elsevier Inc.

Wissenbach et al.: "TRP channels as potential drug targets", Biology of the Cell, 2004, pp. 47-54, vol. 96, Elsevier SAS.

International Search Report and Written Opinion dated, Mar. 14, 2012 for corresponding International Patent Application No. PCT/IB2011/003224.

Iyer et al., "Synthesis of Iodoalkylacylates and Their Use in the preparation of S-Alkyl Phosphorothiolates", Synthetic Communications, 1995, pp. 2739-2749, vol. 25-issue No. 18, Marcel Dekker, Inc.

Harada et al., "A Simple Preparation of Chloromethyl Esters of the Blocked Amino Acids", Synthetic Communications, 1994, pp. 767-772, vol. 24-issue No. 6, Marcel Dekker, Inc.

Robinson et al., "Discovery of the Hemifumarate and (α-L-Alanyloxy)methyl Ether as Prodrugs of an Antirheumatic Oxindole: Prodrugs for the Enolic OH Group", J. Med. Chem., 1996, pp. 10-18, vol. 39-issue No. 1, American Chemical Society.

Sams et al., "Discovery of Phosphoric Acid Mono-{2-[(E/Z)-4-(3,3-dimethyl-butyrylamino)-3,5-difluoro-benzoylimino]-thiazol-3-ylmethyl} Ester (Lu AA47070): A Phosphonooxymethylene Prodrug of a Potent and Selective hA2A Receptor Antagonist", J. Med. Chem., 2011, pp. 751-764, vol. 54-issue No. 3, American Chemical Society.

Mantyla et al., "A novel synthetic route for the preparation of alkyl and benzyl chloromethyl phosphates", Tetrahedron Letters, 2002, pp. 3793-3794, vol. 43, Elsevier Science Ltd.

Goldwhite and Saunders, "Esters containing Phosphorus. Part XIV. Some tert.-Butyl Esters and Their Reactions", Journal of the Chemical Society, 1957, pp. 2409-2412.

Krise et al., "Novel Prodrug Approach for Tertiary Amines: Synthesis and Preliminary Evaluation of N-Phosphonooxymethyl Prodrugs", J. Med. Chem., 1999, pp. 3094-3100, vol. 42-issue No. 16, American Chemical Society.

Ettmayer et al., "Lessons Learned from Marketed and Investigational Prodrugs", Perspective, Journal of Medicinal Chemistry, May 6, 2004, pp. 2393-2404, vol. 47-issue No. 10, American Chemical Society.

Pauletti et al., "Improvement of oral peptide bioavailability: Peptidomimetics and prodrug strategies", Advanced Drug Delivery Reviews, 1997, pp. 235-256, vol. 27, Elsevier Science B.V.

John W. Clader, "The Discovery of Ezetimibe: A View from Outside the Receptor", Perspective, Journal of Medicinal Chemistry, Jan. 1, 2004, pp. 1-9, vol. 47-issue No. 1, American Chemical Society.

Toth et al., "Arachidonyl dopamine as a ligand for the vanilloid receptor VR1 of the rat", Life Sciences, 2003, pp. 487-498, vol. 73, Elsevier Science Inc.

McNamara et al., "TRPA1 mediates formalin-induced pain", PNAS, Aug. 14, 2007, pp. 13525-13530, vol. 104-issue No. 33.

Rautio et al., "Prodrugs: design and clinical applications", Nature Reviews, Drug Discovery, Mar. 2008, pp. 255-270, vol. 7, Nature Publishing Group.

Oslob et al., "Water-soluble prodrugs of an Aurora kinase inhibitor", Bioorganic & Medicinal Chemistry Letters, 2009, pp. 1409-1412, vol. 19, Elsevier Ltd.

First Office Action issued by the State Intellectual Property Office (SIPO) of P. R. China on Jun. 24, 2014, for corresponding Chinese Patent Application No. 201180059690.2.

International Search Report drawn up by the Examiner and forwarded with the Invitation to Respond issued on Jul. 3, 2014, by the Intellectual Property Office of Singapore, for corresponding Singapore Patent Application No. 201304607-3.

Written Opinion drawn up by the Examiner and forwarded with the Invitation to Respond issued on Jul. 3, 2014, by the Intellectual Property Office of Singapore, for corresponding Singapore Patent Application No. 201304607-3.

Non-Final Office Action mailed by the USPTO on Feb. 26, 2013, for U.S. Appl. No. 13/327,128.

* cited by examiner

2-AMINO-4-ARYLTHIAZOLE COMPOUNDS AS TRPA1 ANTAGONISTS

RELATED APPLICATIONS

This application is a Continuation Application of U.S. patent application Ser. No. 13/327,128, filed on Dec. 15, 2011, which claims priority to Indian provisional application Nos. 3451/MUM/2010 filed on Dec. 20, 2010; 748/MUM/2011 filed on Mar. 16, 2011; 1569/MUM/2011 filed on May 25, 2011; 2741/MUM/2011 filed on Sep. 28, 2011 and US provisional application Nos. 61/428,327 filed on Dec. 30, 2010; 61/466,535 filed on Mar. 23, 2011; 61/495,002 filed on Jun. 09, 2011; 61/552,076 filed on Oct. 27, 2011 all of which are hereby incorporated by reference in their entirety.

TECHNICAL FIELD

The present application relates to 2-amino-4-arylthiazole compounds, methods for their synthesis and their use as transient receptor potential ankyrin 1 (TRPA1) antagonists.

BACKGROUND OF THE INVENTION

The transient receptor potential (TRP) channels or receptors are increasingly recognized as transducers of pain signal in response to mechanical, thermal, inflammatory and chemical assaults. They have been classified into seven subfamilies: TRPC (canonical), TRPV (vanilloid), TRPM (melastatin), TRPP (polycystin), TRPML (mucolipin), TRPA (ankyrin, ANKTM1) and TRPN(NOMPC) families. The TRPC subfamily are the original members which were discovered and are homologous to the Drosophila trp-channel. Seven isoforms (TRPC1-TRPC7) have been characterized so far. Currently the TRPV family has 6 members. TRPVS and TRPV6 are more closely related to each other than to TRPV1, TRPV2, TRPV3 or TRPV4. TRPA1 is most closely related to TRPV3 and is more closely related to TRPV1 and TRPV2 than to TRPVS and TRPV6. The TRPM family has 8 members. Constituents include the following: the founding member TRPM1 (melastatin or LTRPC1), TRPM3 (KIAA1616 or LTRPC3), TRPM7 (TRP-PLIK, ChaK(1), LTRPC7), TRPM6 (ChaK2), TRPM2 (TRPC7 or LTRPC2), TRPM8 (TRP-p8 or CMR1), TRPMS (MTR1 or LTRPCS) and TRPM4 (FLJ20041 or LTRPC4). The TRPML family consists of the mucolipins, which include TRPML1 (mucolipin 1), TRPML2 (mucolipin 2) and TRPML3 (mucolipin 3). The TRPP family consists of two groups of channels: those predicted to have six transmembrane domains such as TRPP2 (PKD2), TRPP3 (PKD2L1), TRPPS (PKD2L2) and those that have eleven domains such as TRPP1 (PKD1, PC1), PKD-REJ and PKD-1L1. The sole mammalian member of the TRPA family is ANKTM1.

It is believed TRPA1 is expressed in nociceptive neurons. Nociceptive neurons of the nervous system sense the peripheral damage and transmit pain signals. TRPA1 is membrane bound and most likely acts as a heterodimeric voltage gated channel. It is believed to have a particular secondary structure, its N-terminus is lined with a large number of ankyrin repeats which are believed to form a spring-like edifice. TRPA1 is activated by a variety of noxious stimuli, including cold temperatures (activated at 17° C. and below), pungent natural compounds (e.g., mustard, cinnamon and garlic) and environmental irritants (MacPherson L J et al, Nature, 2007, 445; 541-545). Noxious compounds activate TRPA1 ion channels through covalent modification of cysteines to form covalently linked adducts. Variety of endogenous molecules produced during inflammation/tissue injury or allergy have been identified as pathological activators of TRPA1 receptor. These include hydrogen peroxide which is produced due to oxidative stress generated during inflammation, alkenyl aldehyde 4-HNE—an intracellular lipid peroxidation product and cyclopentenone prostaglandin 15dPGJ2 which is produced from PGD2 during inflammation/allergic response. TRPA1 is also activated in receptor dependant fashion by Bradykinin (BK) which is released during tissue injury at peripheral terminals.

The difference between TRPA1 and other TRP receptors is that TRPA1 ligand binding persists for hours due to which the physiological response (e.g., pain) is greatly prolonged. Hence to dissociate the electrophile, an effective antagonist is required.

In efforts to discover better analgesics for the treatment of both acute and chronic pain and to develop treatments for various neuropathic and nociceptive pain states, there exists a need for a more effective and safe therapeutic treatment of diseases, conditions and/or disorders modulated by TRPA1.

International publications WO2010109287, WO2010109328, WO2010109329 and WO2010109334, WO2009118596, WO2009144548, WO2010004390, IN200802512, WO2010125469, WO2011114184, WO2011132017, WO2007073505, WO2010075353, WO2009158719, WO2009002933 and WO2010132838 disclose various 2-amino-4-arylthiazole compounds which are useful for treating disorders related to TRPA1.

It has been found that a few of the 2-amino-4-arylthiazoles compounds having high TRPA1 activity are characterized by low aqueous solubility which may contribute to poor pharmacokinetic properties. Therefore it is important to find ways to improve the solubility and pharmacokinetic profile of these compounds.

Therefore it is an object of the present application to provide 2-amino-4-arylthiazole compounds having improved solubility and/or pharmacokinetic properties.

SUMMARY OF THE INVENTION

The present application provides compounds of 2-amino-4-arylthiazole which are useful for treating disorders mediated by TRPA1.

The present application relates to compound of formula (I):

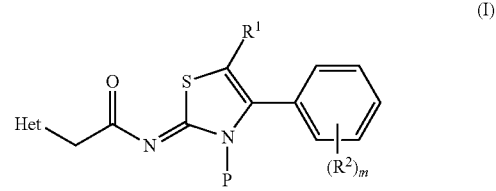

or a pharmaceutically acceptable salt thereof,
wherein,
Het is selected from the group consisting of

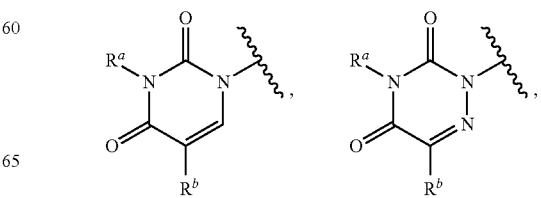

-continued
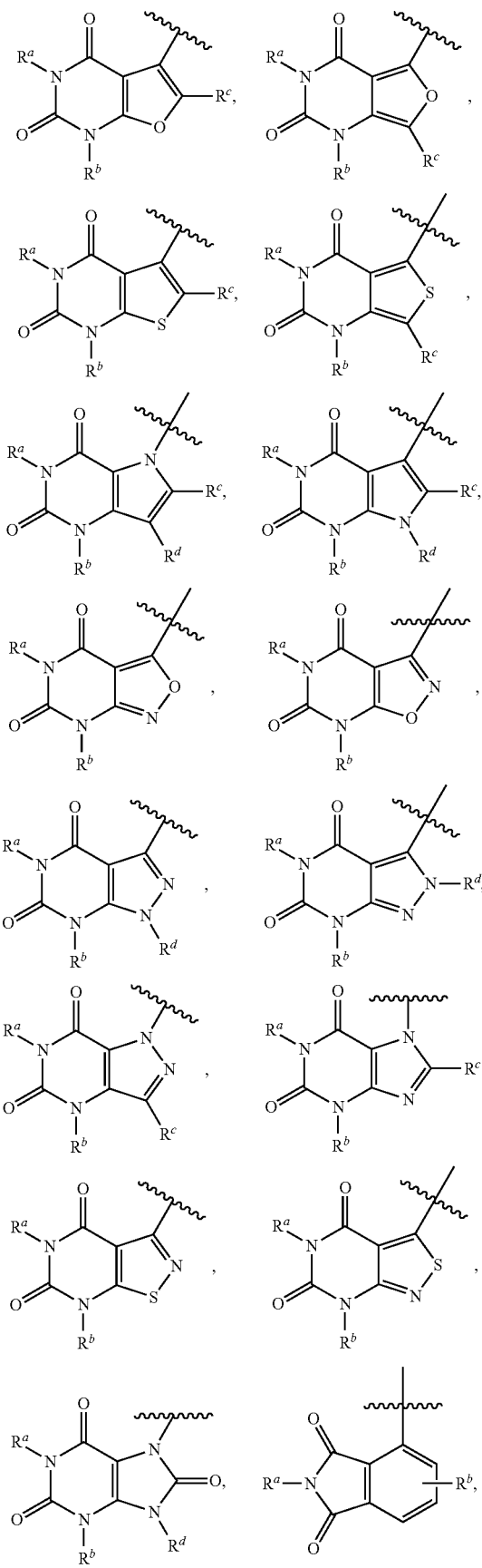
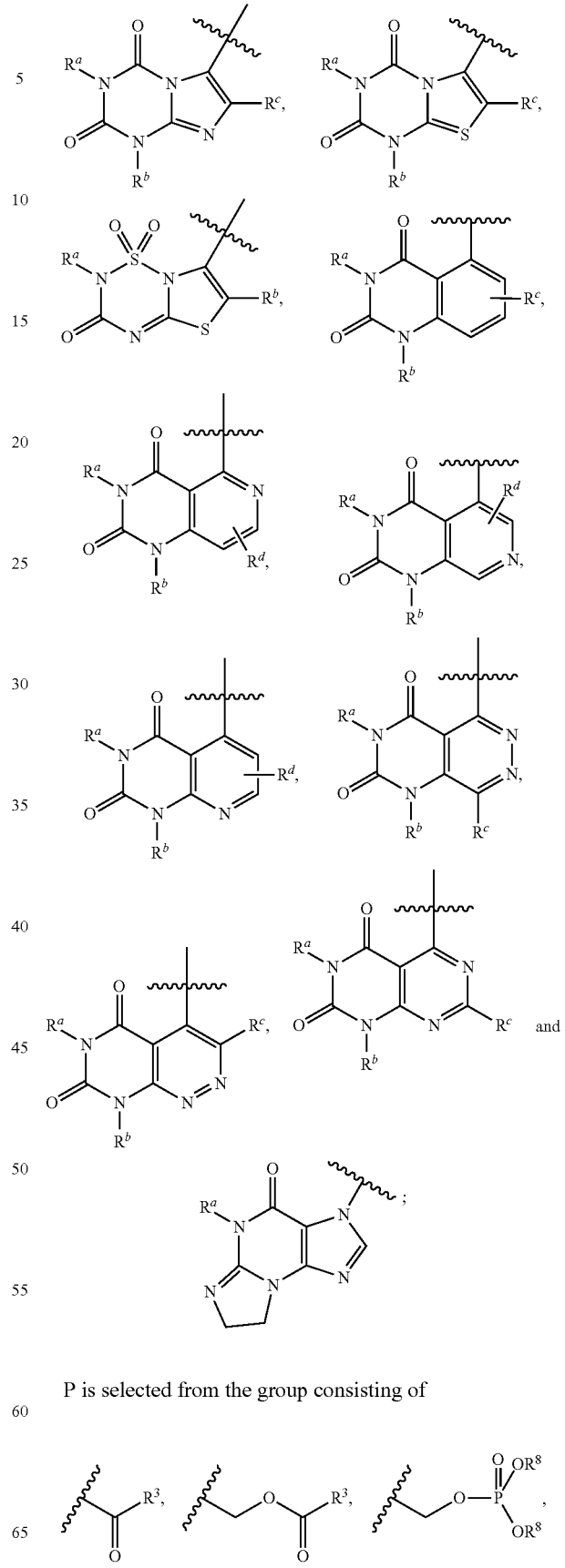
P is selected from the group consisting of

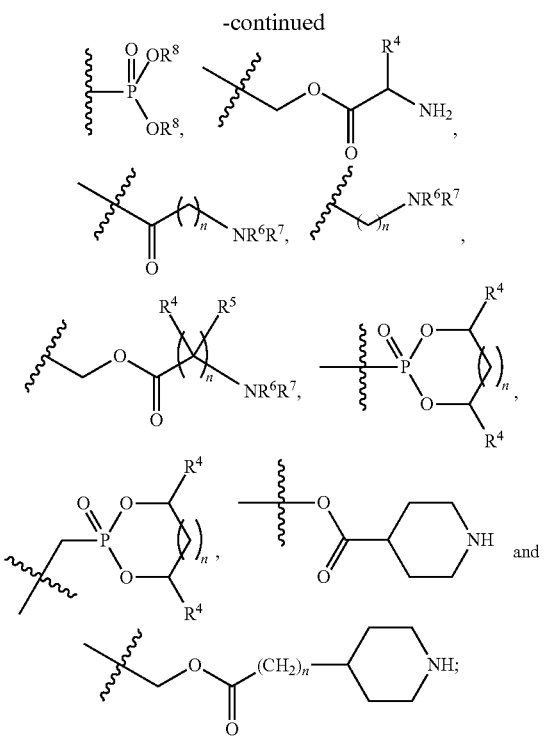

R$^1$ is selected from hydrogen, halogen, cyano, hydroxyl, substituted or unsubstituted alkyl, alkoxy, haloalkyl, haloalkoxy, cycloalkyl, cycloalkylalkyl, aryl, arylalkyl, heteroaryl, heteroarylalkyl, heterocyclic ring and heterocyclylalkyl;

at each occurrence, R$^2$, which may be the same or different, is independently selected from halogen, cyano, hydroxyl, nitro, —NR$^e$R$^f$, substituted or unsubstituted alkyl, alkoxy, haloalkyl, haloalkoxy, cycloalkyl, cycloalkylalkyl, aryl, arylalkyl, heteroaryl, heteroarylalkyl, heterocyclic ring and heterocyclylalkyl;

R$^3$ is selected from —NR$^6$R$^7$, substituted or unsubstituted alkyl, aryl, heterocyclic ring, heterocyclylalkyl and heteroaryl; R$^3$ or the group —OC(=O)R$^3$ is selected from amino acids such as isoleucinate, leucinate, lysinate, methioninate, phenylalaninate, threoninate, tryptophanate, valinate, alaninate, asparaginate, aspartic acetate, cysteinate, glutamic acetate, glutaminate, glycinate, prolinate, selenocysteinate, serinate, tyrosinate, argininate, histidinate, ornithinate or taurinate.

R$^4$ and R$^5$, which may be the same or different, are independently selected from hydrogen, substituted or unsubstituted alkyl, hydroxyalkyl, arylalkyl, heterocyclylalkyl, heteroarylalkyl, —(CR$^g$R$^h$)$_p$—C(O)—C$_1$-C$_4$alkyl, —(CR$^g$R$^h$)$_p$—C(O)—NR$^e$R$^f$, —(CR$^g$R$^h$)$_p$—NR$^e$R$^f$, —(CR$^g$R$^h$)$_p$—NR$^e$—C(O)—NR$^e$R$^f$ and —(CR$^g$R$^h$)$_p$—NR$^e$—C(=NH)—NR$^e$R$^f$;

R$^6$ and R$^7$, which may be the same or different, are independently selected from hydrogen, substituted or unsubstituted alkyl and hydroxyalkyl; or R$^6$ and R$^7$ together with the nitrogen atom to which they are attached, form a cyclic ring, which may be monocyclic, bicyclic or tricyclic rings, which is substituted or unsubstituted and wherein the cyclic ring optionally contains one or more heteroatoms selected from O, N or S;

R$^8$ is selected from hydrogen, C$_1$-C$_4$alkyl, arylalkyl and pharmaceutically acceptable cation (M$^+$ or M$^{2+}$);

R$^a$, R$^b$ and R$^d$, which may be the same or different, are each independently selected from hydrogen, trifluoromethyl, difluoromethyl, 2,2,2-trifluoroethyl and C$_1$-C$_4$alkyl;

R$^c$ is selected from hydrogen, halogen, trifluoromethyl, difluoromethyl, 2,2,2-trifluoroethyl and C$_1$-C$_4$alkyl;

R$^e$ and R$^f$, which may be the same or different, are independently selected from hydrogen, substituted or unsubstituted alkyl and hydroxyalkyl; or R$^e$ and R$^f$ together with the nitrogen atom to which they are attached, form a cyclic ring, which may be monocyclic, bicyclic or tricyclic rings, which is substituted or unsubstituted and wherein the cyclic ring optionally contains one or more heteroatoms selected from O, N or S;

R$^g$ and R$^h$, which may be the same or different, are each independently hydrogen or C$_1$-C$_4$ alkyl;

'm' is an integer ranging from 0 to 5, both inclusive;

'n' is an integer ranging from 1 to 4, both inclusive; and

'p' is an integer ranging from 1 to 3, both inclusive.

The compounds of formula (I) may involve one or more embodiments. Embodiments of formula (I) include compounds of formula (Ia), compounds of formula (Ib) and compounds of formula (Ic) as described hereinafter. It is to be understood that the embodiments below are illustrative of the present invention and are not intended to limit the claims to the specific embodiments exemplified. It is also to be understood that the embodiments defined herein may be used independently or in conjunction with any definition, claim or any other embodiment defined herein. Thus the invention contemplates all possible combinations and permutations of the various independently described embodiments. For example, the invention provides compounds of formula (I) as defined above wherein R$^1$ is hydrogen (according to an embodiment defined below) and R$^2$ is halogen (e.g. fluorine, chlorine), haloalkyl (e.g. trifluoromethyl) or haloalkoxy (e.g. trifluoromethoxy) (according to another embodiment defined below).

According to one embodiment, specifically provided are compounds of the formula (I) in which R$^1$ is hydrogen.

According to another embodiment, specifically provided are compounds of the formula (I) in which Het is selected from

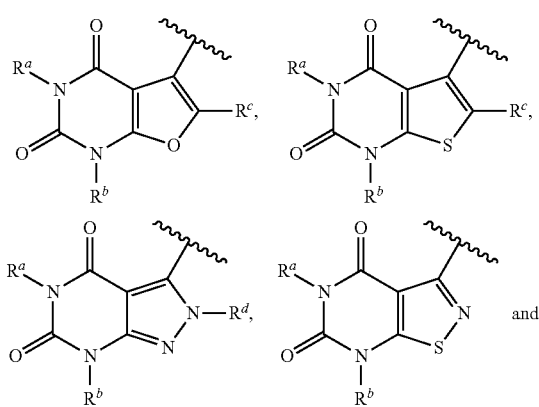

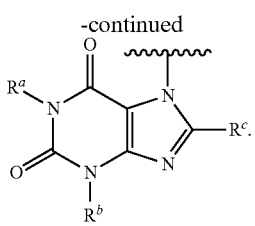

In this embodiment, $R^a$, and $R^b$ are independently selected from $C_1$-$C_4$alkyl (e.g. methyl, ethyl), trifluoromethyl, difluoromethyl, 2,2,2-trifluoroethyl and hydrogen; $R^c$ is independently selected from $C_1$-$C_4$alkyl (e.g. methyl, ethyl), trifluoromethyl, difluoromethyl, 2,2,2-trifluoroethyl, hydrogen and halogen.

According to another embodiment, specifically provided are compounds of the formula (I) in which Het is selected from

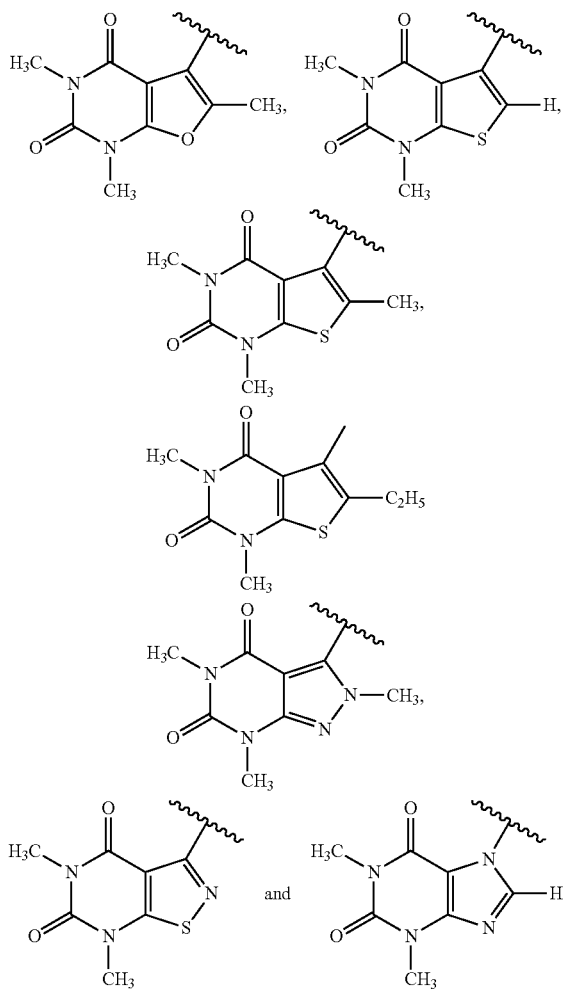

According to yet another embodiment, specifically provided are compounds of the formula (I) in which $R^2$ is selected from halogen (e.g. fluorine, chlorine), haloalkyl (e.g. trifluoromethyl) and haloalkoxy (e.g. trifluoromethoxy).

According to yet another embodiment, specifically provided are compounds of the formula (I) in which 'm' is 1, 2 or 3.

According to yet another embodiment, specifically provided are compounds of the formula (I) in which $R^2$ is fluorine (—F), chlorine (—Cl), trifluoromethyl (—$CF_3$) or trifluoromethoxy (—$OCF_3$); and 'm' is 2 or 3.

According to another embodiment, specifically provided are compounds of the formula (I) in which P is selected from

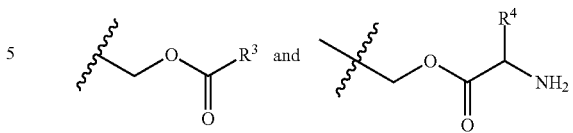

In this embodiment, $R^3$ is selected from hydrogen, substituted or unsubstituted alkyl (e.g methyl, isopropyl, isobutyl), arylalkyl (e.g benzyl), amino acid and heterocyclic ring (e.g. piperidinyl, pyrrolidinyl); or the group —OC(=O)$R^3$ is glycinate, L-alaninate, L-valinate, L-isoleucinate, L-prolinate, L-valinate or L-phenylalaninate; $R^4$ is selected from hydrogen, substituted or unsubstituted alkyl (e.g methyl, isopropyl, isobutyl), and arylalkyl (e.g benzyl).

According to another embodiment, specifically provided are compounds of the formula (I) in which P is selected from

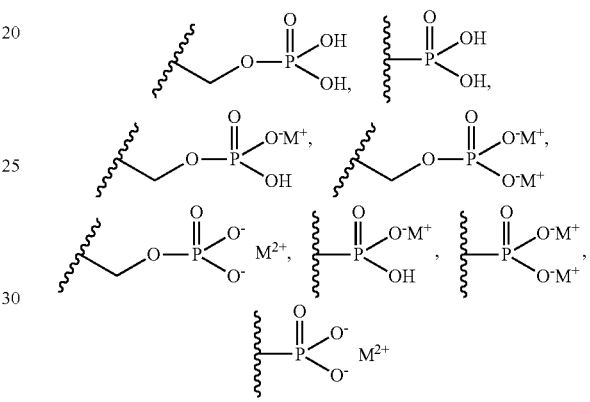

In this embodiment, $M^+$ is pharmaceutically acceptable cation comprising sodium, potassium, and ammonium; $M^{2+}$ is pharmaceutically acceptable cation comprising calcium, and magnesium.

Further embodiments relating to Het, P, m, $R^1$ and $R^2$ (and groups defined therein) are described hereinafter in relation to the compounds of formula (Ia), (Ib) and (Ic). It is to be understood that these embodiments are not limited to use in conjunction with formula (Ia), (Ib) or (Ic) but apply independently and individually to the compounds of formula (I). For example, in an embodiment described hereinafter, the invention specifically provides compounds of formula (Ia) in which $R^1$ is hydrogen, and consequently there is also provided a compound of formula (I) wherein $R^1$ is hydrogen.

The present invention also provides a compound of formula (Ia) which is an embodiment of a compound of formula (I).

Accordingly, the present invention provides the compound of formula (Ia):

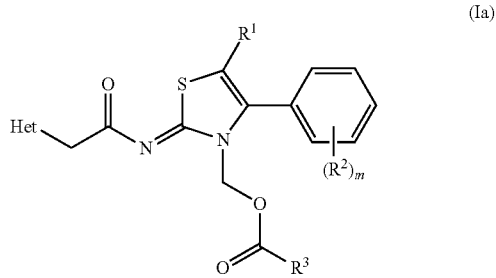

or a pharmaceutically acceptable salt thereof, wherein,
Het is selected from the group consisting of

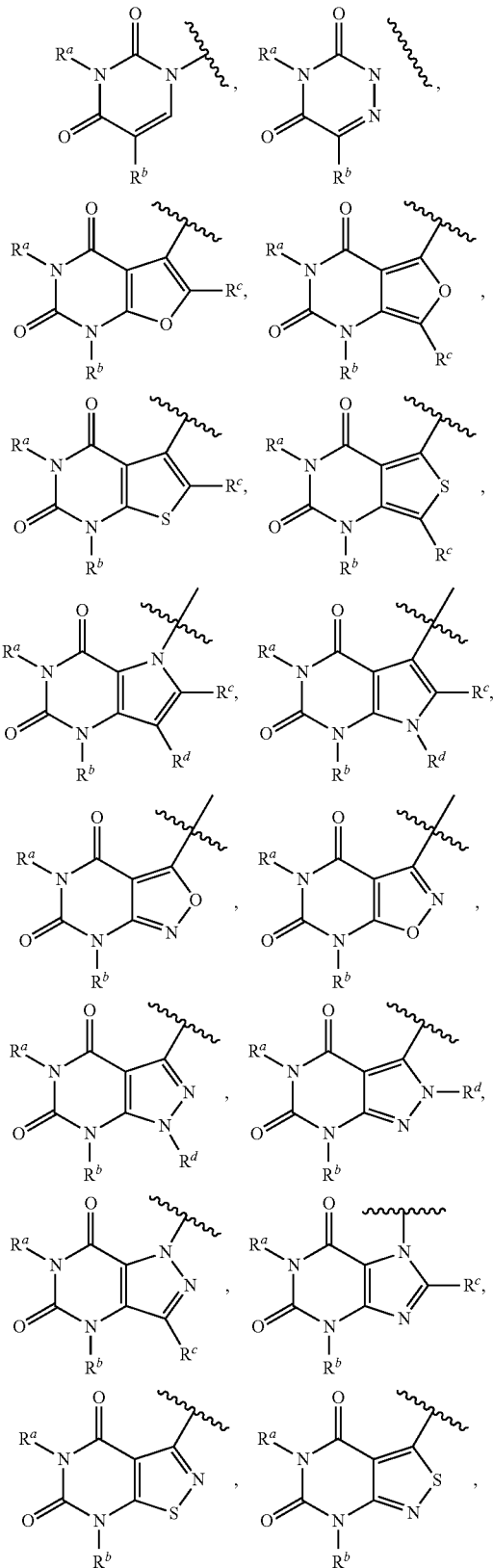
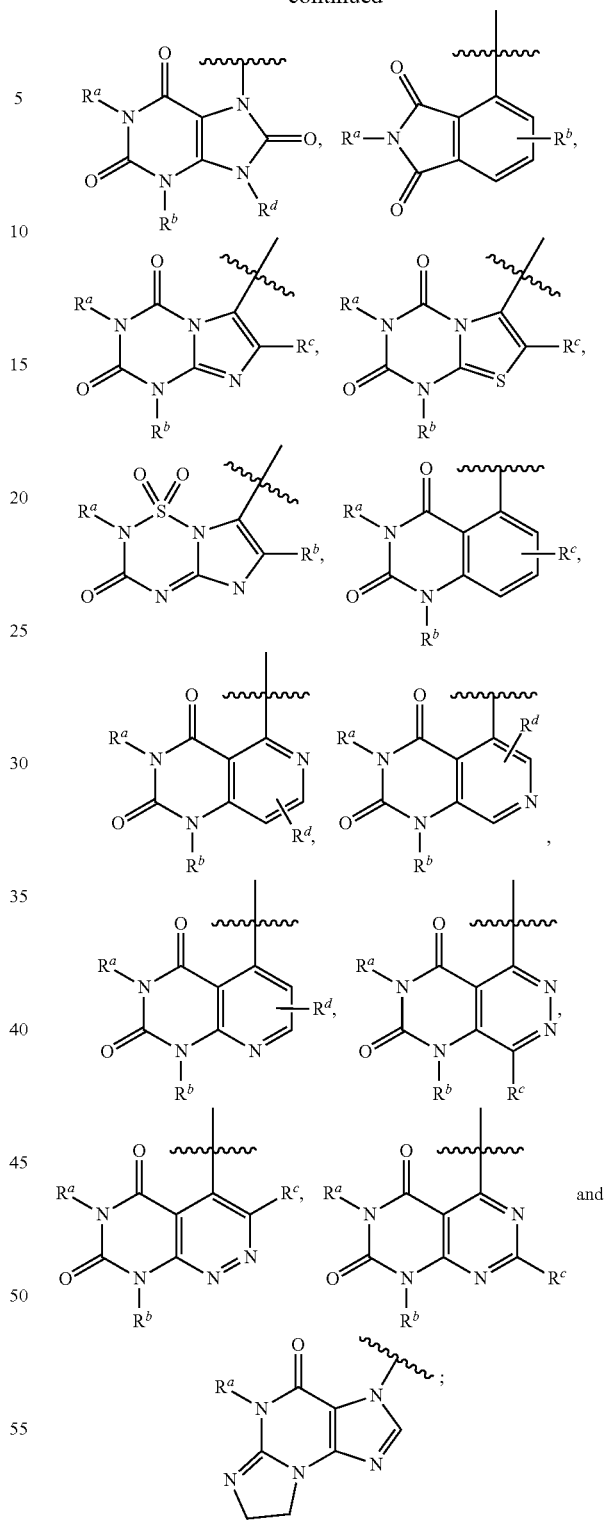

R[1] is selected from hydrogen, halogen, cyano, hydroxyl, substituted or unsubstituted alkyl, alkoxy, haloalkyl, haloalkoxy, cycloalkyl, cycloalkylalkyl, aryl, arylalkyl, heteroaryl, heteroarylalkyl, heterocyclic ring and heterocyclylalkyl;

at each occurrence, R[2], which may be the same or different, is independently selected from halogen, cyano, hydroxyl, nitro, —NR$^e$R$^f$, substituted or unsubstituted alkyl, alkoxy, haloalkyl, haloalkoxy, cycloalkyl, cycloalkylalkyl, aryl, arylalkyl, heteroaryl, heteroarylalkyl, heterocyclic ring and heterocyclylalkyl;

R$^3$ is selected from —NR$^6$R$^7$, substituted or unsubstituted alkyl, aryl, heterocyclic ring, heterocyclylalkyl and heteroaryl; R$^3$ or the group —OC(=O)R$^3$ is selected from amino acids such as isoleucinate, leucinate, lysinate, methioninate, phenylalaninate, threoninate, tryptophanate, valinate, alaninate, asparaginate, aspartic acetate, cysteinate, glutamic acetate, glutaminate, glycinate, prolinate, selenocysteinate, serinate, tyrosinate, argininate, histidinate, ornithinate or taurinate.

R$^6$ and R$^7$, which may be the same or different, are independently selected from hydrogen, substituted or unsubstituted alkyl and hydroxyalkyl; or R$^6$ and R$^7$ together with the nitrogen atom to which they are attached, form a cyclic ring, which may be monocyclic, bicyclic or tricyclic rings, which is substituted or unsubstituted and wherein the cyclic ring optionally contains one or more heteroatoms selected from O, N or S;

R$^a$, R$^b$ and R$^d$, which may be the same or different, are each independently selected from hydrogen, trifluoromethyl, difluoromethyl, 2,2,2-trifluoroethyl and C$_1$-C$_4$alkyl;

R$^c$ is selected from hydrogen, halogen, trifluoromethyl, difluoromethyl, 2,2,2-trifluoroethyl and C$_1$-C$_4$alkyl;

R$^e$ and R$^f$, which may be the same or different, are independently selected from hydrogen, substituted or unsubstituted alkyl and hydroxyalkyl; or R$^e$ and R$^f$ together with the nitrogen atom to which they are attached, form a cyclic ring, which may be monocyclic, bicyclic or tricyclic rings, which is substituted or unsubstituted and wherein the cyclic ring optionally contains one or more heteroatoms selected from O, N or S;

'm' is an integer ranging from 0 to 5, both inclusive.

The compounds of formula (Ia) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, claim or any other embodiment defined herein. Thus the invention contemplates all possible combinations and permutations of the various independently described embodiments. For example, the invention provides compounds of formula (Ia) as defined above wherein R$^1$ is hydrogen (according to an embodiment defined below) and R$^2$ is halogen (e.g. fluorine, chlorine), haloalkyl (e.g. trifluoromethyl) or haloalkoxy (e.g. trifluoromethoxy) (according to an embodiment defined below).

According to one embodiment, specifically provided are compounds of the formula (Ia) in which R$^1$ is hydrogen.

According to another embodiment, specifically provided are compounds of the formula (Ia) in which Het is selected from

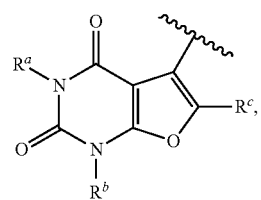

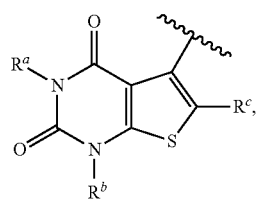

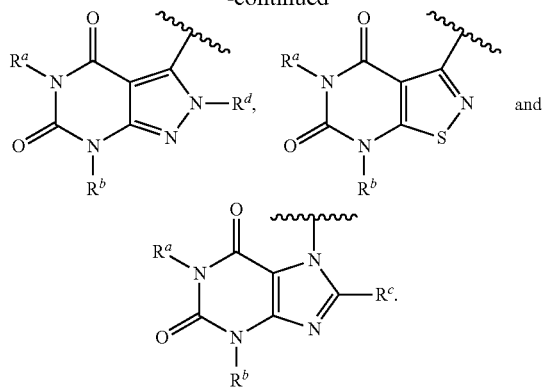

In this embodiment, R$^a$, and R$^b$ are independently selected from C$_1$-C$_4$alkyl (e.g. methyl, ethyl), trifluoromethyl, difluoromethyl, 2,2,2-trifluoroethyl and hydrogen; R$^c$ is selected from C$_1$-C$_4$alkyl (e.g. methyl, ethyl), trifluoromethyl, difluoromethyl, 2,2,2-trifluoroethyl, hydrogen and halogen.

According to yet another embodiment, specifically provided are compounds of the formula (Ia) in which Het is selected from

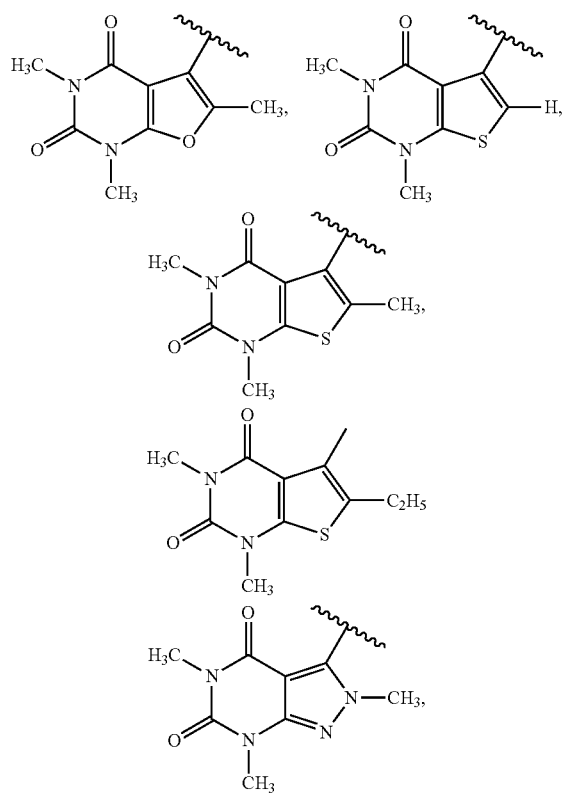

According to yet another embodiment, specifically provided are compounds of the formula (Ia) in which R$^2$ is selected from halogen (e.g. fluorine, chlorine), haloalkyl (e.g. trifluoromethyl) and haloalkoxy (e.g. trifluoromethoxy).

According to yet another embodiment, specifically provided are compounds of the formula (Ia) in which 'm' is 1, 2 or 3.

According to yet another embodiment, specifically provided are compounds of the formula (Ia) in which $R^2$ is fluorine (—F), chlorine (—Cl), trifluoromethyl (—$CF_3$) or trifluoromethoxy (—$OCF_3$); and 'm' is 2 or 3.

According to another embodiment, specifically provided are compounds of the formula (Ia) in which $R^3$ is substituted or unsubstituted alkyl, preferably substituted or unsubstituted $C_1$-$C_4$alkyl (e.g. isopropyl, tert-butyl, n-butyl).

According to yet another embodiment, specifically provided are compounds of the formula (Ia) in which $R^3$ is heterocyclic ring, preferably

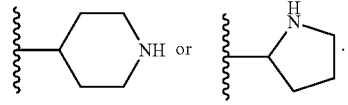

Below are representative compounds, which are illustrative in nature only and are not intended to limit the scope of the invention.

[2-{[(1,3-Dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methyl-2-methyl propanoate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl-2-methylpropanoate;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl 2,2-dimethylpropanoate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl L-prolinate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl L-prolinate hydrochloride;

[2-{[(1,3-Dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methylpiperidine-4-carboxylate;

[2-{[(1,3-Dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methylpiperidine-4-carboxylate hydrochloride;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl piperidine-4-carboxylate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl piperidine-4-carboxylate hydrochloride;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl piperidine-4-carboxylate;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl piperidine-4-carboxylate hydrochloride;

The invention also provides a compound of formula (Ib) which is an embodiment of a compound of formula (I).

Accordingly the present invention provides the compound of formula (Ib):

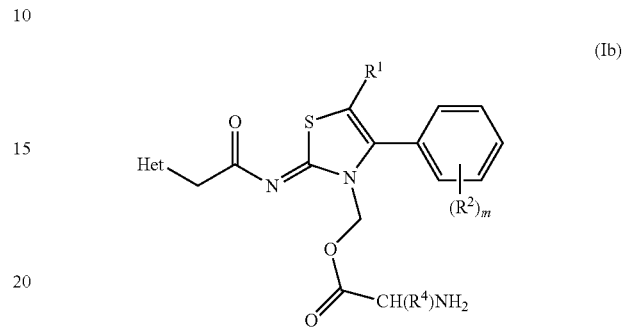

or a pharmaceutically acceptable salt thereof,
wherein,
Het is selected from the group consisting of

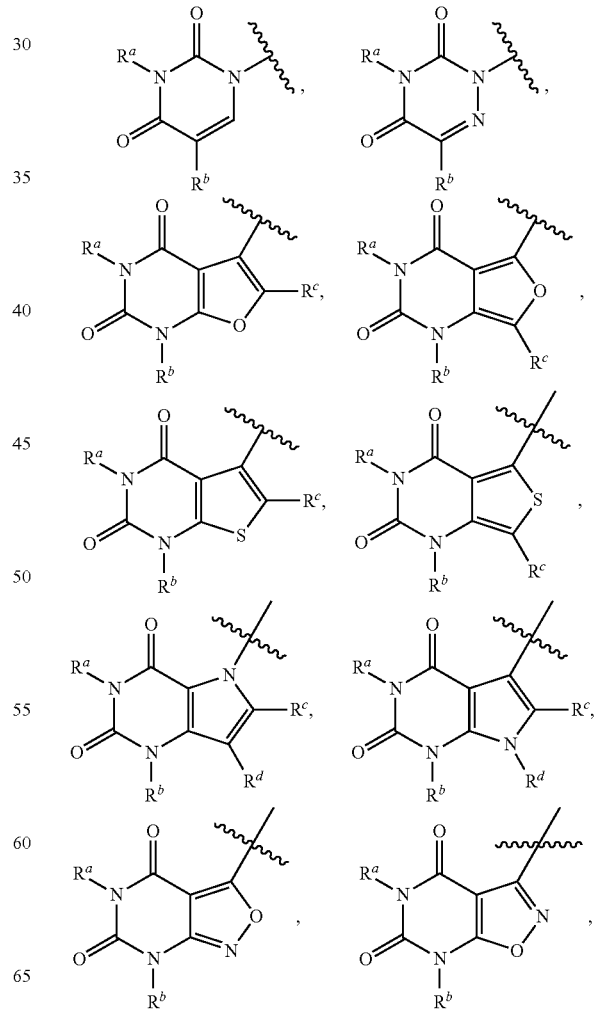

-continued

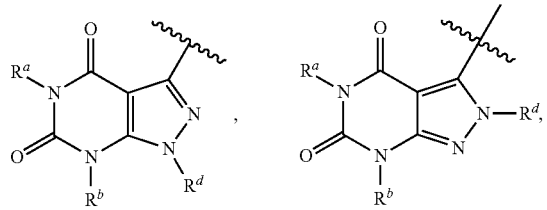

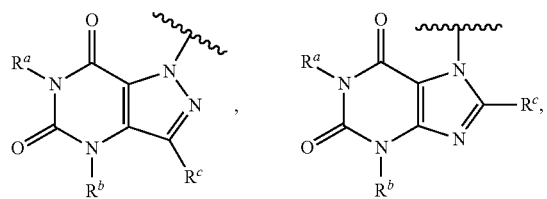

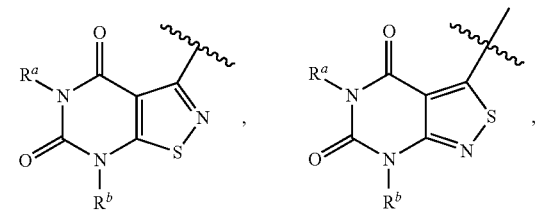

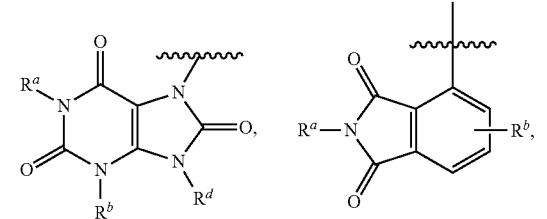

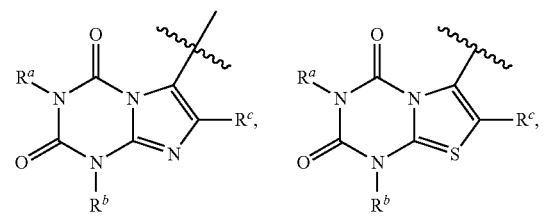

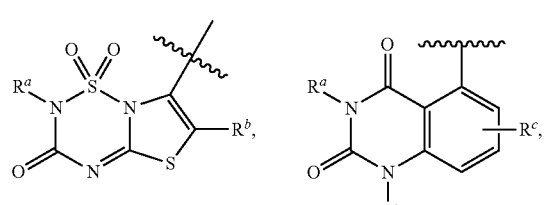

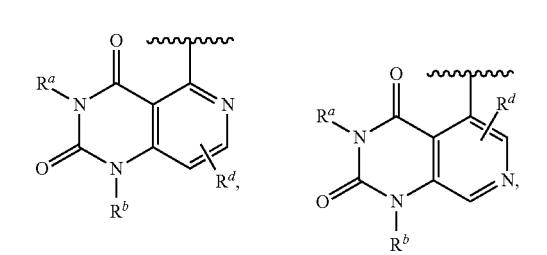

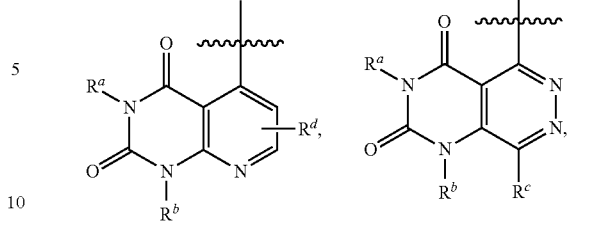

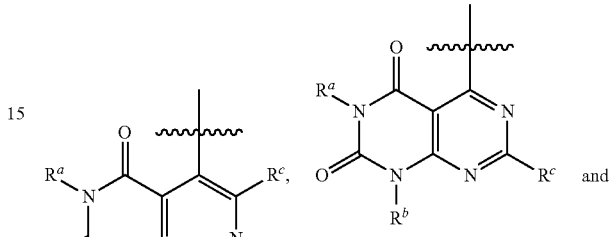

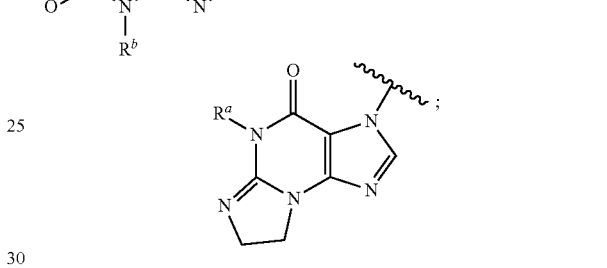

$R^1$ is selected from hydrogen, halogen, cyano, hydroxyl, substituted or unsubstituted alkyl, alkoxy, haloalkyl, haloalkoxy, cycloalkyl, cycloalkylalkyl, aryl, arylalkyl, heteroaryl, heteroarylalkyl, heterocyclic ring and heterocyclylalkyl;

at each occurrence, $R^2$, which may be the same or different, is independently selected from halogen, cyano, hydroxyl, nitro, —$NR^eR^f$, substituted or unsubstituted alkyl, alkoxy, haloalkyl, haloalkoxy, cycloalkyl, cycloalkylalkyl, aryl, arylalkyl, heteroaryl, heteroarylalkyl, heterocyclic ring and heterocyclylalkyl;

$R^4$ is selected from hydrogen, substituted or unsubstituted alkyl, hydroxyalkyl, arylalkyl, heterocyclylalkyl, heteroarylalkyl, —$(CR^gR^h)_p$—C(O)—$C_1$-$C_4$alkyl, —$(CR^gR^h)_p$—C(O)—$NR^eR^f$, —$(CR^gR^h)_p$—$NR^eR^f$, —$(CR^gR^h)_p$—$NR^e$—C(O)—$NR^eR^f$ and —$(CR^gR^h)_p$—$NR^e$—C(=NH)—$NR^eR^f$;

$R^a$, $R^b$ and $R^d$, which may be the same or different, are each independently selected from hydrogen, trifluoromethyl, difluoromethyl, 2,2,2-trifluoroethyl and $C_1$-$C_4$alkyl;

$R^c$ is selected from hydrogen, halogen, trifluoromethyl, difluoromethyl, 2,2,2-trifluoroethyl and $C_1$-$C_4$alkyl;

$R^e$ and $R^f$, which may be the same or different, are independently selected from hydrogen, substituted or unsubstituted alkyl and hydroxyalkyl; or $R^e$ and $R^f$ together with the nitrogen atom to which they are attached, form a cyclic ring, which may be monocyclic, bicyclic or tricyclic rings, which is substituted or unsubstituted and wherein the cyclic ring optionally contains one or more heteroatoms selected from O, N or S;

$R^g$ and $R^h$, which may be the same or different, are each independently hydrogen or $C_1$-$C_4$ alkyl;

'm' is an integer ranging from 0 to 5, both inclusive; and

'p' is an integer ranging from 1 to 3, both inclusive.

The compounds of formula (Ib) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, claim or any other embodiment defined herein. Thus the invention contemplates all possible combinations and permutations of the various independently described embodiments. For example, the invention provides compounds of formula (Ib) as defined above wherein $R^1$ is hydrogen (according to an embodiment defined below) and $R^2$ is halogen (e.g. fluorine, chlorine), haloalkyl (e.g. trifluoromethyl) or haloalkoxy (e.g. trifluoromethoxy) (according to an embodiment defined below).

According to one embodiment, specifically provided are compounds of the formula (Ib) in which $R^1$ is hydrogen.

According to another embodiment, specifically provided are compounds of the formula (Ib) in which Het is selected from

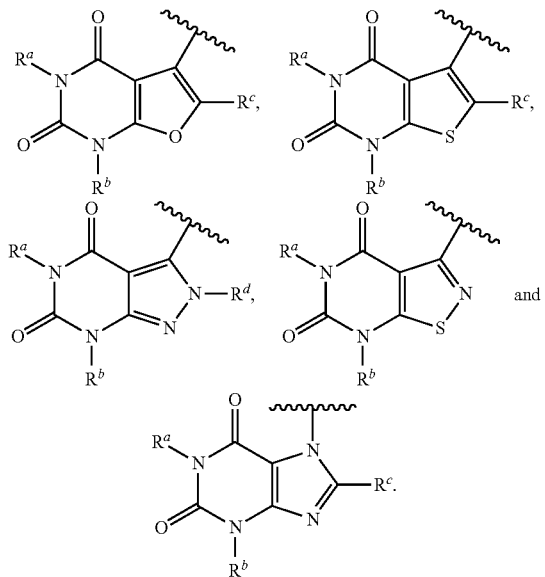

In this embodiment $R^a$, and $R^b$ are independently selected from $C_1$-$C_4$alkyl (e.g. methyl, ethyl), trifluoromethyl, difluoromethyl, 2,2,2-trifluoroethyl and hydrogen; $R^c$ is independently selected from $C_1$-$C_4$alkyl (e.g. methyl, ethyl), hydrogen and halogen.

According to yet another embodiment, specifically provided are compounds of the formula (Ib) in which Het is selected from

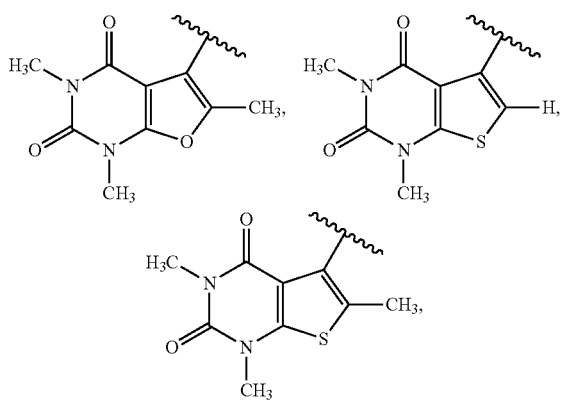

According to yet another embodiment, specifically provided are compounds of the formula (Ib) in which $R^2$ is independently selected from halogen (e.g. fluorine, chlorine), haloalkyl (e.g. trifluoromethyl) and haloalkoxy (e.g. trifluoromethoxy).

According to yet another embodiment, specifically provided are compounds of the formula (Ib) in which 'm' is 1, 2 or 3.

According to yet another embodiment, specifically provided are compounds of the formula (Ib) in which $R^2$ is fluorine (—F), chlorine (—Cl), trifluoromethyl (—$CF_3$) or trifluoromethoxy (—$OCF_3$); and 'm' is 2 or 3.

According to one embodiment, specifically provided are compounds of the formula (Ib) in which $R^4$ is independently selected from hydrogen, substituted or unsubstituted alkyl, preferably substituted or unsubstituted $C_1$-$C_4$alkyl (e.g. methyl, isopropyl, isobutyl), and arylalkyl (e.g. benzyl).

According to yet another embodiment, specifically provided are compounds of the formula (Ib) wherein the pharmaceutically acceptable salt is hydrochloride salt.

According to another embodiment, specifically provided are compounds of the following formula:

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl glycinate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl glycinate hydrochloride;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl L-alaninate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl L-alaninate hydrochloride;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl L-valinate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl L-valinate hydrochloride;

[2-{[(1,3-Dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3 (2H)-yl]methyl L-isoleucinate;

[2-{[(1,3-Dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3 (2H)-yl]methyl L-isoleucinate hydrochloride;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl L-isoleucinate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl L-isoleucinate hydrochloride;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl glycinate;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl glycinate hydrochloride;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl L-valinate;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl L-valinate hydrochloride;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl L-isoleucinate;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl L-isoleucinate hydrochloride;

4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl L-phenylalaninate;

4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl L-phenylalaninate hydrochloride.

The invention also provides a compound of formula (Ic) which is an embodiment of a compound of formula (I).

Accordingly, the present invention provides compound of formula (Ic):

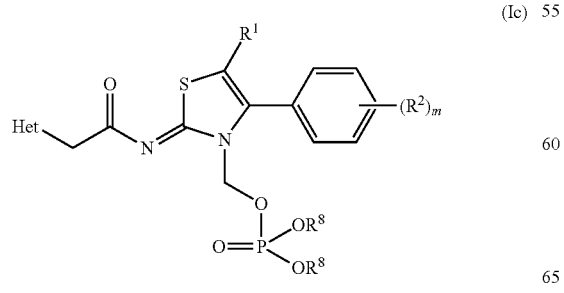

(Ic)

or a pharmaceutically acceptable salt thereof, wherein,

Het is selected from the group consisting of

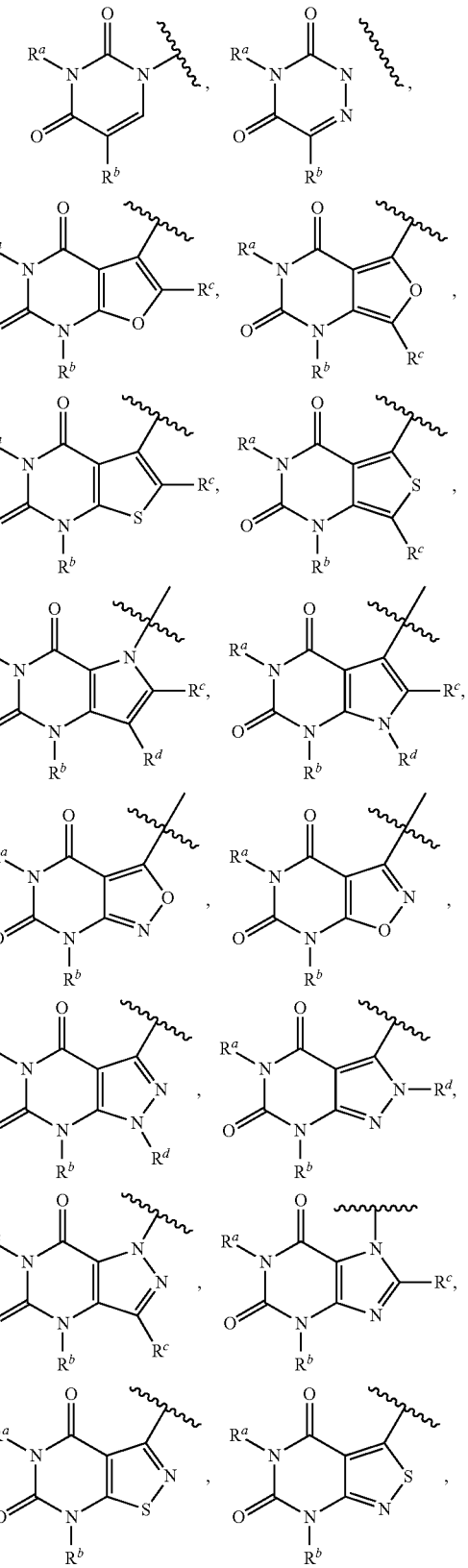

-continued

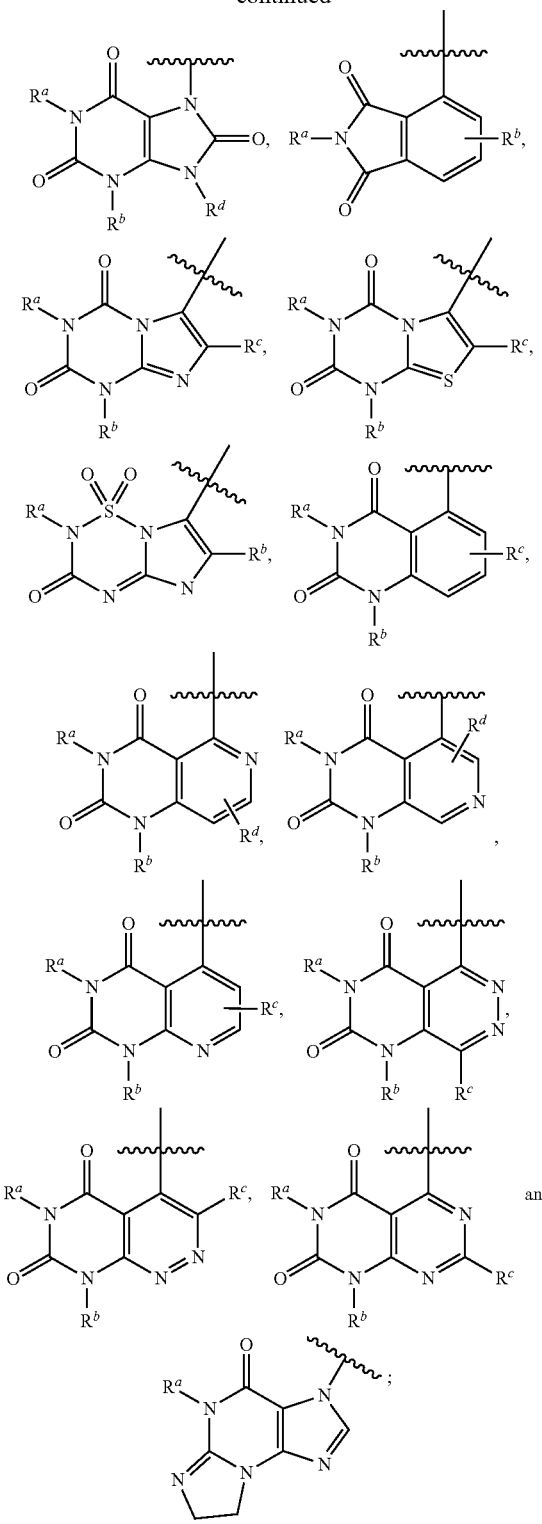

$R^1$ is selected from hydrogen, halogen, cyano, hydroxyl, nitro, —$NR^eR^f$, substituted or unsubstituted alkyl, alkoxy, haloalkyl, haloalkoxy, cycloalkyl, cycloalkylalkyl, aryl, arylalkyl, heteroaryl, heteroarylalkyl, heterocyclic ring and heterocyclylalkyl;

at each occurrence, $R^2$, which may be the same or different, is independently selected from halogen, cyano, hydroxyl, nitro, —$NR^eR^f$, substituted or unsubstituted alkyl, alkoxy, haloalkyl, haloalkoxy, cycloalkyl, cycloalkylalkyl, aryl, arylalkyl, heteroaryl, heteroarylalkyl, heterocyclic ring and heterocyclylalkyl;

$R^8$ is selected from hydrogen, $C_1$-$C_4$alkyl, arylalkyl and pharmaceutically acceptable cation ($M^+$ or $M^{2+}$);

$R^a$, $R^b$ and $R^d$, which may be the same or different, are each independently selected from hydrogen, trifluoromethyl, difluoromethyl, 2,2,2-trifluoroethyl and $C_1$-$C_4$alkyl;

$R^c$ is selected from hydrogen, halogen, trifluoromethyl, difluoromethyl, 2,2,2-trifluoroethyl and $C_1$-$C_4$alkyl;

$R^e$ and $R^f$, which may be the same or different, are independently selected from hydrogen, substituted or unsubstituted alkyl and hydroxyalkyl; or $R^e$ and $R^f$ together with the nitrogen atom to which they are attached, form a cyclic ring, which may be monocyclic, bicyclic or tricyclic rings, which is substituted or unsubstituted and wherein the cyclic ring optionally contains one or more heteroatoms selected from O, N or S; 'm' is an integer ranging from 0 to 5, both inclusive;

The compounds of formula (Ic) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, claim or any other embodiment defined herein. Thus the invention contemplates all possible combinations and permutations of the various independently described embodiments. For example, the invention provides compounds of formula (Ic) as defined above wherein $R^1$ is hydrogen (according to an embodiment defined below) and $R^8$ is hydrogen (according to an embodiment defined below).

According to one embodiment, specifically provided are compounds of the formula (Ic) in which $R^1$ is hydrogen.

According to another embodiment, specifically provided are compounds of the formula (Ic) in which Het is selected from

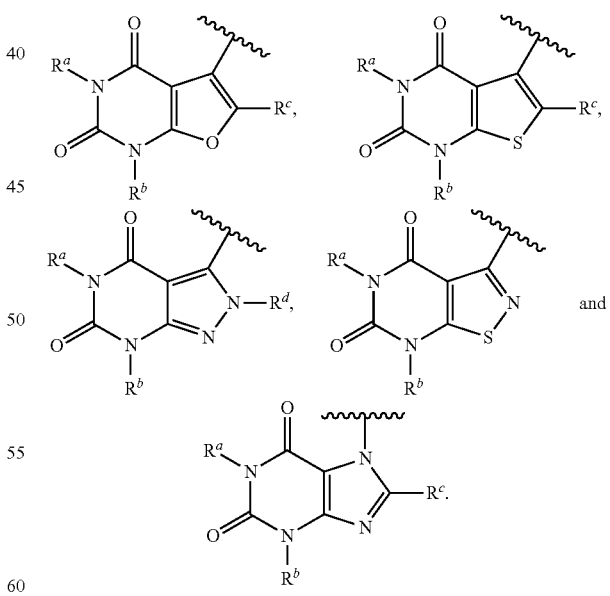

In this embodiment $R^a$, and $R^b$ are independently selected from $C_1$-$C_4$alkyl (e.g. methyl, ethyl), trifluoromethyl, difluoromethyl, 2,2,2-trifluoroethyl and hydrogen; $R^c$ is independently selected from hydrogen, $C_1$-$C_4$alkyl (e.g. methyl, ethyl), trifluoromethyl, difluoromethyl, 2,2,2-trifluoroethyl and halogen.

According to yet another embodiment, specifically provided are compounds of the formula (Ic) in which Het is selected from

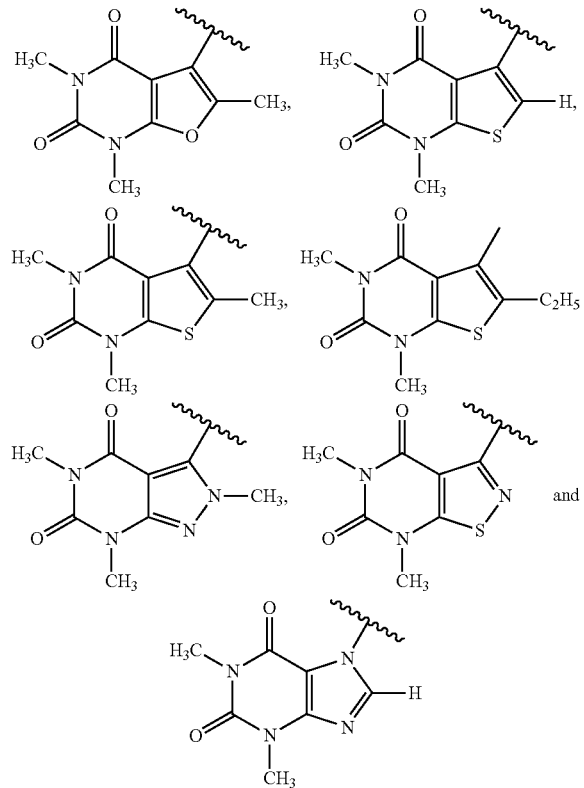

According to yet another embodiment, specifically provided are compounds of the formula (Ic) in which R² is selected from halogen (e.g. fluorine, chlorine), haloalkyl (e.g. trifluoromethyl) and haloalkoxy (e.g. trifluoromethoxy).

According to yet another embodiment, specifically provided are compounds of the formula (Ic) in which 'm' is 1, 2 or 3.

According to yet another embodiment, specifically provided are compounds of the formula (Ic) in which R² is fluorine (—F), chlorine (—Cl), trifluoromethyl (—CF₃) or trifluoromethoxy (—OCF₃); and 'm' is 2 or 3.

According to yet another embodiment, specifically provided are compounds of the formula (Ic) in which R⁸ is hydrogen.

According to yet another embodiment R⁸ is pharmaceutically acceptable cation (M⁺ or M²⁺) such as sodium, potassium, ammonium, calcium and magnesium.

According to another embodiment, specifically provided are compounds of the following formula:

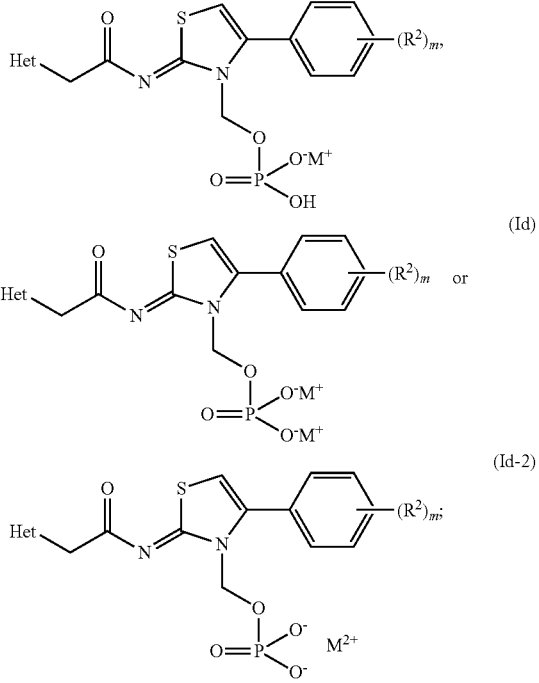

in this embodiment, Het is selected from

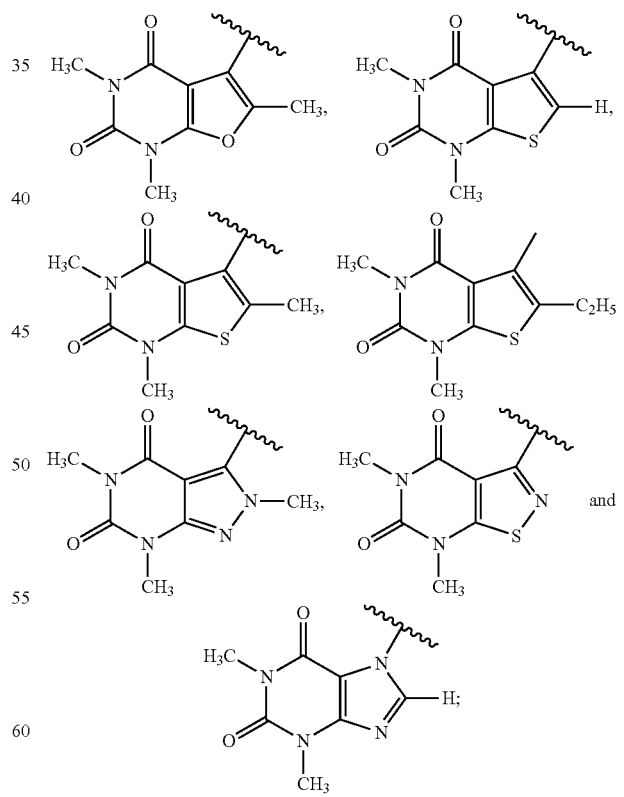

R² is fluorine (—F), chlorine (—Cl), trifluoromethyl or trifluoromethoxy; and 'm' is 2 or 3; further in this embodiment, M⁺ is pharmaceutically acceptable cation such as sodium, potassium, and ammonium; M' is pharmaceutically acceptable cation such as calcium, and magnesium.

According to another embodiment, specifically provided are compounds of the following formula:

[2-{[(1,3-Dimethyl-2,4-dioxo-1,2,3,4-tetrahydrothieno[2,3-d]pyrimidin-5-yl) acetyl]imino}-4-[3-fluoro-4-(trifluoromethyl)phenyl]-1,3-thiazol-3 (2H)-yl]methyl dihydrogen phosphate;

Disodium[2-{[(1,3-dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methyl phosphate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl dihydrogen phosphate Disodium[4-[2,4-difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl phosphate;

4-(2,4-Difluoro-3-(trifluoromethyl)phenyl)-2-((2-(1,3,6-trimethyl-2,4-dioxo-1,2,3,4-tetrahydrothieno[2,3-d]pyrimidin-5-yl)acetyl)imino)thiazol-3(2H)-yl)methyl dihydrogen phosphate;

Disodium (4-(2,4-difluoro-3-(trifluoromethyl)phenyl)-2-((2-(1,3,6-trimethyl-2,4-dioxo-1,2,3,4-tetrahydrothieno[2,3-d]pyrimidin-5-yl)acetyl)imino)thiazol-3(2H)-yl)methyl phosphate;

[2-{[(6-ethyl-1,3-dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methyl dihydrogen phosphate;

Disodium[2-{[(6-ethyl-1,3-dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methyl phosphate;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl dihydrogen phosphate;

Disodium[4-[3-chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl phosphate:

4-[2,3-Difluoro-4-(trifluoromethyl)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl dihydrogen phosphate;

4-(2,4-Difluoro-3-(trifluoromethyl)phenyl)-2-((2-(2,5,7-trimethyl-4,6-dioxo-4,5,6,7-tetrahydro-2H-pyrazolo[3,4-d]pyrimidin-3-yl)acetyl)imino)thiazol-3(2H)-yl)methyl dihydrogen phosphate;

Disodium-(4-(2,4-difluoro-3-(trifluoromethyl)phenyl)-2-((2-(2,5,7-trimethyl-4,6-dioxo-4,5,6,7-tetrahydro-2H-pyrazolo[3,4-d]pyrimidin-3-yl)acetyl)imino)thiazol-3(2H)-yl)methyl phosphate;

(4-(3,4-Dichlorophenyl)-2-((2-(1,3-dimethyl-2,6-dioxo-2,3-dihydro-1H-purin-7(6H)-yl)acetyl)imino)thiazol-3(2H)-yl)methyl dihydrogen phosphate;

[4-[2,3-Difluoro-4-(trifluoromethyl)phenyl]-2-{[(5,7-dimethyl-4,6-dioxo-4,5,6,7-tetrahydro[1,2]thiazolo[5,4-d]pyrimidin-3-yl)acetyl]imino}-1,3-thiazol-3 (2H)-yl]methyl dihydrogen phosphate;

Disodium-(4-(2,3-difluoro-4-(trifluoromethyl)phenyl)-2-((2-(5,7-dimethyl-4,6-dioxo-4,5,6,7-tetrahydroisothiazolo[5,4-d]pyrimidin-3-yl)acetyl)imino)thiazol-3(2H)-yl)methyl phosphate.

In a broader aspect, the invention relates to compound of formula (I) as defined herein, which revert under physiological conditions into a compound having formula (I)

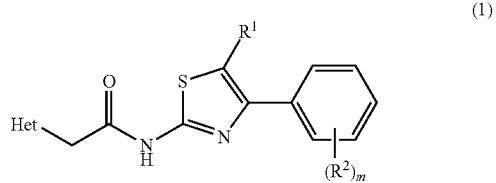

(1)

wherein Het', $R^1$, $R^2$ and m have the same meaning as defined herein for compound of formula (I).

According to one embodiment, specifically provided are compounds of formula (I) having better aqueous solubility over the corresponding compound of formula (1).

According to another embodiment, compound [4-[2,4-difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl glycinate hydrochloride has better aqueous solubility over N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide.

According to yet another embodiment, compound [4-[2,4-difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl piperidine-4-carboxylate hydrochloride has better aqueous solubility over N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide.

According to yet another embodiment, compound [2-{[(1,3-dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methyl dihydrogen phosphate has better aqueous solubility over 2-(1,3-dimethyl-2,4-dioxo-1,2,3,4-tetrahydrothieno[2,3-d]pyrimidin-5-yl)-N-{4-[3-fluoro-4-(trifluoromethyl)phenyl]-1,3-thiazol-2-yl}acetamide.

According to one embodiment, specifically provided are compounds of formula (I), (Ia), (Ib) or (Ic) with better pharmacokinetic properties (Cmax and AUC) with respect to corresponding compound of formula (1).

According to one embodiment, compound [2-{[(1,3-dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3 (2H)-yl]methyl L-isoleucinate hydrochloride has better pharmacokinetic properties (Cmax and AUC) when compared to 2-(1,3-dimethyl-2,4-dioxo-1,2,3,4-tetrahydrothieno[2,3-d]pyrimidin-5-yl)-N-{4-[3-fluoro-4-(trifluoromethyl)phenyl]-1,3-thiazol-2-yl}acetamide.

According to another embodiment, compound [4-[2,4-difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl L-isoleucinate hydrochloride has better pharmacokinetic properties (Cmax and AUC) when compared to N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide.

According to yet another embodiment, compound [2-{[(1,3-dimethyl-2,4-dioxo-1,2,3,4-tetrahydrothieno[2,3-d]pyrimidin-5-yl)acetyl]imino}-4-[3-fluoro-4-(trifluoromethyl)

phenyl]-1,3-thiazol-3(2H)-yl]methyl dihydrogen phosphate has better pharmacokinetic properties (Cmax and AUC) when compared to 2-(1,3-dimethyl-2,4-dioxo-1,2,3,4-tetrahydrothieno[2,3-d]pyrimidin-5-yl)-N-{4-[3-fluoro-4-(trifluoromethyl)phenyl]-1,3-thiazol-2-yl}acetamide.

According to yet another embodiment, compound [4-[3-chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl piperidine-4-carboxylate hydrochloride has better pharmacokinetic properties (Cmax and AUC) when compared to N-{4-[3-chloro-4-(trifluoromethoxy)phenyl]-1,3-thiazol-2-yl}-2-(1,3,6-trimethyl-2,4-dioxo-1,2,3,4-tetrahydrofuro[2,3-d]pyrimidin-5-yl)acetamide.

According to yet another embodiment, compound [4-[3-chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl glycinate hydrochloride has better pharmacokinetic properties (Cmax and AUC) when compared to N-{4-[3-chloro-4-(trifluoromethoxy)phenyl]-1,3-thiazol-2-yl}-2-(1,3,6-trimethyl-2,4-dioxo-1,2,3,4-tetrahydrofuro[2,3-d]pyrimidin-5-yl)acetamide.

According to yet another embodiment, compound [4-[3-chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl L-valinate hydrochloride has better pharmacokinetic properties (Cmax and AUC) when compared to N-{4-[3-chloro-4-(trifluoromethoxy)phenyl]-1,3-thiazol-2-yl}-2-(1,3,6-trimethyl-2,4-dioxo-1,2,3,4-tetrahydrofuro[2,3-d]pyrimidin-5-yl)acetamide.

According to yet another embodiment, compound [4-[3-chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl dihydrogen phosphate has better pharmacokinetic properties (Cmax and AUC) when compared to N-{4-[3-chloro-4-(trifluoromethoxy)phenyl]-1,3-thiazol-2-yl}-2-(1,3,6-trimethyl-2,4-dioxo-1,2,3,4-tetrahydrofuro[2,3-d]pyrimidin-5-yl)acetamide According to yet another embodiment, compound 4-(2,4-difluoro-3-(trifluoromethyl)phenyl)-2-((2-(2,5,7-trimethyl-4,6-dioxo-4,5,6,7-tetrahydro-2H-pyrazolo[3,4-d]pyrimidin-3-yl)acetyl)imino)thiazol-3(2H)-yl)methyl dihydrogen phosphate has better pharmacokinetic properties (Cmax and AUC value) when compared to N-(4-(2,4-difluoro-3-(trifluoromethyl)phenyl)thiazol-2-yl)-2-(2,5,7-trimethyl-4,6-dioxo-4,5,6,7-tetrahydro-2H-pyrazolo[3,4-d]pyrimidin-3-yl)acetamide.

It should be understood that the formulas (I), (Ia), (Ib) or (Ic) structurally encompasses N-oxide, all tautomers, geometrical isomers, stereoisomers, including enantiomers and diastereomers and pharmaceutically acceptable salts that may be contemplated from the chemical structure of the genera described herein.

The present invention also provides a pharmaceutical composition that includes at least one compound described herein and at least one pharmaceutically acceptable excipient, such as a pharmaceutically acceptable carrier or diluent. Preferably, the pharmaceutical composition comprises a therapeutically effective amount of at least one compound described herein. The compounds described in the present patent application may be associated with a pharmaceutically acceptable excipient, such as a carrier or a diluent or be diluted by a carrier, or enclosed within a carrier which can be in the form of a capsule, sachet, paper or other container.

The compounds of the present invention can be administered as pharmaceutical composition containing, for example, 0.1 to 99.5% (more preferably, 0.5 to 90%) of active ingredient in combination with a pharmaceutically acceptable carrier. The ultimate dose will depend on the condition being treated, the route of administration and the age, weight and condition of the patient and will be the doctor's discretion.

Compounds of the present invention may be used in the manufacture of medicaments for the treatment of any diseases disclosed herein. The compounds and pharmaceutical compositions described herein are useful for modulating TRPA1 receptors, wherein modulation is believed to be related to a variety of disease states.

The compound of the present invention can be administered alone or in combination with other therapeutic agents. For instance, the TRPA1 modulator is administered conjointly with one or more of an anti-inflammatory agent, anti-acne agent, anti-wrinkle agent, anti-scarring agent, anti-psoriatic agent, anti-proliferative agent, anti-fungal agent, anti-viral agent, anti-septic agent, anti-migraine agent, keratolytic agent, or a hair growth inhibitor In accordance with another aspect, the present patent application further provides a method of inhibiting TRPA1 receptors in a subject in need thereof by administering to the subject one or more compounds described herein in the amount effective to cause inhibition of such receptor.

DETAILED DESCRIPTION OF THE INVENTION

Definitions

The terms "halogen" or "halo" means fluorine (fluoro), chlorine (chloro), bromine (bromo), or iodine (iodo).

The term "alkyl" refers to a hydrocarbon chain radical that includes solely carbon and hydrogen atoms in the backbone, containing no unsaturation, having from one to eight carbon atoms (i.e. $C_{1-8}$alkyl), and which is attached to the rest of the molecule by a single bond, e.g., methyl, ethyl, n-propyl, 1-methylethyl (isopropyl), n-butyl, n-pentyl and 1,1-dimethylethyl (t-butyl). The term "$C_1$-$C_6$alkyl" refers to an alkyl chain having 1 to 6 carbon atoms. The term "$C_1$-$C_4$alkyl" refers to an alkyl chain having 1 to 4 carbon atoms. Unless set forth or recited to the contrary, all alkyl groups described or claimed herein may be straight chain or branched, substituted or unsubstituted.

The term "alkoxy" refers an alkyl group attached via an oxygen linkage to the rest of the molecule (i.e. $C_{1-8}$alkoxy). Examples of such alkoxy moiety include, but are not limited to, —$OCH_3$ and —$OC_2H_5$. Unless set forth or recited to the contrary, all alkoxy groups described herein may be straight chain or branched, substituted or unsubstituted.

The term "haloalkyl" refers to at least one halo group (selected from F, Cl, Br or I), linked to an alkyl group as defined above (i.e. halo$C_{1-8}$alkyl). Examples of such haloalkyl moiety include, but are not limited to, trifluoromethyl, difluoromethyl and fluoromethyl groups. Unless set forth or recited to the contrary, all haloalkyl groups described herein may be straight chain or branched, substituted or unsubstituted.

The term "haloalkoxy" refers to an alkoxy group substituted with one or more halogen atoms (i.e. halo$C_{1-8}$alkoxy). Examples of "haloalkoxy" include but are not limited to fluoromethoxy, difluoromethoxy, trifluoromethoxy, 2,2,2-trifluoroethoxy, pentafluoroethoxy, pentachloroethoxy, chloromethoxy, dichlorormethoxy, trichloromethoxy and 1-bromoethoxy. Unless set forth or recited to the contrary, all haloalkoxy groups described herein may be straight chain or branched, substituted or unsubstituted.

The term "hydroxyalkyl" refers to an alkyl group as defined above wherein one to three hydrogen atoms on different carbon atoms is/are replaced by hydroxyl groups (i.e. hydroxyC$_{1-8}$alkyl). Examples of hydroxyalkyl moiety include, but are not limited to —CH$_2$OH and —C$_2$H$_4$OH.

The term "cycloalkyl" denotes a non-aromatic mono or multicyclic ring system of 3 to about 12 carbon atoms for example C$_{3-12}$cycloalkyl, such as cyclopropyl, cyclobutyl, cyclopentyl and cyclohexyl. Examples of multicyclic cycloalkyl groups include, but are not limited to, perhydronapththyl, adamantyl and norbornyl groups, bridged cyclic groups or sprirobicyclic groups, e.g., sprio(4,4)non-2-yl, spiro[3,3]heptanyl, spiro[3,4]octanyl and spiro[4,4]heptanyl. Unless set forth or recited to the contrary, all cycloalkyl groups described herein may be substituted or unsubstituted.

The term "cycloalkylalkyl" refers to a cyclic ring-containing radical having 3 to about 8 carbon atoms directly attached to an alkyl group for example C$_{3-8}$cycloalkylC$_{1-8}$alkyl. The cycloalkylalkyl group may be attached to the main structure at any carbon atom in the alkyl group that results in the creation of a stable structure. Examples of cycloalkylalkyl moiety include, but are not limited to cyclopropylmethyl, cyclobutylethyl, and cyclopentylethyl. Unless set forth or recited to the contrary, all cycloalkylalkyl groups described or claimed herein may be substituted or unsubstituted.

The term "aryl" refers to an aromatic radical having 6 to 14 carbon atoms (i.e. C$_{6-14}$aryl), including monocyclic, bicyclic and tricyclic aromatic systems, such as phenyl, naphthyl, tetrahydronapthyl, indanyl and biphenyl. Unless set forth or recited to the contrary, all aryl groups described herein may be substituted or unsubstituted.

The term "arylalkyl" refers to an aryl group as defined above directly bonded to an alkyl group as defined above (i.e. C$_{6-14}$arylC$_{1-8}$alkyl). Examples of arylalkyl moiety include, but are not limited to —CH$_2$C$_6$H$_5$ and —C$_2$H$_4$C$_6$H$_5$. Unless set forth or recited to the contrary, all arylalkyl groups described herein may be substituted or unsubstituted.

The term "heteroaryl" unless otherwise specified refers to substituted or unsubstituted 5 to 14 membered aromatic heterocyclic ring radical with one or more heteroatom(s) independently selected from N, O or S. The heteroaryl may be a mono-, bi- or tricyclic ring system. The heteroaryl ring radical may be attached to the main structure at any heteroatom or carbon atom that results in the creation of a stable structure. Examples of such heteroaryl ring radicals include, but are not limited to oxazolyl, isoxazolyl, imidazolyl, furyl, indolyl, isoindolyl, pyrrolyl, triazolyl, triazinyl, tetrazoyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl and phthalazinyl. Unless set forth or recited to the contrary, all heteroaryl groups described herein may be substituted or unsubstituted.

The term "heteroarylalkyl" refers to a heteroaryl ring radical directly bonded to an alkyl group (i.e. heterarylC$_{1-8}$alkyl). The heteroarylalkyl radical may be attached to the main structure at any carbon atom in the alkyl group that results in the creation of a stable structure. Unless set forth or recited to the contrary, all heteroarylalkyl groups described herein may be substituted or unsubstituted.

The term "heterocyclic ring" or "heterocyclyl" unless otherwise specified refers to substituted or unsubstituted non-aromatic 3 to 15 membered ring radical which consists of carbon atoms and from one to five heteroatoms selected from nitrogen, phosphorus, oxygen and sulfur. The heterocyclic ring radical may be a mono-, bi- or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; also, unless otherwise constrained by the definition the heterocyclic ring or heterocyclyl may optionally contain one or more olefinic bond(s). Examples of such heterocyclic ring radicals include, but are not limited to azepinyl, azetidinyl, benzodioxolyl, benzodioxanyl, chromanyl, dioxolanyl, dioxaphospholanyl, decahydroisoquinolyl, indanyl, indolinyl, isoindolinyl, isochromanyl, isothiazolidinyl, isoxazolidinyl, morpholinyl, oxazolinyl, oxazolidinyl, oxadiazolyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisquinolyl, tetrahydrofuryl, tetrahydropyranyl, thiazolinyl, thiazolidinyl, thiamorpholinyl, thiamorpholinyl sulfoxide, thiamorpholinyl sulfone, 7-aza-spiro[3,3]heptanyl, 7-spiro[3,4]octanyl, and 7-aza-spiro[3,4]octanyl. The heterocyclic ring radical may be attached to the main structure at any heteroatom or carbon atom that results in the creation of a stable structure. Unless set forth or recited to the contrary, all heterocyclyl groups described herein may be substituted or unsubstituted.

The term "heterocyclylalkyl" refers to a heterocyclic ring radical directly bonded to an alkyl group (i.e. heterocyclyl C$_{1-8}$alkyl). The heterocyclylalkyl radical may be attached to the main structure at any carbon atom in the alkyl group that results in the creation of a stable structure. Unless set forth or recited to the contrary, all heterocyclylalkyl groups described herein may be substituted or unsubstituted.

Unless otherwise specified, the term "substituted" as used herein refers to a group or moiety having one or more of the substituents attached to the structural skeleton of the group or moiety, including, but not limited to such substituents as hydroxy, halogen, carboxyl, cyano, nitro, oxo (=O), thio (=S), substituted or unsubstituted alkyl, substituted or unsubstituted haloalkyl, substituted or unsubstituted alkoxy, substituted or unsubstituted haloalkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstiuted guanidine, —COOR$^x$, —C(O)R$^x$, —C(S)R$^x$, —C(O)NR$^x$R$^y$, —C(O)ONR$^x$R$^y$, —NR$^x$CONR$^y$R$^z$, —N(R$^x$)SOR$^y$, —N(R$^x$)SO$_2$R$^y$, -(=N—N(R$^x$)R$^y$), —NR$^x$C(O)OR$^y$, —NR$^x$R$^y$, —NR$^x$C(O)R$^y$, —NR$^x$C(S)R$^y$, —NR$^x$(S)NR$^y$R$^z$, —SONR$^x$R$^y$, —SO$_2$NR$^x$R$^y$, —OR$^x$, —OC(O)R$^x$, —OC(O)NR$^x$R$^y$, —SR$^x$, —SOR$^x$, —SO$_2$R$^x$, and —ONO$_2$, wherein R$^x$, R$^y$ and R$^z$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. The substituents in the aforementioned "substituted" groups cannot be further substituted. For example, when the substituent on "substituted alkyl" is "substituted aryl", the substituent on "substituted aryl" can be unsubstituted alkenyl but cannot be "substituted alkenyl".

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans). Other mammals include domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

Pharmaceutically acceptable salts forming part of this patent application include salts derived from inorganic bases (such as Li, Na, K, Ca, Mg, Fe, Cu, Zn, and Mn), salts of organic bases (such as N,N'-diacetylethylenediamine, glucamine, triethylamine, choline, hydroxide, dicyclohexylamine, metformin, benzylamine, trialkylamine, and thiamine), salts of chiral bases (such as alkylphenylamine, glycinol, and phenyl glycinol), salts of natural amino acids (such as glycine, alanine, valine, leucine, isoleucine, norleucine, tyrosine, cystine, cysteine, methionine, proline, hydroxy proline, histidine, ornithine, lysine, arginine, and serine), salts of non-natural amino acids (such as D-isomers or substituted amino acids), salts of guanidine, salts of substituted guanidine (wherein the substituents are selected from nitro, amino, alkyl, alkenyl or alkynyl), ammonium salts, substituted ammonium salts and aluminum salts. Other pharmaceutically acceptable salts include acid addition salts (where appropriate) such as sulphates, nitrates, phosphates, perchlorates, borates, hydrohalides, acetates (such as trifluoroacetate), tartrates, maleates, citrates, fumarates, succinates, palmoates, methanesulphonates, benzoates, salicylates, benzenesulfonates, ascorbates, glycerophosphates and ketoglutarates. Yet other pharmaceutically acceptable salts include, but are not limited to, quaternary ammonium salts of the compounds of invention with alkyl halides or alkyl sulphates (such as MeI or $Me_2SO_4$).

Compounds described herein can comprise one or more asymmetric carbon atoms and thus can occur as racemic mixtures, enantiomers and diastereomers. These compounds can also exist as conformers/rotamers. All such isomeric forms of these compounds are expressly included in the present patent application. Although the specific compounds exemplified in this application may be depicted in a particular stereochemical configuration, compounds having either the opposite stereochemistry at any given chiral centre are envisioned as a part thereof. In addition, compounds of Formula I can exist in different geometrical isomeric forms. Unless otherwise stated a reference to a particular compound includes all such isomeric forms, including racemic and other mixtures thereof. The various isomeric forms of the compounds of the present invention may be separated from one another by methods known in the art or a given isomer may be obtained by stereospecific or asymmetric synthesis. Tautomeric forms and mixtures of compounds described herein are also contemplated. It is also to be understood that compounds of the invention may exist in solvated forms (such as hydrates) as well as unsolvated forms, and that the invention encompasses all such forms.

Pharmaceutical Compositions

The pharmaceutical composition of the present patent application includes at least one compound described herein and at least one pharmaceutically acceptable excipient (such as a pharmaceutically acceptable carrier or diluent). Preferably, the pharmaceutical composition includes the compound(s) described herein in an amount sufficient to inhibit TRPA1 in a subject (e.g., a human).

The compound of the present invention may be associated with a pharmaceutically acceptable excipient (such as a carrier or a diluent) or be diluted by a carrier, or enclosed within a carrier which can be in the form of a capsule, sachet, paper or other container.

The pharmaceutical compositions may be prepared by techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

Methods of Treatment

The compounds and pharmaceutical compositions of the present invention can be administered to treat any disorder, condition, or disease treatable by inhibition of TRPA1. For instance, the compounds and pharmaceutical compositions of the present invention are suitable for treatment or prophylaxis of the following diseases, conditions and disorders mediated or associated with the activity of TRPA1 receptors: pain, chronic pain, complex regional pain syndrome, neuropathic pain, postoperative pain, rheumatoid arthritic pain, osteoarthritic pain, back pain, visceral pain, cancer pain, algesia, neuralgia, migraine, neuropathies, chemotherapy—induced neuropathies, eye—irritation, bronchial—irritation, skin—irritation (atopic dermatitis), Frost-bites (cold—bite), spasticity, catatonia, catalepsy, parkinsons, diabetic neuropathy, sciatica, HIV-related neuropathy, post-herpetic neuralgia, fibromyalgia, nerve injury, ischaemia, neurodegeneration, stroke, post stroke pain, multiple sclerosis, respiratory disorder, inflammatory disorders, oesophagitis, gastroeosophagal reflux disorder (GERD), irritable bowel syndrome, inflammatory bowel disease, pelvic hypersensitivity, urinary incontinence, cystitis, burns, psoriasis, eczema, emesis, stomach duodenal ulcer and pruritus. By the term "respiratory disorder", it is meant any condition or disease related to respiration or the respiratory system and includes but is not limited to airway inflammation, asthma, emphysema, bronchitis, COPD, sinusitis, rhinitis, cough, respiratory depression, reactive airways dysfunction syndrome (RADS), acute respiratory distress syndrome (ARDS), irritant induced asthma, occupational asthma, sensory hyper-reactivity, multiple chemical sensitivity, and aid in smoking cessation therapy. The connection between therapeutic effect and inhibition of TRPA1 is illustrated, for example, in Story, G. M. et al. *Cell*, 2003, 112, 819-829; McMahon, S. B. and Wood, J. N., *Cell*, 2006, 124, 1123-1125; Voorhoeve, P. M. et al. Cell, 2006, 124, 1169-1181; Wissenbach, U, Niemeyer, B. A. and Flockerzi, V. *Biology of the Cell*, 2004, 96, 47-54; and the references cited therein.

Pain can be acute or chronic. While acute pain is usually self-limiting, chronic pain persists for 3 months or longer and can lead to significant changes in a patient's personality; lifestyle, functional ability and overall quality of life (K. M. Foley, *Pain*, in Cecil Textbook of Medicine; J. C. Bennett & F. Plum (eds.), 20th ed., 1996, 100-107). The sensation of pain can be triggered by any number of physical or chemical stimuli and the sensory neurons which mediate the response to this harmful stimulus are termed as "nociceptors". Nociceptors are primary sensory afferent (C and Aδ fibers) neurons that are activated by a wide variety of noxious stimuli including chemical, mechanical, thermal and proton (pH<6) modalities. Nociceptors are the nerves which sense and respond to parts of the body which suffer from damage. They signal tissue irritation, impending injury, or actual injury. When activated, they transmit pain signals (via the peripheral nerves as well as the spinal cord) to the brain.

Chronic pain can be classified as either nociceptive or neuropathic. Nociceptive pain includes tissue injury-induced pain and inflammatory pain such as that associated with arthritis. Neuropathic pain is caused by damage to the sensory nerves of the peripheral or central nervous system and is maintained by aberrant somatosensory processing. The pain is typically well localized, constant and often with an aching or throbbing quality. Visceral pain is the subtype of nociceptive pain that involves the internal organs. It tends to be episodic and poorly localized. Nociceptive pain is usually time limited, meaning when the tissue damage heals, the pain typically resolves (arthritis is a notable exception in that it is not time limited).

General Methods of Preparation

The compounds of general formulas (I), (Ia), (Ib), (Ic) and (Id) and specific examples described herein are prepared using techniques known to one skilled in the art through selection of reaction sequences depicted in synthetic schemes 1-16 and as well as by other known methods. Furthermore, in the following schemes, where specific acids, bases, reagents, coupling agents, solvents, etc. are mentioned, it is understood that other suitable reagents may be used and are included within the scope of the present invention. Modifications to reaction conditions, for example, temperature, duration of the reaction or combinations thereof, are envisioned as part of the present invention. The compounds obtained by using the general reaction sequences may be of insufficient purity. These compounds can be purified by using any of the methods for purification of organic compounds known to persons skilled in the art, for example, crystallization or silica gel or alumina column chromatography using different solvents in suitable ratios. All possible geometrical isomers, stereoisomers and tautomers are envisioned within the scope of this invention.

The compounds of the present invention can be prepared by adapting appropriate synthetic approaches known in the literature. The advanced intermediates required for the synthesis of compounds described herein were prepared from commercially available starting materials. 2-Amino-4-arylthiazole derivatives having TRPA1 antagonistic activity used in the preparation of compounds of invention were prepared using procedures described in the following international applications: WO2010109287, WO2010109328, WO2010109329, WO2010109334, WO2009118596, WO2009144548, WO2010004390, WO2010125469, WO2011114184, WO2011132017, WO2007073505, WO2010075353, WO2009158719, WO2009002933 and WO2010132838. Di-tert-butyl iodomethyl phosphate ester was prepared from di-tert-butyl chloromethyl phosphate. The amino acid based pro-moieties used for the preparation of compounds of present invention were prepared using literature procedure. A typical procedure is reported by Iyer, R. P. et al. in *Synthetic Communications*, 1995, 25, 2739-2750.

A general approach for the synthesis of compounds of the general formula (I) (where $R^1$, $R^2$, 'Het' P and 'm' are as defined above) is described in synthetic scheme 1. Thus, coupling reaction of substituted thiazole (1) with compound of the general formula (2) in the presence of a suitable base and a suitable solvent at an appropriate temperature can give compound of general formula (I).

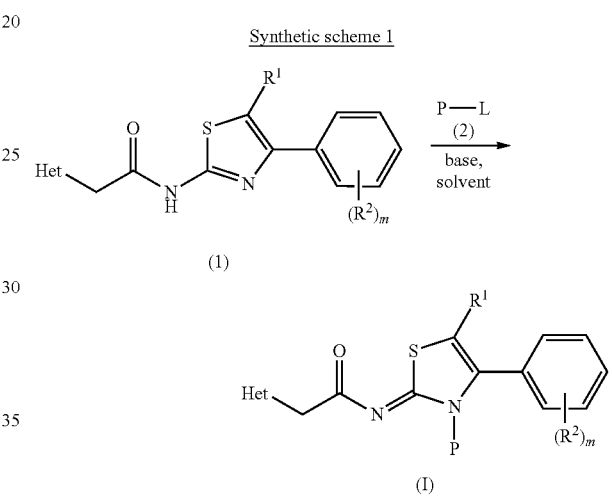

A general approach for the synthesis of N-acyloxymethylene derivative of the formula (Ia) (where Het, $R^1$, $R^2$, $R^3$ and 'm' are as defined above) is described in synthetic scheme 2. The coupling reaction of an appropriately substituted arythiazole of the formula (1) with halomethyl ester of the general formula (3) (wherein L is leaving group such as iodo or chloro) using a suitable base such as sodium hydride in suitable solvent such as DMF or DMSO can give N-acyloxymethylene compound of general formula (Ia). The halomethyl ester of the formula (2) required for the synthesis of (Ia) can be prepared from appropriate carboxylic acid and chloromethyl chlorosulphate as described by Tsujihara, K. et al. in *Synthetic Communications*, 1994, 24, 767-772 and Ralph P. Robinson et al. in *J. Med. Chem.* 1996, 39, 10-18.

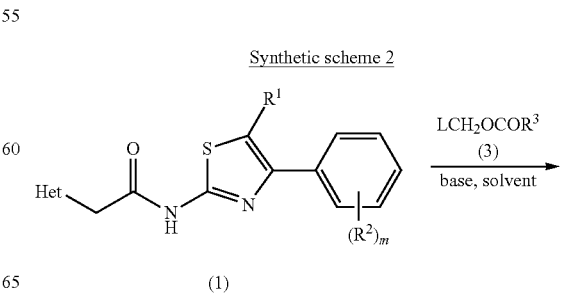

-continued

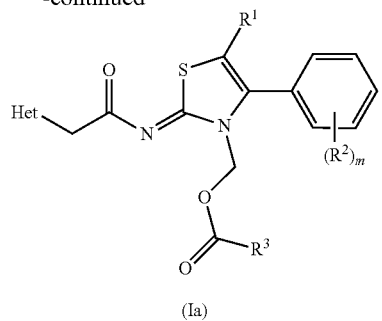

(Ia)

A general approach for the synthesis of compound of the general formula (Ib), where Het, $R^1$, $R^2$, $R^4$ and 'm' are as defined above and L is leaving group such as halogen (e.g., Cl, Br or I) is described in Synthetic scheme 3. The thiazole derivative of the formula (1) is deprotonated using strong base such as sodium hydride in a polar solvent such as DMF and the anion thus formed is allowed to react with intermediate (4) (where Pg is protecting group such as Boc, Cbz, Bn or Fmoc) to give N-acyloxymethylene intermediate, which on further deprotection gives compound of the formula (Ib). The intermediate (4) required for the synthesis of (Ib) is prepared from a natural (biorganic) or unnatural amino acid as described by Tsujihara, K. et al. in *Synthetic Communications*, 1994, 24, 767-772 and Ralph P. Robinson et al. in *J. Med. Chem.* 1996, 39, 10-18.

Synthetic scheme 3

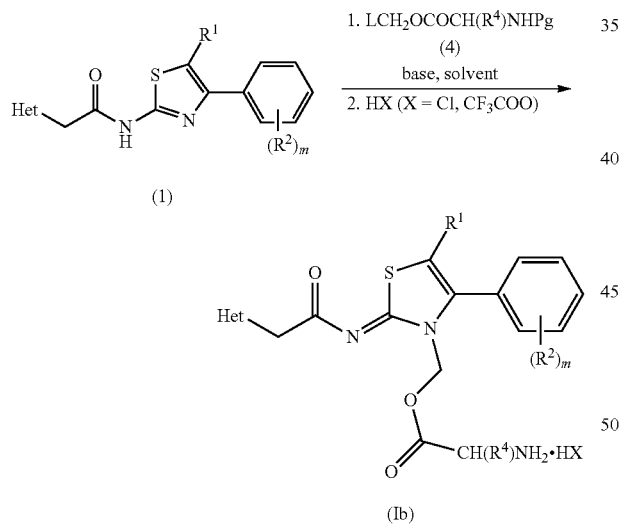

Compounds of the formula (Ib), can also be prepared as per the route shown in Synthetic scheme 4. Thus, reaction of thiazole of formula (1) with chloromethyl chloroformate (5) in the presence of strong base such as sodium hydride can give chloromethyl thiazole intermediate of the formula (6). The coupling reaction of intermediate of the formula (6) with amino group protected amino acid of formula (7) (where Pg is Boc, Cbz, Bn or Fmoc) in the presence of strong base can produce compound of the formula (8). The cleavage of protecting group under acidic conditions can afford compounds of formula (Ib). Similar procedure is described in *J. Med. Chem.* 2011, 54, 751-764.

Synthetic scheme 4

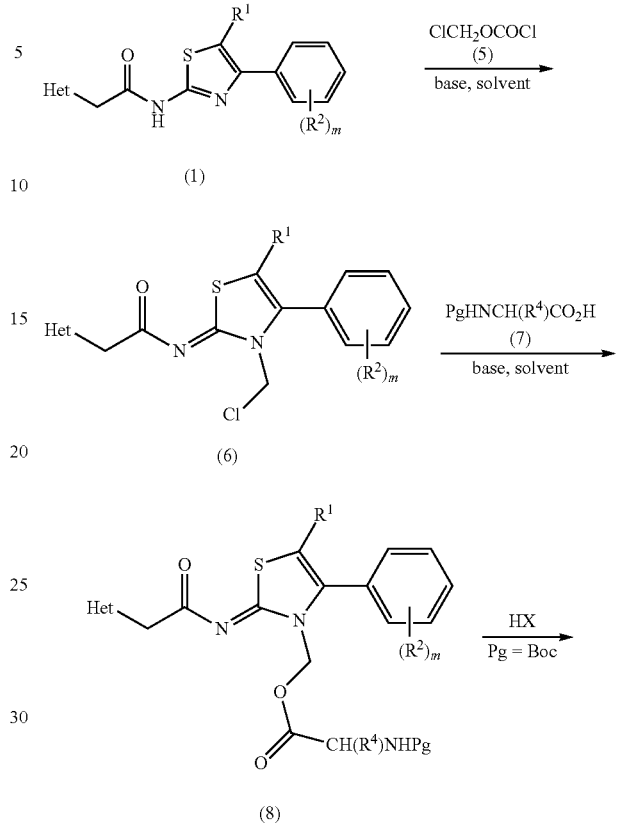

A general approach for the synthesis of N-phosphono oxymethyl derivative of the formula (Ic) is described in synthetic scheme 5. Thus, reaction of thiazole of formula (I) with an appropriate halomethyl phosphate of the formula (9) (where L is Cl, Br, OTs or I and $R^8$ is methyl, ethyl, allyl, tert. butyl, n-butyl, benzyl etc.) in the presence of base such as sodium hydride or sodium tert-butoxide or potassium tert-butoxide in polar aprotic solvent gives phosphono-oxymethylene derivative of the formula (Ic). The procedure used is similar to that is reported by Anette, G. S, et al. in *J. Med. Chem.* 2011, 54, 751-764. The hydrolysis of compound of the formula (Ic) under acidic condition affords phosphoric acid derivative (Ic-1). The phosphoric acid (Ic-1) can be converted to mono or bis salt of the formula (Id-1) and (Id) using appropriate equivalents of metal alkoxides of alkali metals or amines in a suitable solvent. The phosphoric acid derivative (Ic-1) can also form salts with alkaline earth metals such as calcium or magnesium under appropriate conditions. The halomethyl phosphate intermediate of the formula (9) can be prepared from chloromethyl chlorosulphate and appropriate phosphate ester as reported by Antti Mantyla et al. in *Tetrahedron Letters,* 2002, 43, 3793-3794.

Synthetic scheme 5

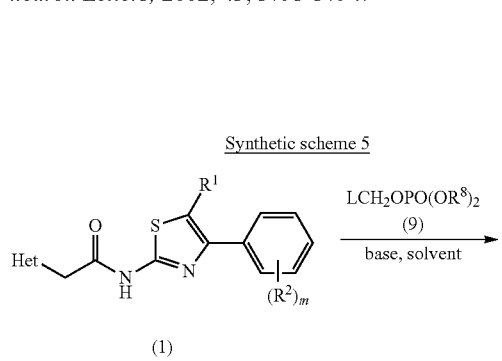

(1)

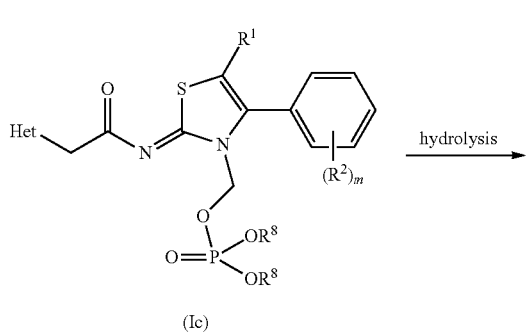

(Ic)

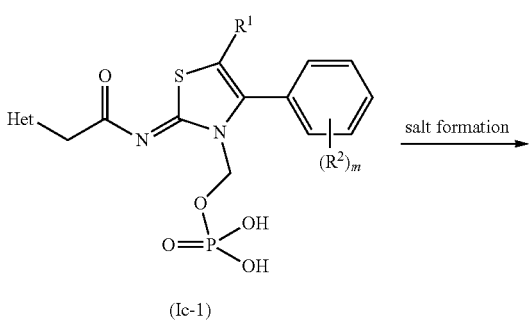

(Ic-1)

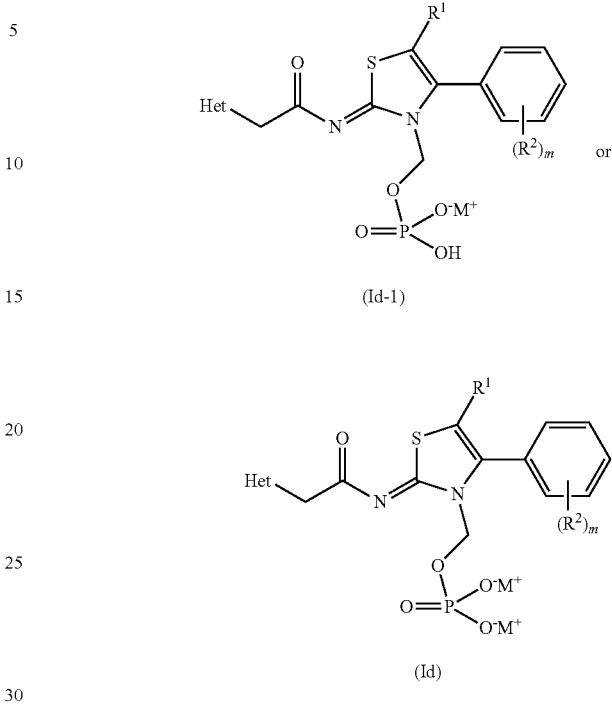

(Id-1)

(Id)

Another approach for the synthesis of N-phosphonooxymethyl derivative of the formula (Id) is described in synthetic scheme 6. In this approach, thiazole derivative (1) can be coupled with chloromethyl chloroformate (5) or chloromethyl tosylate of the formula (10) in the presence of base to give N-chloromethylthiazole compound of formula (6). The reaction of the intermediate (6) with dialkyl phosphate of the formula (11) (where $R^8$ is methyl, ethyl, allyl, tert. butyl, n-butyl, benzyl etc.) in the presence of suitable base such as sodium hydride can give compound of formula (Ic). Alternatively compound of formula (Ic-1) can also be prepared by the reaction of the intermediate (6) with phosphoric acid in the presence of suitable base such N,N-disopropylethylamine in suitable solvent such as acetonitrile. This approach is similar to the one reported by Anette, G. S, et. al. in *J. Med. Chem.* 2011, 54, 751-764. The hydrolysis of compound of the formula (Ic) and salt formation can provide compound of the formula (Id).

Synthetic scheme 6

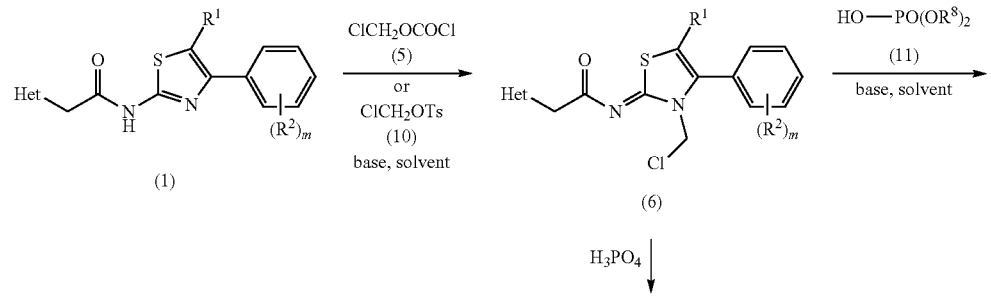

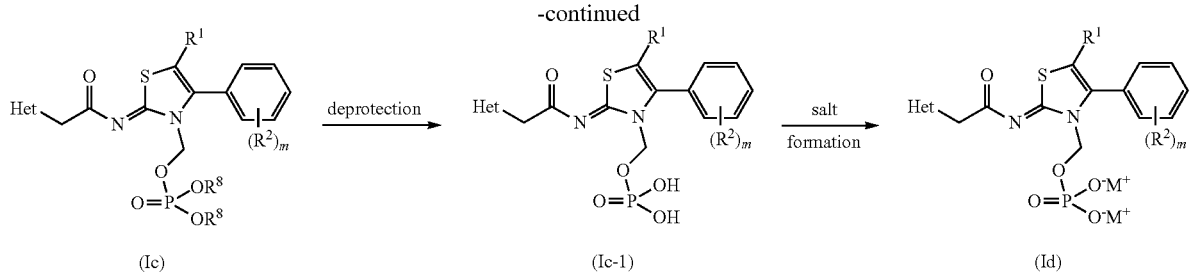

Another approach for the synthesis of phosphono-oxymethyl derivative of the formula (Ic), is described in synthetic scheme 7. Thus, coupling reaction of 2-amino-4-aryl thiazole of formula (12) with halomethyl phosphate of formula (9) (where $R^8$ is methyl, ethyl, allyl, tert. butyl, n-butyl, benzyl etc.) in the presence of strong base such as sodium hydride can provide N-phosphonoxymethyl thiazole of the formula (13). The phosphonoxymethyl thiazole derivative (13) can be coupled with a heteroaryl substituted carboxylic acid of the formula (14) in the presence of strong base such as sodium hydride to afford compounds of the formula (Ic).

mula (6). The coupling reaction of the (6) with dialkyphosphate (11) (where $R^8$ is methyl, ethyl, allyl, tert. butyl, n-butyl, benzyl etc.) can provide compound of the formula (Ic).

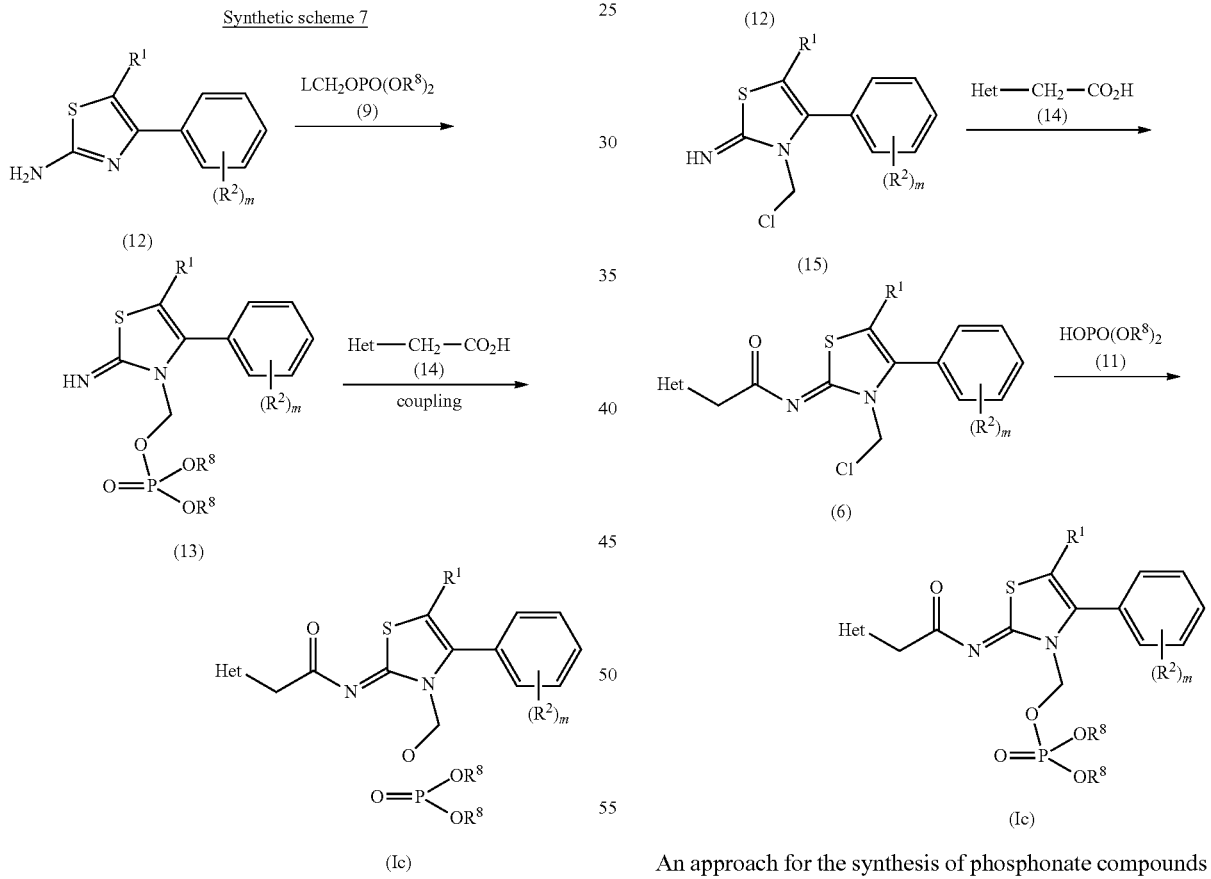

An alternative approach for the synthesis of N-phosphonooxymethyl derivative of the formula (Ic) is shown in synthetic scheme 8. In this approach, 2-amino-4-aryl thiazole of formula (12) can be coupled with chloromethyl chloroformate (5) or chloromethyl tosylate of the formula (10) in the presence of base to give N-chloromethylthiazole of formula (15). The reaction of intermediate of formula (15) with carboxylic acid of the formula (14) in the presence of strong base such as sodium hydride can provide chloromethyl compound of for- An approach for the synthesis of phosphonate compounds of the formula (Id-3) where the thiazole nitrogen is covalently linked to phosphorus, L is leaving group and $R^8$ is methyl, ethyl, allyl, tert butyl, n-butyl, benzyl etc.) is shown in synthetic scheme 9. The thiazole compound of the formula (I) can be deprotonated using strong base such as sodium hydride in a polar solvent such as DMF and the anion thus formed can be allowed to react with halo phosphate ester of formula (16) or pyrophosphate (17) to give N-phosphate derivative of the formula (Ic-2). The hydrolysis of compound of formula (Ic-2) can provide phosphate derivative of the formula (Ic-3). The phosphate derivative (Ic-3) can be converted to mono or bis salts of the formula (Id-2) or (Id-3) using appropriate metal alkoxides or amines An approach for the synthesis of specific examples of the present invention wherein heterocyclic group is a thieno[2,3-d]pyrimidine or furo[2,3-d]pyrimidine or pyrrolo[2,3-d]pyrimidine of general formula (IIa) (where Q is O, N or S and $R^c$ is hydrogen atom or an alkyl group or halogen) is described in synthetic scheme 10. Thus, reaction of thieno[2,3-d]pyrimidine acetamide or furo[2,3-d]pyrimidine or pyrrolo[2,3-d]pyrimidine acetamide of the formula (18) with iodomethyl ester of the formula (19) in the presence of sodium hydride in dry DMF to afford compound of formula (IIa).

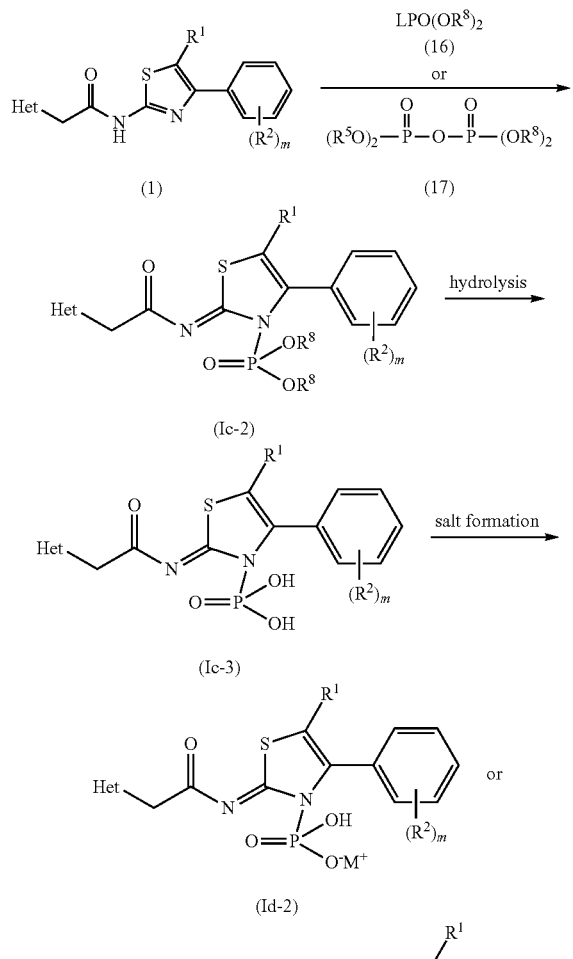

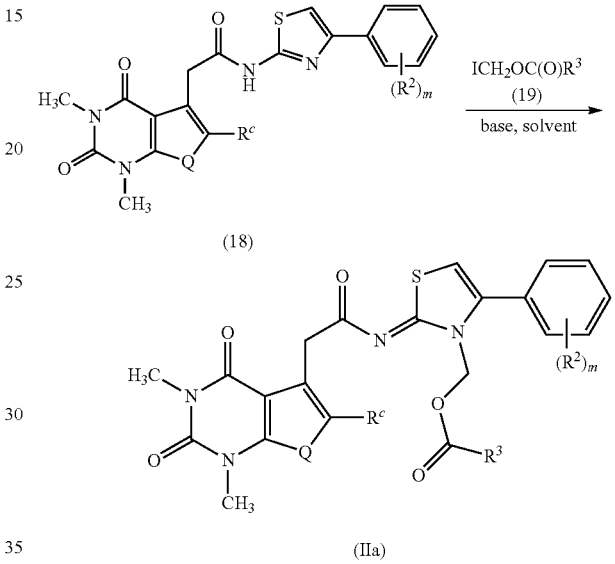

An approach for the synthesis of compound of the invention wherein heterocyclic group constitutes a thieno[2,3-d]pyrimidine or furo[2,3-d]pyrimidine or pyrrolo[2,3-d]pyrimidine acetamide and the pro-moiety derived from an amino acid is shown in Synthetic scheme 11. Thus, thieno[2,3-d]pyrimidine acetamide or furo[2,3-d]pyrimidine acetamide or pyrrolo[2,3-d]pyrimidine acetamide of the formula (18) is deprotonated using sodium hydride in dry DMF and the anion thus formed is allowed to react with an amino acid of the formula (20) to provide N-acyloxymethylene intermediate, which on deprotection of Boc group gives compound of the formula (IIb).

Synthetic scheme 11

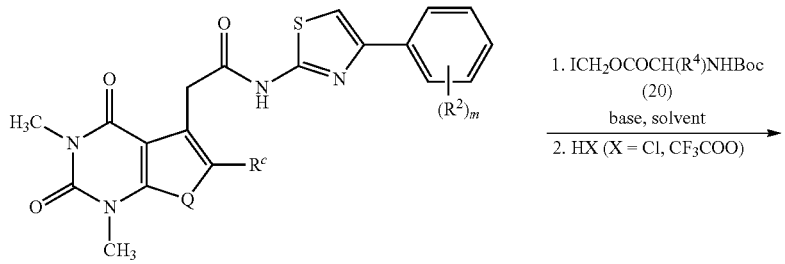

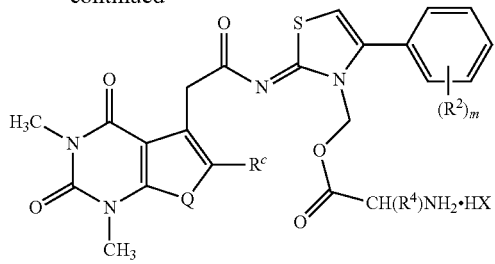

(IIb)

An approach for the synthesis of the compound of the invention wherein the heterocyclic group (Het) is a thieno[2,3-d]pyrimidine or furo[2,3-d]pyrimidine and the pro-moity is a phosphoric acid derivative is shown in Synthetic scheme 12. Thus, the coupling reaction of thieno[2,3-d]pyrimidinyl acetamide or furo[2,3-d]pyrimidine acetamide (18) with halomethyl phosphate of the formula (21) (where X is chloro, bromo, or iodo) in the presence of sodium hydride or sodium tert-butoxide or potassium tert-butoxide in dry DMF gives N-phosphono-oxymethyl compound (IIc). Acid-mediated hydrolysis of compound of the formula (IIc) gave phosphoric acid derivative (Hc-1). The phosphoric acid (IIc-1) is converted to compound of the formula (Hd-2) using suitable base sodium methoxide, sodium-tert-butoxide, sodium bicarbonate or sodium carbonate in suitable solvent such as dry methanol, dry ethanol and acetonitrile.

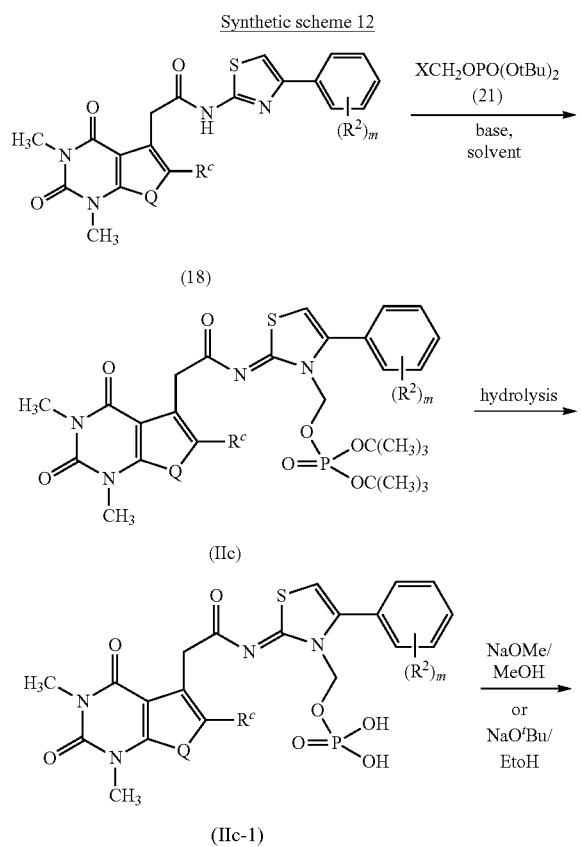

Synthetic scheme 12

(18)

(IIc)

(IIc-1)

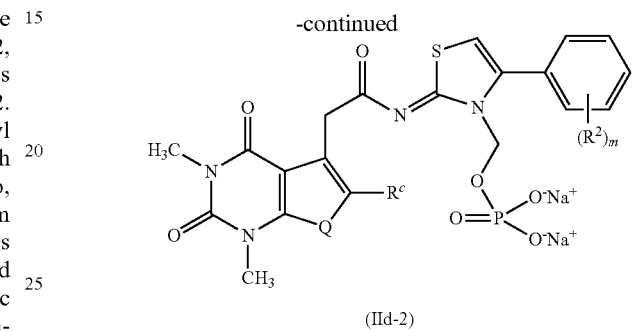

(IId-2)

An approach for the synthesis of compounds of the formula (III) wherein the heterocyclic group (Het) is pyrazolo[3,4-d] pyrimidin derivative (wherein $R^2$, $R^c$ and 'm' are as defined above, is described in synthetic scheme 13. The pyrazole compound of formula (22) or its salt is reacted with halomethyl phosphate of formula (21) (where X is chloro, bromo or iodo) in the presence of suitable base such as sodium hydride, sodium tert-butoxide or potassium tert-butoxide etc and in an appropriate solvent to give phosphono-oxymethylene derivative which undergoes hydrolysis under acidic condition or using a mixture of acetone and water to provide phosphoric acid derivative. This phosphoric acid can be converted to salt of formula (III) using appropriate equivalents of carbonates or alkoxides of alkali metals or amines in a suitable solvent. The phosphoric acid derivative can also form salts with alkaline earth metals such as calcium or magnesium under appropriate conditions.

Synthetic scheme 13

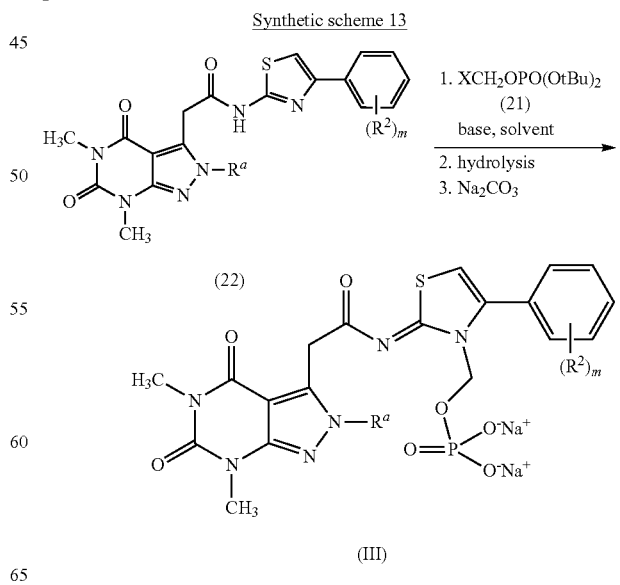

(22)

(III)

An approach for the synthesis of the compound of the invention wherein the heterocyclic group (Het) is a pyrazolo

[3,4-d]pyrimidine and the pro-moity is a phosphoric acid derivative is shown in Synthetic scheme 14. Thus, pyrazolo[3,4-d]pyrimidine acetamide (23) can be coupled with halomethyl phosphate of the formula (21) in the presence of sodium hydride in dry DMF to give N-phosphono-oxymethyl compound which can be hydrolysed under acidic condition to give phosphoric acid derivative of the formula (IV).

Synthetic scheme 14

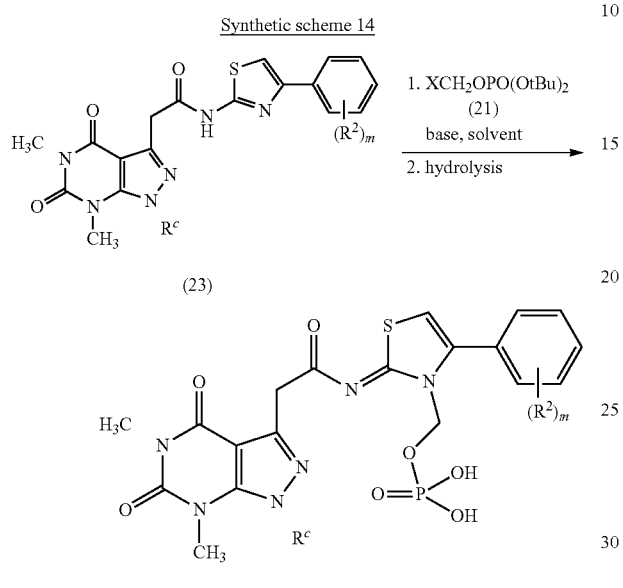

An approach for the synthesis of compound of the general formula (VI) is described in synthetic scheme 15. This thiazolo[5,4-d]pyrimidine phosphate compound is furnished by three step reaction. First the coupling reaction of thiazolo[5,4-d]pyrimidine acetamide of formula (24) or its salt with halomethyl phosphate of formula (21) (where X is iodo) in presence of suitable base such as sodium hydride, sodium tert-butoxide or potassium tert-butoxide in a suitable solvent yields the phosphono-oxymethylene intermediate This intermediate undergoes acid mediated hydrolysis to produce the phosphoric acid compound. Finally the phosphoric acid compound can be converted to its salt of formula (VI) using appropriate equivalents of carbonates or alkoxides of alkali metals or amines in a suitable solvent. The phosphoric acid derivative can also form salts with alkaline earth metals such as calcium or magnesium under appropriate conditions.

Synthetic scheme 15

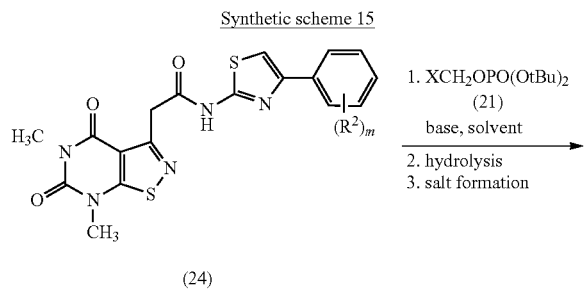

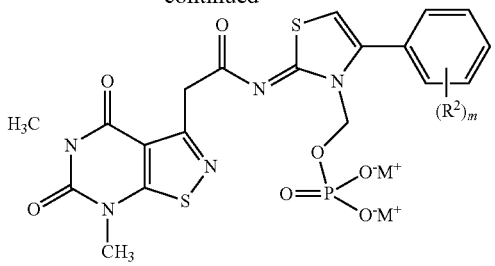

An approach for the synthesis of compounds of the general formula (VII) is described in synthetic scheme 16. Thus, purin acetamide of the formula (25) or its salt can be coupled with halomethyl phosphate of formula (21) (where X is chloro or iodo) in presence of suitable base such as sodium hydride in a suitable solvent to provide the phosphono-oxymethylene intermediate. This intermediate can be hydrolysed under acidic condition to produce the phosphoric acid compound (VII).

Synthetic scheme 16

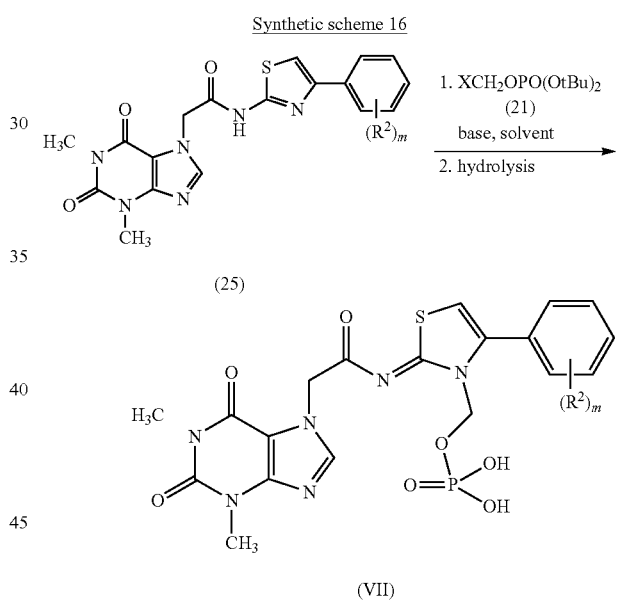

The invention is further illustrated by following non-limiting examples

EXPERIMENTAL

N-Boc-L-amino acid iodomethyl esters can be prepared by using known literature methods. Di-tert-butyl hydrogen phosphate is commercially available (Alfa Aesar). Alternatively, it can be prepared from phosphorus trichloride and tert-butanol in the presence of dry pyridine in di-isopropyl ether or diethyl ether (Goldwhite H et al., *Journal of the Chemical Society*, 1957, 2409-2412). Di-tert-butyl hydrogen phosphate can also be prepared by the reaction of phosphorus acid with tert-butanol in presence of a coupling agent such as N,N'-dicyclohexylcarbodiimide as reported by Garrlich, J. R., et al. in WO2004/89925. Di-tert-butyl phosphate is prepared by potassium permanganate oxidation of Di-tert-butyl hydrogen phosphate according to the procedure reported by Valentino, S et al. in *J. Med. Chem.* 1999, 42, 3094-3100. All the reagents and L-amino acids required for the synthesis are commercially available (Aldrich). The invention is described in greater detail by way of specific examples. However, the following examples are illustrative and are not intended to limit the broad scope of the invention. The persons skilled in the art can readily recognize a variety of non-critical parameters which can be modified or altered to yield similar results.

Unless otherwise stated, work-up includes distribution of the reaction mixture between the organic and aqueous phase indicated within parentheses, separation of layers and drying the organic layer over sodium sulphate, filtration and evaporation of the solvent. Purification, unless otherwise mentioned, includes purification by silica gel chromatographic techniques. The following abbreviations are used in the text: DMSO-$d_6$: Hexadeuterodimethyl sulfoxide; DMF: N,N-dimethylformamide, J: Coupling constant in units of Hz; RT or rt: room temperature (22-26° C.). Aq.: aqueous AcOEt: ethyl acetate; equiv. or eq.: equivalents.

INTERMEDIATES

Intermediate 1

Di-tert-butyl chloromethyl phosphate

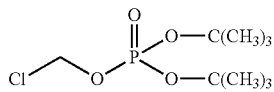

To a well stirred suspension of di-tert-butyl hydrogen phosphate (4.7 g, 22.47 mmol) in water (186 ml) was added sodium bicarbonate (7.5 g, 89.52 mmol) followed by tetra-n-butylammomium hydrogen sulphate (760 mg, 2.238 mmol). The reaction mixture was stirred at room temperature for 15 min. To the reaction mixture was added dichloromethane (112 ml) at 0° C. and it was stirred for 10 min followed by the addition of chloromethyl chlorosulphate (4.4 g, 26.85 mmol) in dichloromethane (75 ml) at same temperature. The resultant mixture was vigorously stirred overnight at room temperature. The organic layer was separated, washed with brine and evaporated under reduced pressure to yield 3.04 g of product as pale yellow oil.

Intermediate 2

Di-tert-butyl iodomethyl phosphate

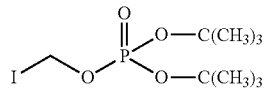

The title compound was prepared by halogen exchange reaction of di-tert-butyl chloromethyl phosphate (Intermediate 1) with sodium iodide in suitable solvent such as dry acetone or acetonitrile.

The preparation of N-Boc-L-amino acid iodomethyl ester is described below:

Step 1: To a stirred suspension of N-Boc-L-amino acid (1.0 equiv.) in water (~40 vol.) was added sodium bicarbonate (4 equiv.) followed by tetra-n-butylammomium hydrogen sulphate (0.1 equiv.) and the resultant mixture was stirred at room temperature for 15 min. To the reaction mixture was added dichloromethane (~30 vol.) and the mixture was cooled to 0° C. followed by addition of chloromethyl chlorosulphate (1.2 equiv.) at same temperature and the resulting mixture was stirred at room temperature for overnight. The organic layer was separated and collected. The aqueous layer was extracted with dichloromethane. The combined organic extract was washed with brine, dried ($Na_2SO_4$) and evaporated under reduced pressure to yield N-Boc-L-amino acid chloromethyl ester as pale yellow oil.

Step 2: To a stirred solution of step 1 intermediate (1 equiv.) in dry acetone (10 vol.) was added sodium iodide (5 equiv.) and the resultant mixture was heated to reflux for 2 h. The reaction is photosensitive hence carried out in dark room. The reaction mixture was cooled to room temperature and the precipitate was filtered. The filtrate was washed with acetone and concentrated under reduced pressure. The residue obtained was diluted with ethyl acetate, washed with saturated solution of sodium thiosulphate, water and dried ($Na_2SO_4$). The solvent was evaporated under reduced pressure to yield N-Boc-L-amino acid iodomethyl ester as a yellow liquid.

N-Boc-L-amino acid iodomethyl ester i.e Intermediates 3-9 described in Table 1 were prepared as per the procedure described above.

TABLE 1

Structure, name and $^1$H-NMR data of N-Boc-L-amino acid iodomethyl esters

| Sr. No. | Structure and Intermediate No. | Chemical name and $^1$H-NMR data |
|---|---|---|
| 1. | Intermediate 3 | Iodomethyl [(tert-butoxycarbonyl)amino]acetate: $^1$H NMR (300 MHz, $CDCl_3$): δ 1.45 (s, 9H), 3.90-3.96 (m, 2H), 5.00 (br s, 1H), 5.95 (s, 2H). |
| 2. | Intermediate 4 | (S)-Iodomethyl 2-((tert-butoxycarbonyl)amino)propanoate: $^1$H NMR (300 MHz, $CDCl_3$): δ 1.22-1.30 (m, 3H), 1.45 (br s, 9H), 4.30-4.38 (m, 1H), 5.01-5.08 (m, 1H), 5.86-6.02 (m, 2H). |

TABLE 1-continued

Structure, name and ¹H-NMR data of N-Boc-L-amino acid iodomethyl esters

| Sr. No. | Structure and Intermediate No. | Chemical name and ¹H-NMR data |
|---|---|---|
| 3. | Intermediate 5 | (S)-Iodomethyl 2-((tert-butoxycarbonyl)amino)-3-methyl butanoate:<br>¹H NMR (300 MHz, CDCl$_3$): δ 0.92 (d, J = 6.9 Hz, 3H), 0.99 (d, J = 6.9 Hz, 3H), 1.45 (s, 9H), 2.13-2.20 (m, 1H), 4.15-4.24 (m, 1H), 4.95-5.02 (m, 1H), 5.84 (d, J = 3.9 Hz, 1H), 6.04 (d, J = 4.5 Hz, 1H). |
| 4. | Intermediate 6 | (2S,3S)-Iodomethyl 2-((tert-butoxycarbonyl)amino)-3-methylpentanoate:<br>¹H NMR (300 MHz, CDCl$_3$): δ 0.86-0.98 (m, 6H), 1.45 (br s, 9H), 1.89-1.96 (m, 2H), 4.26-4.33 (m, 1H), 5.06 (d, J = 8.7 Hz, 1H), 6.18 (br s, 2H), 9.41 (br s, 1H). |
| 5. | Intermediate 7 | (S)-1-tert-Butyl 2-(iodomethyl) pyrrolidine-1,2-dicarboxylate:<br>¹H NMR (300 MHz, CDCl$_3$): δ 1.46 (br s, 9H), 1.88-2.26 (m, 4H), 3.37-3.55 (m, 2H), 4.11-4.34 (m, 1H), 5.83 (d, J = 4.5 Hz, 1H), 6.06 (d, J = 4.5 Hz, 1H). |
| 6. | Intermediate 8 | 1-tert-Butyl 4-(iodomethyl) piperidine-1,4-dicarboxylate:<br>¹H NMR (300 MHz, CDCl$_3$): δ 1.45 (s, 9H), 1.62-1.70 (m, 2H), 1.85-1.95 (m, 2H), 2.43-2.53 (m, 1H), 2.83-2.90 (m, 2H), 4.00-4.11 (m, 2H), 5.93 (s, 1H). |
| 7. | Intermediate 9 | (S)-Iodomethyl 2-((tert-butoxycarbonyl)amino)-3-phenyl propanoate:<br>¹H NMR (300 MHz, CDCl$_3$): δ 1.40 (s, 9H), 2.98-3.16 (m, 2H), 4.54-4.62 (m, 1H), 4.88-4.95 (m, 1H), 5.86 (d, J = 4.8 Hz, 1H), 5.99 (d, J = 4.2 Hz, 1H), 7.17 (d, J = 6.3 Hz, 2H), 7.25-7.33 (m, 3H). |

Intermediate 10

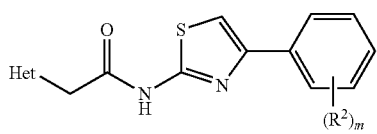

The 2-Amino-4 aryl thiazole acetamides of the above formula were prepared by coupling the desired heterocyclic acid with 2-Amino-4-aryl thiazole derivative according to procedure described in the PCT applications WO2010109287, WO2010109328, WO2010109329, WO2010109334, WO2009118596, WO2009144548, WO2010004390, WO2010125469, WO2011114184, WO2011132017, WO2007073505, WO2010075353, WO2009158719, WO2009002933 and WO2010132838.

The present patent application is described in greater detail by way of specific examples. However, the following examples are illustrative and are not intended to limit the broad scope of the present patent application. The following examples are prepared from the approaches described in synthetic schemes using the intermediates 1-10 discussed above.

EXAMPLES

General Procedure for the Preparation of Amino Acid Derivatives

Step 1: To a stirred solution of 2-amino-4 aryl thiazole acetamide derivative (1 equiv.) in dry DMF (10 vol.), sodium hydride (60% dispersion in mineral oil, 1.2 equiv.) was added and resultant mixture was stirred for 1 h at room temperature.

The reaction mixture was cooled in ice bath and appropriate N-Boc-L-amino acid iodomethyl ester (3.5 equiv.) was added in portions. The reaction mixture was stirred at room temperature overnight. The reaction mixture was diluted with water and the precipitated solid was collected by filtration. The solid was further purified by silica gel column chromatography to yield product as a pale yellow solid.

Step 2: To a stirred suspension of Step 1 intermediate (1 equiv.) in dry ethyl acetate (~10 vol.) was added saturated solution of hydrochloric acid in dry ethyl acetate (~20 vol.) at 0-5° C. The reaction mixture was gently warmed to room temperature and stirred overnight. The solvent was evaporated under reduced pressure. The solid obtained was stirred in dry ethyl acetate for 30 min, filtered, washed with ethyl acetate and dried to yield product as a white solid.

General Procedure for the Preparation of Phosphate Derivatives

The required phosphate esters were prepared by three different approaches as described below Method A: Using sodium hydride and iodomethyl di-tert-butyl phosphate To a stirred suspension of 2-amino-4 aryl thiazole acetamide derivative (1 equiv.) in dry DMF (6 vol.) was added sodium hydride (60% dispersion in mineral oil, 1.5 equiv.) and the resultant mixture was stirred at room temperature for 1 h. The reaction mixture was cooled at 0° C. and a solution of freshly prepared iodomethyl di-tert-butyl phosphate (3.5 equiv.) in dry DMF (4 vol.) was added drop wise and stirred for 10 min. The cooling bath was removed and the reaction mixture was stirred at room temperature for 3 h. The reaction mixture was diluted with water and extracted with ethyl acetate. The organic layer was washed with water, dried over $Na_2SO_4$ and concentrated under reduced pressure. The viscous residue was washed with hexane to remove traces of the reagent. The residue was stirred in diethyl ether. The precipitated solid was filtered and dried to yield product as an off-white solid.

Method B: Using sodium tert-butoxide and iodomethyl di-tert-butyl phosphate

Step 1: Sodium salt preparation: To a stirred solution of 2-amino-4 aryl thiazole acetamide derivative (1 eqiuv.) in ethanol (10 vol.), sodium tert-butoxide solution (1.1 equiv.) in dry THF or dry ethanol (1 vol.) was added at 0° C. The reaction mixture was stirred for 1 h at room temperature. The reaction mixture was diluted with n-pentane or hexane (30 vol.) and was further stirred for 1 h at room temperature. The solid was collected by filtration to get desired salt.

Step 2: To a stirred suspension of Step 1 intermediate (1 equiv.) in dry DMF or dry acetone (5 vol.) was added iodo methyl di-tert-butyl phosphate (1.5 equiv.) in dry acetone or dry DMF (5 vol.) at 0-5° C. and the reaction mixture was stirred at room temperature for 2 h. The reaction mixture was filtered through hyflo bed. The filtrate was concentrated under reduced pressure to give a residue. The residue was diluted with ethyl acetate, washed with water and dried over $Na_2SO_4$. The solvent was evaporated under reduced pressure and viscous residue obtained was washed with hexane to remove traces of the reagent. The residue was then stirred in diethyl ether or methyl tert-butyl ether or di-isopropyl ether and the solid precipitated out was filtered and dried to yield product as an off-white solid.

Method C: Using sodium tert-butoxide and chloromethyl di-tert-butyl phosphate

To a stirred suspension of sodium salt of 2-amino-4 aryl thiazole acetamide derivative Step 1 intermediate of method B (1 equiv.) in dry acetone or dry DMF (25 vol.) was added chloromethyl di-tert-butyl phosphate (2.5 equiv.) in dry acetone or dry DMF (2 vol.) followed by sodium iodide (1 equiv.) at 0-5° C. and the reaction mixture was stirred for 40 h at room temperature. The reaction mixture was filtered through hyflow bed. The filtrate was concentrated under reduced pressure to give a residue. The residue was treated with diethyl ether or methyl tert-butyl ether to obtain product as a pale yellow solid.

General Procedure for the Hydrolysis of Phosphate Esters

The di-tert-butyl phosphate esters were hydrolysed to the free phosphoric acid derivatives by two methods as described below Method A: Using trifluoroacetic acid To a stirred suspension of di-tert-butyl phosphonate intermediate of 2-amino-4 aryl thiazole acetamide derivative (1 equiv.) in dry dichloromethane (20 vol.) was added trifluoroacetic acid (3 equiv.) at 0° C. The reaction mixture was gently warmed to room temperature and stirred overnight. The solid precipitated out was diluted with dichloromethane and collected by filteration, washed with dichloromethane and dried to yield product as a white solid.

Method B: By refluxing in aqueous acetone

A mixture of di-tert-butyl phosphonate intermediate of 2-amino-4 aryl thiazole acetamide derivative (1 equiv.), acetone (~30 vol.) and water (~30 vol.) was stirred at 60-65° C. for 12 h. The solution was cooled to room temperature and filtered. The filtrate was concentrated to slurry volume. The solid was filtered and washed with ethyl acetate to give product as an off white solid.

General Procedure for Disodium Phosphonate Salts

This can be achieved by three methods viz. Method A, Method B and Method C. Details procedure are described as below Method A: Using sodium methoxide Sodium methoxide was freshly prepared from sodium metal (2 equiv.) and dry methanol (20 vol.). To this solution diphosphonate intermediate of 2-amino-4 aryl thiazole acetamide derivative (1 equiv.) was added at 0-5° C. and further stirred at room temperature for 2 h. The solvent was evaporated under reduced pressure. The solid obtained was filtered and dissolved in water. The reaction mixture was stirred for about 1 h at 25-30° C. and filtered through celite. The filtrate was concentrated under reduced pressure at about 23-25° C. to obtain a solid residue. Acetone was added in the residue and stirred for 15-20 min at room temperature. The precipitated product was collected by filtration to obtain as an off white solid.

Method B: Using sodium carbonate

To a stirred suspension of diphosphonate intermediate of 2-amino-4 aryl thiazole acetamide derivative (1 equiv.) in acetonitrile (80 vol.) and water (50 vol.), sodium carbonate (1 equiv.) was added and the resulting mixture was stirred at room temperature for 2 h. Solvents were evaporated completely from the reaction mixture under reduced pressure. The solid obtained was dissolved in water. The reaction mixture was stirred for about 1 h at 25-30° C. and filtered through celite. The filtrate was concentrated under reduced pressure at about 23-25° C. to obtain a solid residue. Acetone was added in the residue and stirred for 15-20 min at room temperature. The precipitated product was collected by filtration to obtain as an off white solid.

Method C: Using sodium tert-butoxide

To a stirred solution of diphosphonate intermediate of 2-amino-4 aryl thiazole acetamide derivative (1 equiv.) in dry methanol (25 vol.) was added sodium tert-butoxide (2.5 equiv.) in methanol (~10 vol.) at 0-5° C. and the resulting mixture was stirred at room temperature for 90 min. The solid obtained was filtered and dissolved in water. The reaction mixture was stirred for about 1 h at 25-30° C. and filtered through celite. The filtrate was concentrated under reduced pressure at about 23-25° C. to obtain a solid residue. Acetone was added in the residue and stirred for 15-20 min at room temperature. The precipitated product was collected by filtration to obtain as an off white solid.

Example 1

[2-{[(1,3-Dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3 (2H)-yl]methyl-2-methyl propanoate

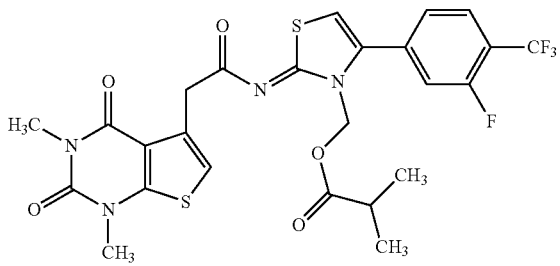 [SMILES: CC(C)C(=O)OCn1c(-c2ccc(C(F)(F)F)c(F)c2)cs/c1=N\C(=O)Cc1csc2c1c(=O)n(C)c(=O)n2C]

To a stirred solution of 2-(1,3-dimethyl-2,4-dioxo-1,2,3,4-tetrahydrothieno[2,3-d]pyrimidin-5-yl)-N-{4-[3-fluoro-4-(trifluoromethyl)phenyl]-1,3-thiazol-2-yl}acetamide (200 mg, 0.40 mmol) in dry DMF (2.0 ml), sodium hydride (60% dispersion in mineral oil, 19.2 mg, 0.48 mmol) was added and after stirring for 1 h at room temperature and cooled in ice bath, iodomethyl 2-methylpropanoate (319 mg, 1.40 mmol) was added slowly. The reaction was then stirred at room temperature for overnight. The mixture was diluted with water (10 ml) and the precipitated solid was collected by filtration. The crude solid was further purified by silica gel column chromatography using pet ether-ethyl acetate (70:30) to yield 65 mg of product as a pale yellow solid; $^1$H NMR (300 MHz, CDCl$_3$): δ 1.20 (d, J=6.0 Hz, 6H), 2.58-2.69 (m, 1H), 3.34 (s, 3H), 3.56 (s, 3H), 4.37 (s, 2H), 6.51 (s, 2H), 6.78 (s, 1H), 7.34 (s, 1H), 7.62 (t, J=6.0 Hz, 1H), 7.70-7.75 (m, 2H); ESI (m/z): 598.89 (M+H)$^+$.

Example 2

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl-2-methylpropanoate

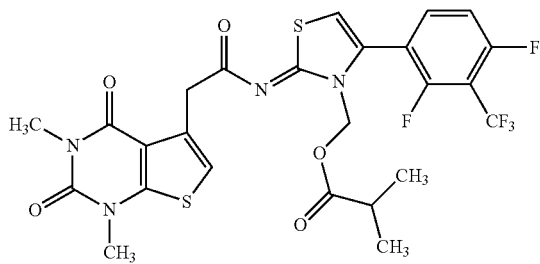 [SMILES: CC(C)C(=O)OCn1c(-c2ccc(F)c(C(F)(F)F)c2F)cs/c1=N\C(=O)Cc1csc2c1c(=O)n(C)c(=O)n2C]

The title compound was prepared by the reaction of 2-(1,3-dimethyl-2,4-dioxo-1,2,3,4-tetrahydrothieno[2,3-d]pyrimidin-5-yl)-N-{4-[3-fluoro-4-(trifluoromethyl)phenyl]-1,3-thiazol-2-yl}acetamide (300 mg, 0.58 mmol) with iodomethyl 2-methylpropanoate (462 mg, 2.03 mmol) in the presence of sodium hydride (60% dispersion in mineral oil, 27.9 mg, 0.69 mmol) in dry DMF (3.0 ml) according to procedure described for Example 1 to give 150 mg of title compound as a white solid; $^1$H NMR (300 MHz, CDCl$_3$): δ 1.19 (d, J=6.0 Hz, 6H), 2.58-2.69 (m, 1H), 3.35 (s, 3H), 3.57 (s, 3H), 4.38 (s, 2H), 6.51 (s, 2H), 6.79 (s, 1H), 7.10 (t, J=8.9 Hz, 1H), 7.49 (s, 1H), 8.39 (q, J=9.0 Hz, 1H); ESI (m/z): 616.88 (M+H)$^+$.

Example 3

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl glycinate hydrochloride

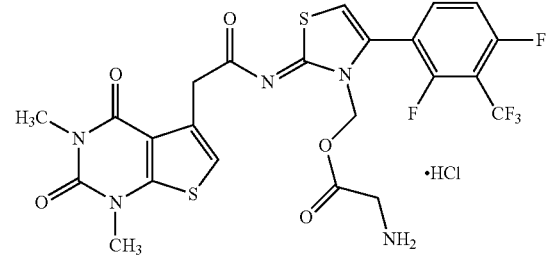 [SMILES: Cn1c(=O)c2c(CC(=O)/N=c3\scc(-c4ccc(F)c(C(F)(F)F)c4F)n3COC(=O)CN)csc2n(C)c1=O ; Cl]

Step 1: [4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl N-(tert-butoxycarbonyl)glycinate: The title compound was prepared by the reaction of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide (750 mg, 1.453 mmol) with intermediate 3 (1.6 g, 5.087 mmol) using sodium hydride (60% dispersion in mineral oil, 69.74 mg, 1.743 mmol) in dry DMF (7.5 ml) according to the step 1 of general procedure described for the preparation of amino acid derivatives to yield 260 mg of product as an off-white solid; $^1$H NMR (300 MHz, DMSO-d$_6$): δ 1.33 (br s, 9H), 3.18 (s, 3H), 3.48 (s, 3H), 3.78 (d, J=6.0 Hz, 2H), 4.39 (br s, 2H), 6.53 (s, 2H), 7.10 (s, 1H), 7.31 (t, J=9.0 Hz, 1H), 7.49 (t, J=9.0 Hz, 1H), 7.76 (br s, 1H), 8.43 (q, J=9.0 Hz, 1H); ESI (m/z): 703.87 (M+H)$^+$.

Step 2: [4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl glycinate hydrochloride: The title compound was prepared by the reaction of Step 1 intermediate (245 mg, 0.348 mmol) in dry ethyl acetate (5 ml) and saturated solution of hydrochloric acid in dry ethyl acetate (5 ml) according to step 2 of general procedure described for the preparation of amino acid derivatives to yield 190 mg of product as a white solid. $^1$H NMR (300 MHz, DMSO-d$_6$): δ 3.18 (s, 3H), 3.49 (s, 3H), 3.95 (br s, 2H), 4.44 (s, 2H), 6.65 (br s, 2H), 7.14 (s, 1H), 7.53 (t, J=9.0 Hz, 1H), 7.77 (br s, 1H), 8.36-8.49 (m, 3H); ESI (m/z): 603.89 (M+H)$^+$.

Example 4

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl L-alaninate hydrochloride

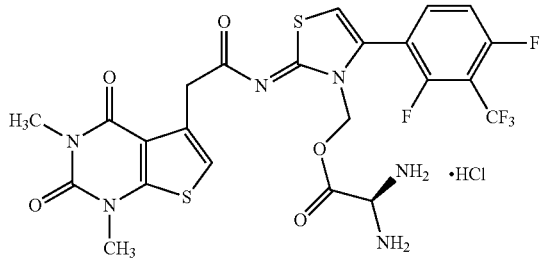

Step 1: [4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl N-(tert-butoxycarbonyl)-L-alaninate: The title compound was prepared by the reaction of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide (1.0 g, 1.937 mmol) with intermediate 4 (2.2 g, 6.782 mmol) in the presence of sodium hydride (60% dispersion in mineral oil, 93.74 mg, 2.3255 mmol) in dry DMF (10.0 ml) according to step 1 of general procedure described for the preparation of amino acid derivatives to give 160 mg of product as an white solid; $^1$H NMR (300 MHz, DMSO-$d_6$): δ 1.23 (s, 3H), 1.30 (s, 9H), 3.18 (s, 3H), 3.48 (s, 3H), 4.03-4.09 (m, 1H), 4.38 (s, 2H), 6.43-6.59 (m, 2H), 7.10 (s, 1H), 7.37 (d, J=6.0 Hz, 1H), 7.50 (t, J=9.0 Hz, 1H), 7.76 (s, 1H), 8.44 (q, J=9.0 Hz, 1H); APCI (m/z): 717.86 (M+H)$^+$.

Step 2: [4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl L-alaninate hydrochloride: The title compound was prepared by hydrolysis of Step 1 intermediate (155 mg, 0.220 mmol) with saturated solution of hydrochloride in dry ethyl acetate (5.0 ml) according to step 2 of general procedure described for the preparation of amino acid derivatives to yield 105 mg of product as white solid; $^1$H NMR (300 MHz, DMSO-$d_6$): δ 1.43 (d, J=6.0 Hz, 3H), 3.18 (s, 3H), 3.49 (s, 3H), 4.20-4.27 (m, 1H), 4.44 (s, 2H), 6.58-6.67 (m, 2H), 7.14 (s, 1H), 7.53 (t, J=9.0 Hz, 1H), 7.77 (s, 1H), 8.37-8.55 (m, 4H); ESI (m/z): 617.88 (M+H)$^+$.

Example 5

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl L-valinate hydrochloride

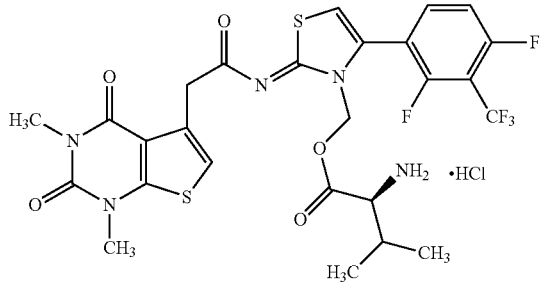 [SMILES: CC(C)[C@H](N)C(=O)OCn1c(-c2ccc(F)c(C(F)(F)F)c2F)cs/c1=N\C(=O)Cc1csc2c1c(=O)n(C)c(=O)n2C ; Cl]

Step 1: [4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl N-(tert-butoxycarbonyl)-L-valinate: The title compound was prepared by coupling reaction of N-{4-[2,4-difluoro-3-(trifluoromethyl)phenyl]-1,3-thiazol-2-yl}-2-(1,3-dimethyl-2,4-dioxo-1,2,3,4-tetrahydro thieno[2,3-d]pyrimidin-5-yl)acetamide (750 mg, 1.453 mmol) with intermediate 5 (1.8 g, 5.087 mmol) using sodium hydride (60% dispersion in mineral oil, 69.60 mg, 1.744 mmol) in dry DMF (7.5 ml) according to step 1 of general procedure described for the preparation of amino acid derivatives to yield 240 mg of product as an off-white solid; $^1$H NMR (300 MHz, DMSO-$d_6$): δ 0.82 (d, J=6.0 Hz, 6H), 1.22-1.34 (m, 9H), 1.96-2.08 (m, 1H), 3.18 (br s, 3H), 3.48 (s, 3H), 3.87-4.07 (m, 1H), 4.40 (s, 2H), 6.46-6.55 (m, 2H), 7.11 (s, 1H), 7.21 (d, J=6.0 Hz, 1H), 7.50 (t, J=8.7 Hz, 1H), 7.75 (s, 1H), 8.42 (q, J=9.0 Hz, 1H); ESI (m/z): 743.88 (M−H)$^-$.

Step 2: [4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl L-valinate hydrochloride: The title compound was prepared by deprotection of Step 1 intermediate (150 mg, 0.201 mmol) using saturated solution of hydrochloride in dry ethyl acetate (5 ml) according to step 2 of general procedure described for the preparation of amino acid derivatives to yield 90 mg of product as an off-white solid; $^1$H NMR (300 MHz, DMSO-$d_6$): δ 0.91 (d, J=6.0 Hz, 6H), 2.17-2.24 (m, 1H), 3.18 (s, 3H), 3.49 (s, 3H), 4.03 (br s, 1H), 4.46 (s, 2H), 6.63 (br s, 2H), 7.14 (s, 1H), 7.53 (t, J=9.6 Hz, 1H), 7.79 (s, 1H), 8.40-8.50 (m, 4H); ESI (m/z): 645.91 (M+H)$^+$.

Example 6

[2-{[(1,3-Dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methyl L-isoleucinate hydrochloride

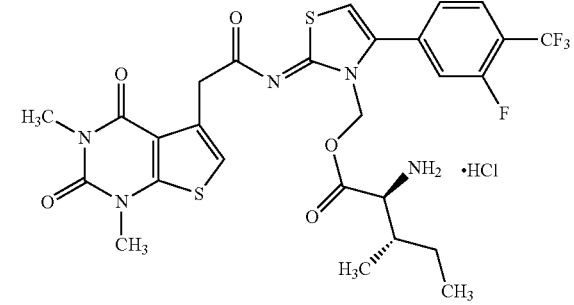 [SMILES: CC[C@H](C)[C@H](N)C(=O)OCn1c(-c2ccc(C(F)(F)F)c(F)c2)cs/c1=N\C(=O)Cc1csc2c1c(=O)n(C)c(=O)n2C ; Cl]

Step 1: [2-{[(1,3-Dimethyl-2,4-dioxo-1,2,3,4-tetrahydrothieno[2,3-d]pyrimidin-5-yl) acetyl]imino}-4-[3-fluoro-4-(trifluoromethyl)phenyl]-1,3-thiazol-3 (2H)-yl]methyl N-(tert-butoxycarbonyl)-L-isoleucinate: The title compound was prepared by coupling reaction of 2-(1,3-dimethyl-2,4-dioxo-1,2,3,4-tetrahydrothieno[2,3-d]pyrimidin-5-yl)-N-{4-[3-fluoro-4-(trifluoromethyl)phenyl]-1,3-thiazol-2-yl}acetamide (300 mg, 0.6024 mmol) with intermediate 6 (3.5 g, 2.108 mmol) using sodium hydride (60% dispersion in mineral oil, 36.14 mg, 0.903 mmol) in dry DMF (3.5 ml) according to step 1 of general procedure described for the preparation of amino acid derivatives to yield 38.5 mg of product as an off-white solid; $^1$H NMR (300 MHz, DMSO-$d_6$): δ 0.61 (t, J=7.2 Hz, 3H), 0.76 (d, J=6.9 Hz, 3H), 1.05-1.30 (m, 2H), 1.28 (s, 9H), 1.65-1.79 (m, 1H), 3.17 (s, 3H), 3.46 (s, 3H), 3.96 (t, J=6.9 Hz, 1H), 4.40 (s, 2H), 6.46-6.53 (m, 2H), 7.09 (s, 1H), 7.18 (d, J=9.0 Hz, 1H), 7.82 (t, J=7.8 Hz, 1H), 7.92-8.02 (m, 2H), 8.08 (s, 1H).

Step 2: [2-{[(1,3-Dimethyl-2,4-dioxo-1,2,3,4-tetrahydrothieno[2,3-d]pyrimidin-5-yl) acetyl]imino}-4-[3-fluoro- 4-(trifluoromethyl)phenyl]-1,3-thiazol-3(2H)-yl]methyl L-isoleucinate hydrochloride: The title compound was prepared by deprotection of Step 1 intermediate (35 mg) with saturated solution of hydrochloride in dry ethyl acetate (3 ml) according to step 2 of general procedure described for the preparation of amino acid derivatives to yield 20 mg of product as an off-white solid; $^1$H NMR (300 MHz, DMSO-$d_6$): δ 0.69 (t, J=6.6 Hz, 3H), 0.86 (t, J=6.6 Hz, 3H), 1.15-1.23 (m, 1H), 1.33-1.41 (m, 1H), 1.87-1.94 (m, 1H), 3.18 (s, 3H), 3.48 (s, 3H), 4.11 (br s, 1H), 4.46 (br s, 2H), 6.58-6.68 (m, 2H), 7.12 (s, 1H), 7.85 (t, J=7.8 Hz, 1H), 7.94-8.06 (m, 2H), 8.13 (s, 1H), 8.39 (br s, 3H); ESI (m/z): 642.03 (M+H)$^+$.

Example 7

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl L-isoleucinate hydrochloride

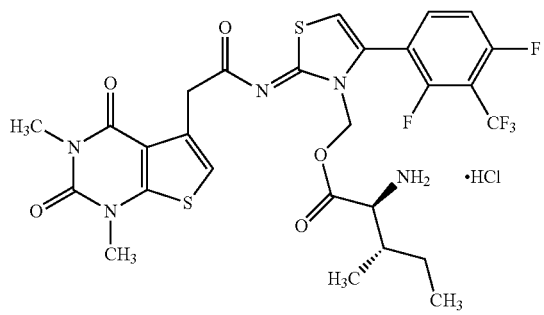

Step 1: [4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl N-(tert-butoxycarbonyl -L-isoleucinate: The title compound was prepared by coupling N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide (1 g, 1.937 mmol) with intermediate 6 (2.4 g, 6.782 mmol) using sodium hydride (60% dispersion in mineral oil, 93 mg, 2.324 mmol) in dry DMF (10.0 ml) according to step 1 of general procedure described for the preparation of amino acid derivatives to yield 603 mg of product as an off-white solid; $^1$H NMR (300 MHz, CDCl$_3$): δ 0.72 (t, J=7.5 Hz, 3H), 0.87 (d, J=6.6 Hz, 3H), 0.92-1.00 (m, 1H), 1.38 (s, 9H), 1.45 (s, 2H), 1.83 (br s, 2H), 3.35 (s, 3H), 3.57 (s, 3H), 4.27-4.49 (m, 2H), 5.24 (d, J=9.0, 1H), 6.47-6.52 (m, 1H), 6.81 (s, 1H), 7.09 (t, J=9.0 Hz, 1H), 7.48 (s, 1H), 8.38 (q, J=9.0 Hz, 1H); ESI (m/z): 757.76 (M–H)$^-$.

Step 2: [4-[2,4-Difluoro-3-(trifluoromethyl)phenyl]-2-{[(1,3-dimethyl-2,4-dioxo-1,2,3,4-tetrahydrothieno[2,3-d] pyrimidin-5-yl)acetyl]imino}-1,3-thiazol-3 (2H)-yl]methyl L-isoleucinate hydrochloride: The title compound was prepared by hydrolysis of Step 1 intermediate (600 mg, 0.790 mmol) with saturated solution of hydrochloride in dry ethyl acetate (15.0 ml) according to step 2 of general procedure described for the preparation of amino acid derivatives to yield 430 mg of product as an off-white solid; $^1$H NMR (300 MHz, DMSO-$d_6$): δ 0.70 (t, J=6.0 Hz, 3H), 0.86 (d, J=6.0 Hz, 3H), 1.16-1.23 (m, 1H), 1.32-1.39 (m, 1H), 1.91-1.98 (m, 1H), 3.18 (s, 3H), 3.48 (s, 3H), 4.06 (s, 1H), 4.46 (br s, 1H), 6.61 (br s, 2H), 7.14 (s, 1H), 7.53 (t, J=9.0 Hz, 1H), 7.78 (s, 1H), 8.28-8.56 (m, 4H); ESI (m/z): 659.54 (M)$^+$.

Example 8

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl L-prolinate hydrochloride

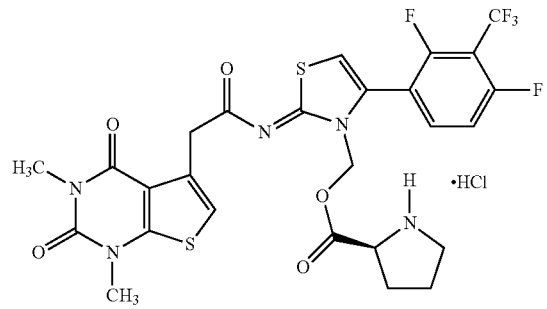 [SMILES: Cn1c(=O)c2c(CC(=O)/N=c3\scc(-c4ccc(F)c(C(F)(F)F)c4F)n3COC(=O)[C@@H]3CCCN3)csc2n(C)c1=O ; Cl]

Step 1: 1-tert-Butyl 2-{[4-[2,4-difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl}(2S)-pyrrolidine-1,2-dicarboxylate: The title compound was prepared by coupling N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl) acetamide (1.0 g, 1.937 mmol) with intermediate 7 (2.4 g, 6.782 mmol) in the presence of sodium hydride (60% dispersion in mineral oil, 116.20 mg, 2.905 mmol) in dry DMF (25 ml) according to step 1 of general procedure described for the preparation of amino acid derivatives to give 190 mg of product as an off-white solid; $^1$H NMR (300 MHz, DMSO-$d_6$): δ 1.19 (s, 9H), 1.73-1.27 (m, 4H), 3.14-3.20 (s, 5H), 3.48 (s, 3H), 4.19-4.26 (m, 1H), 4.40 (s, 2H), 6.49-6.56 (m, 2H), 7.11 (s, 1H), 7.56 (q, J=9.0 Hz, 1H), 7.76 (s, 1H), 8.39-8.41 (m, 1H); APCI (m/z): 743.86 (M+H)$^+$.

Step 2: [4-[2,4-Difluoro-3-(trifluoromethyl)phenyl]-2-{[(1,3-dimethyl-2,4-dioxo-1,2,3,4-tetrahydrothieno[2,3-d] pyrimidin-5-yl)acetyl]imino}-1,3-thiazol-3(2H)-yl]methyl L-prolinate Hydrochloride: The title compound was prepared by hydrolysis of Step 1 intermediate (180 mg, 0.242 mmol) with saturated solution of hydrochloride in dry ethyl acetate (5.0 ml) according to step 2 of general procedure described for the preparation of amino acid derivatives to yield 101 mg of product as white solid; $^1$HNMR (300 MHz, DMSO-$d_6$): δ 1.81-1.89 (m, 2H), 1.99-2.09 (m, 1H), 2.17-2.29 (m, 1H), 2.71-2.83 (m, 5H), 3.47 (s, 3H), 4.43 (s, 2H), 4.50 (t, J=7.8 Hz, 1H), 6.60 (s, 2H), 7.12 (s, 1H), 7.52 (t, J=9.9 Hz, 1H), 7.77 (s, 1H), 8.39 (q, J=8.4 Hz, 1H), 9.04 (br s, 1H), 9.75 (br s, 1H); APCI (m/z): 643.98 (M+H)$^+$.

Example 9

[2-{[(1,3-Dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methylpiperidine-4-carboxylate hydrochloride

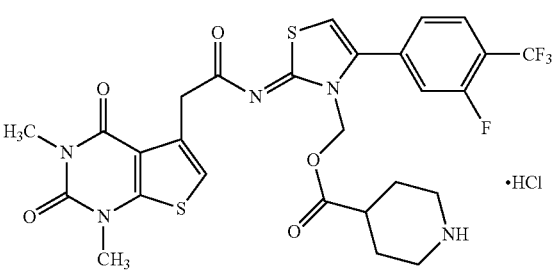 [SMILES: Cn1c(=O)c2c(CC(=O)/N=c3\scc(-c4ccc(C(F)(F)F)c(F)c4)n3COC(=O)C3CCNCC3)csc2n(C)c1=O ; Cl]

Step 1: 1-tert-Butyl 4-{[2-{[(1,3-dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3 (2H)-yl]methyl}piperidine-1,4-dicarboxylate: The title compound was prepared by coupling 2-(1,3-dimethyl-2,4-dioxo-1,2,3,4-tetrahydrothieno[2,3-d]pyrimidin-5-yl)-N-{4-[3-fluoro-4-(trifluoromethyl)phenyl]-1,3-thiazol-2-yl}acetamide (500 mg, 1.003 mmol) with intermediate 8 (1.3 g, 3.51 mmol) using sodium hydride (60% dispersion in mineral oil, 44.13 mg, 1.10 mmol) in dry DMF (5.0 ml) according to step 1 of general procedure described for the preparation of amino acid derivatives to yield 250 mg of product as an off-white solid; $^1$H NMR (300 MHz, DMSO-d$_6$): δ 1.43 (s, 9H), 1.65-1.73 (m, 2H), 1.87-1.95 (m, 2H), 2.50-2.59 (m, 1H), 2.81 (t, J=12.0 Hz, 2H), 3.34 (s, 3H), 3.57 (s, 3H), 3.95-4.02 (m, 2H), 4.36 (s, 2H), 6.53 (s, 2H), 6.78 (s, 1H), 7.35 (s, 1H), 7.62 (t, J=9.0 Hz, 1H), 7.71 (d, J=9.0 Hz, 2H); ESI (m/z): 739.76 (M+H)$^+$.

Step 2: [2-{[(1,3-Dimethyl-2,4-dioxo-1,2,3,4-tetrahydrothieno[2,3-d]pyrimidin-5-yl) acetyl]imino}-4-[3-fluoro-4-(trifluoromethyl)phenyl]-1,3-thiazol-3(2H)-yl]methyl piperidine-4-carboxylate hydrochloride: The title compound was prepared by the reaction of Step 1 intermediate (240 mg, 0.325 mmol) with saturated solution of hydrochloride in dry ethyl acetate (5.0 ml) in ethyl acetate (3.0 ml) according to step 2 of general procedure described for the preparation of amino acid derivatives to yield 160 mg of product as an off-white solid; $^1$H NMR (300 MHz, DMSO-d$_6$): δ 1.71-1.85 (m, 2H), 1.95-2.08 (m, 2H), 2.78-2.93 (m, 4H), 3.16 (br s, 4H), 3.47 (s, 3H), 4.39 (s, 2H), 6.49 (br s, 2H), 7.11 (s, 1H), 7.83-8.04 (m, 3H), 8.10 (s, 1H), 8.47-8.69 (m, 2H); ESI (m/z): 639.97 (M+H)$^+$.

Example 10

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl piperidine-4-carboxylate hydrochloride

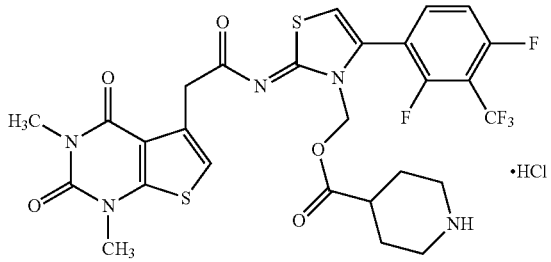 [SMILES: Cn1c(=O)c2c(CC(=O)/N=c3\scc(-c4ccc(F)c(C(F)(F)F)c4F)n3COC(=O)C3CCNCC3)csc2n(C)c1=O ; Cl]

Step 1: 1-tert-Butyl 4-{[4-[2,4-difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl}piperidine-1,4-dicarboxylate: The title compound was prepared by coupling of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide (2.50 g, 4.844 mmol) with intermediate 8 (6.30 g, 16.954 mmol) in the presence of sodium hydride (60% dispersion in mineral oil, 232 mg, 5.813 mmol) in dry DMF (25 ml) according to step 1 of general procedure described for the preparation of amino acid derivatives to yield 1.169 g of product as an off-white solid; $^1$H NMR (300 MHz, DMSO-d$_6$): δ 1.43 (s, 9H), 1.62-1.70 (m, 2H), 1.84-1.93 (m, 2H), 2.51-2.60 (m, 1H), 2.80 (t, J=11.7 Hz, 2H), 3.34 (s, 3H), 3.57 (s, 3H), 3.95-4.03 (m, 2H), 4.36 (s, 2H), 6.53 (s, 2H), 6.79 (s, 1H), 7.10 (t, J=9.0 Hz, 1H), 7.49 (s, 1H), 8.36 (q, J=9.0 Hz, 1H); ESI (m/z): 757.81 (M+H)$^+$.

Step 2: [4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl piperidine-4-carboxylate hydrochloride: The title compound was prepared by hydrolysis of Step 1 intermediate (1.15 g, 1.519 mmol) using saturated solution of hydrochloric acid in dry ethyl acetate (40 ml) in dry ethyl acetate (7 ml) according to step 2 of general procedure described for the preparation of amino acid derivatives to yield 955 mg of product as a white solid; $^1$H NMR (300 MHz, DMSO-d$_6$): δ 1.72-1.82 (m, 2H), 1.96-2.04 (m, 2H), 2.84-2.94 (m, 4H), 3.17 (br s, 4H), 3.48 (s, 3H), 4.41 (s, 2H), 6.49 (br s, 2H), 7.12 (s, 1H), 7.55 (t, J=9.0 Hz, 1H), 7.76 (s, 1H), 8.34-8.41 (m, 1H), 8.62-8.70 (m, 1H), 8.83-8.92 (m, 1H); APCI (m/z): 657.93 (M+H)$^+$.

Example 11

[2-{[(1,3-Dimethyl-2,4-dioxo-1,2,3,4-tetrahydrothieno[2,3-d]pyrimidin-5-yl) acetyl]imino}-4-[3-fluoro-4-(trifluoromethyl)phenyl]-1,3-thiazol-3 (2H)-yl]methyl dihydrogen phosphate

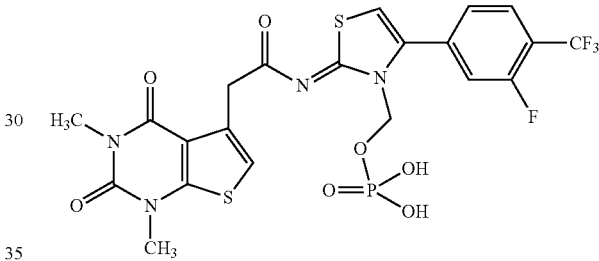

Step 1: Di-tert-butyl[2-{[(1,3-dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3 (2H)-yl]methyl phosphate: The title compound was prepared according to the general procedure as described in method A for the preparation of phosphate derivatives by coupling reaction of 2-(1,3-dimethyl-2,4-dioxo-1,2,3,4-tetrahydrothieno[2,3-d]pyrimidin-5-yl)-N-{4-[3-fluoro-4-(trifluoromethyl)phenyl]-1,3-thiazol-2-yl}acetamide (500 mg, 1.004 mmol) with freshly prepared di-tert-butyl iodomethyl phosphate (Intermediate 2) (1.22 g, 3.514 mmol) in the presence of sodium hydride (60% dispersion in mineral oil, 60.24 mg, 1.506 mmol) in dry DMF (5 ml) to yield 150 mg of pure product as an off-white solid. $^1$H NMR (300 MHz, CDCl$_3$): δ 1.49 (s, 18H), 3.34 (s, 3H), 3.57 (s, 3H), 4.43 (s, 2H), 6.36-6.44 (m, 2H), 6.79 (s, 1H), 7.33 (s, 1H), 7.61 (t, J=7.5 Hz, 1H), 7.71-7.81 (m, 2H); ESI (m/z): 721 (M+H)$^+$.

Step 2: [2-{[(1,3-Dimethyl-2,4-dioxo-1,2,3,4-tetrahydrothieno[2,3-d]pyrimidin-5-yl) acetyl]imino}-4-[3-fluoro-4-(trifluoromethyl)phenyl]-1,3-thiazol-3 (2H)-yl]methyl dihydrogen phosphate: The title compound was prepared according to the general procedure as described in method A for the hydrolysis of phosphate esters by hydrolysis of Step 1 intermediate (145 mg, 0.201 mmol) in dry dichloromethane (3 ml) in the presence of trifluoroacetic acid (46.27 μl, 0.603 mmol) to yield 70 mg of product as a white solid, $^1$H NMR (300 MHz, DMSO-d$_6$): δ 3.16 (s, 3H), 3.47 (s, 3H), 4.43 (s, 2H), 6.24 (br s, 2H), 7.10 (s, 1H), 7.84 (t, J=7.2 Hz, 1H), 8.00 (d, J=8.4 Hz, 1H), 8.05-8.13 (m, 2H); ESI (m/z): 609.02 (M+H)$^+$.

Example 12

Disodium[2-{[(1,3-dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3 (2H)-yl]methyl phosphate

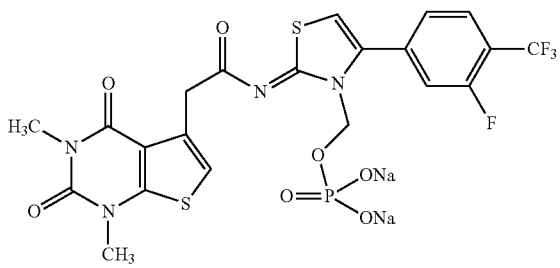

The title compound was prepared according to the general procedure as described in method A for preparation of disodium phosphonate salts by the reaction of Example 11 (65 mg, 0.106 mmol) with sodium metal (23.00 mg, 0.224 mmol) and dry methanol (1 ml) to yield 65 mg of product as a white solid. $^1$H NMR (300 MHz, D$_2$O): δ 3.19 (br s, 3H), 3.50 (br s, 3H), 4.47 (br s, 2H), 6.06 (br s, 2H), 7.00 (br s, 1H), 7.54-7.85 (m, 4H); ESI (m/z): 653.06 (M+H)$^+$.

Example 13

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl dihydrogen phosphate

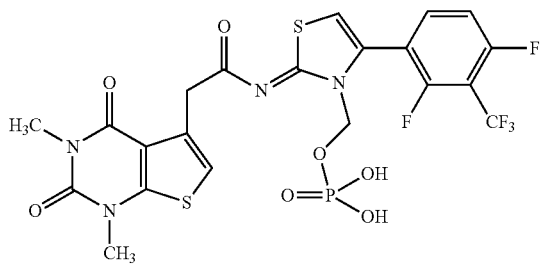 [SMILES: Cn1c(=O)c2c(CC(=O)/N=c3\scc(-c4ccc(F)c(C(F)(F)F)c4F)n3COP(=O)(O)O)csc2n(C)c1=O]

Step 1: Di-tert-butyl[4-[2,4-difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl phosphate: The title compound was prepared according to the general procedure as described in method A for the preparation of phosphate derivatives by coupling reaction of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide (3.10 g, 3.01 mmol) with freshly prepared di-tert-butyl iodomethyl phosphate (intermediate 2) (4.20 g, 12.02 mmol in presence of sodium hydride (60% dispersion in mineral oil, 360 mg, 9.01 mmol) in dry DMF (31 ml) to yield 2.45 g of pure product as an off-white solid; $^1$H NMR (300 MHz, CDCl$_3$): δ 1.46 (s, 18H), 3.34 (s, 3H), 3.57 (s, 3H), 4.43 (s, 2H), 6.43 (d, J=7.8 Hz, 2H), 6.79 (s, 1H), 7.08 (t, J=9.0 Hz, 1H), 7.47 (s, 1H), 8.48 (q, J=8.7 Hz, 1H); ESI (m/z): 738.05 (M+H)$^+$.

Step 2: [4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl dihydrogen phosphate: The title compound was prepared according to the general procedure as described in method A for the hydrolysis of phosphate esters by hydrolysis of Step 1 intermediate (280 mg, 0.379 mmol) using trifluoroacetic acid (87.14 μl, 1.14 mmol) in dichloromethane (6 ml) to yield 180 mg of product as a white solid; $^1$H NMR (300 MHz, D$_2$O): δ 3.20 (br s, 3H), 3.51 (br s, 3H), 4.48 (br s, 2H), 6.04 (br s, 2H), 7.01 (br s, 1H), 7.10-7.25 (m, 1H), 7.51 (br s, 1H), 8.25-8.43 (m, 1H); ESI (m/z): 671.07 (M+H)$^+$.

Example 14

Disodium[4-[2,4-difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl phosphate

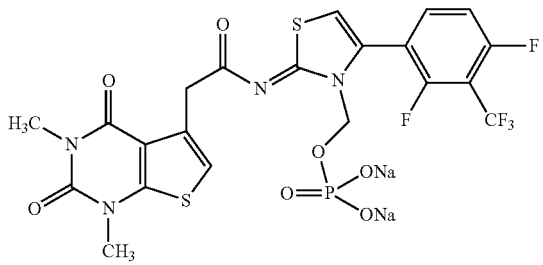

The title compound was prepared according to the general procedure as described in method A for preparation of disodium phosphonate salts by the reaction of ([4-[2,4-difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3 (2H)-yl]methyl dihydrogen phosphate (Example 13) (150 mg, 0.2396 mmol) (150 mg, 0.2396 mmol) with sodium metal (11.57 mg, 0.5031 mmol) in dry methanol (2 ml) to yield 147 mg of product as an off-white solid; $^1$H NMR (300 MHz, D$_2$O): δ 3.19 (br s, 3H), 3.49 (br s, 3H), 4.48 (br s, 2H), 6.04 (br s, 2H), 7.01 (br s, 1H), 7.19 (br s, 1H), 7.49 (br s, 1H), 8.25-8.43 (m, 1H); ESI (m/z): 671.08 (M+H)$^+$.

Example 15

4-(2,4-Difluoro-3-(trifluoromethyl)phenyl)-2-((2-(1,3,6-trimethyl-2,4-dioxo-1,2,3,4-tetrahydrothieno[2,3-d]pyrimidin-5-yl)acetyl)imino)thiazol-3 (2H)-yl) methyl dihydrogen phosphate

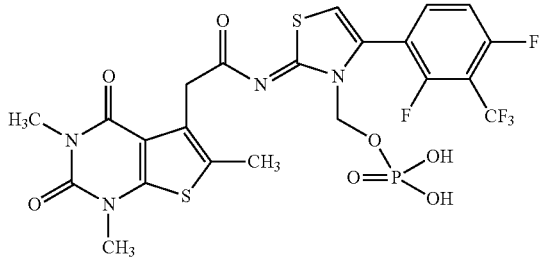 [SMILES: Cc1sc2c(c1CC(=O)/N=c1\scc(-c3ccc(F)c(C(F)(F)F)c3F)n1COP(=O)(O)O)c(=O)n(C)c(=O)n2C]

Step 1: Di-tert-butyl ((4-(2,4-difluoro-3-(trifluoromethyl)phenyl)-2-((2-(1,3,6-trimethyl-2,4-dioxo-1,2,3,4-tetrahydrothieno[2,3-d]pyrimidin-5-yl)acetyl)imino)thiazol-3 (2H)-yl) methyl)phosphate: The title compound was prepared according to the general procedure as described in method A for the preparation of phosphate derivatives by coupling N-{4-[2,4-Difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide (1.10 g, 2.07 mmol) with freshly prepared di-tert-butyl iodomethyl phosphate (intermediate 2) (1.459 g, 4.15 mmol) in dry DMF (11 ml) in presence of sodium hydride (60% dispersion in mineral oil, 0.0745 g, 3.113 mmol) to yield 0.85 g of pure product as an off-white solid. $^1$H NMR (300 MHz, CDCl$_3$): δ 1.46 (s, 18H), 2.42 (s, 3H), 3.33 (s, 3H), 3.52 (s, 3H), 4.40 (s, 2H), 6.47 (d, J=7.8 Hz, 2H), 7.07 (t, J=8.7 Hz, 1H), 7.46 (s, 1H), 8.47 (q, J=9.0 Hz, 1H); APCI (m/z): 752.72 (M+H)⁺.

Step 2: 4-(2,4-Difluoro-3-(trifluoromethyl)phenyl)-2-((2-(1,3,6-trimethyl-2,4-dioxo-1,2,3,4-tetrahydrothieno[2,3-d]pyrimidin-5-yl)acetyl)imino)thiazol-3 (2H)-yl)methyl dihydrogen phosphate: The title compound was prepared according to the general procedure as described in method A for the hydrolysis of phosphate esters by hydrolysis of step 1 intermediate (440 mg, 0.5851 mmol) in dry dichloromethane (9 ml) using trifluoroacetic acid (134 µl, 1.755 mmol) to yield 250 mg of product as an off-white solid. ¹H NMR (300 MHz, DMSO-d₆): δ 2.36 (s, 3H), 3.16 (s, 3H), 3.45 (s, 3H), 4.45 (s, 2H), 6.27 (d, J=6.3 Hz, 2H), 7.51 (t, J=9.0 Hz, 1H), 7.74 (s, 1H), 8.55 (q, J=8.7 Hz, 1H); ESI (m/z): 638.94 (M)⁻.

Example 16

Disodium(4-(2,4-difluoro-3-(trifluoromethyl)phenyl)-2-((2-(1,3,6-trimethyl-2,4-dioxo-1,2,3,4-tetrahydrothieno[2,3-d]pyrimidin-5-yl)acetyl)imino)thiazol-3(2H)-yl)methyl phosphate

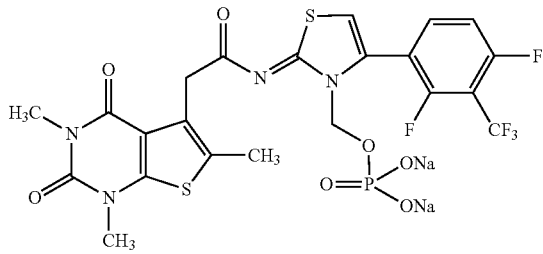

The title compound was prepared according to the general procedure as described in method A for preparation of disodium phosphonate salts by reaction of Example 15 (100 mg, 0.156 mmol) with sodium metal (7.54 mg, 0.328 mmol) in dry methanol (1.25 ml) to yield 70 mg of an off-white solid. Alternatively the title compound was also prepared according to the general procedure as described in method B for preparation of disodium phosphonate salts by reaction of Example 15 (100 mg, 0.156 mmol) with sodium carbonate (16.98 mg, 0.156 mmol) in acetonitrile (8 ml) and water (5 ml), to yield 100 mg of product as an off-white solid. ¹H NMR (300 MHz, D₂O) δ 2.39 (s, 3H), 3.23 (s, 3H), 3.52 (s, 3H), 4.49 (br s, 2H), 6.00-6.20 (m, 2H), 7.25 (t, J=9.3 Hz, 1H), 7.50-7.64 (m, 1H), 8.25-8.45 (m, 1H). ESI-MS (m/z): 639.10 (M−H)⁻.

Example 17

[2-{[(6-ethyl-1,3-dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3 (2H)-yl]methyl dihydrogen phosphate

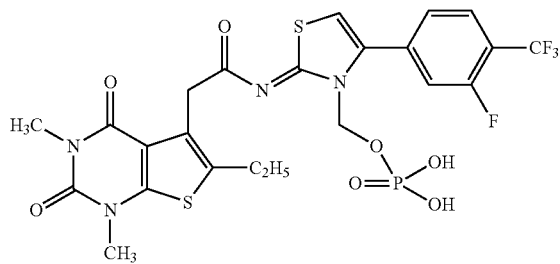 [SMILES: CCc1sc2c(c1CC(=O)/N=c1\scc(-c3ccc(C(F)(F)F)c(F)c3)n1COP(=O)(O)O)c(=O)n(C)c(=O)n2C]

Step 1: Di-tert-butyl[2-{[(6-ethyl-1,3-dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3 (2H)-yl]methyl phosphate: The title compound was prepared according to the general procedure as described in method A for the preparation of phosphate derivatives by coupling reaction of 2-(6-Ethyl-1,3-dimethyl-2,4-dioxo-1,2,3,4-tetrahydrothieno[2,3-d]pyrimidin-5-yl)-N-{4-[3-fluoro-4-(trifluoromethyl)phenyl]-1,3-thiazol-2-yl}acetamide (1.00 g, 1.901 mmol) with freshly prepared intermediate 2 (1.33 g, 3.802 mmol) in presence of sodium hydride (60% dispersion in mineral oil, 115 mg, 2.0851 mmol) in dry DMF (10 ml) to yield 1.15 g of pure product a pale yellow solid. ¹H NMR (300 MHz, CDCl₃): δ 1.20-1.38 (m, 3H), 1.50 (s, 18H), 2.81 (q, J=7.8 Hz, 2H), 3.32 (s, 3H), 3.53 (s, 3H), 4.40 (s, 2H), 6.47 (d, J=7.2 Hz, 2H), 7.21-7.33 (m, 1H), 7.59-7.81 (m, 3H); ESI (m/z): 748.71 (M)⁺.

Step 2: [2-{[(6-Ethyl-1,3-dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3 (2H)-yl]methyl dihydrogen phosphate: The title compound was prepared according to the general procedure as described in method A for the hydrolysis of phosphate esters by hydrolysis of step 1 intermediate (500 mg, 0.6684 mmol) using trifluoroacetic acid (154 µl, 2.005 mmol) in dry dichloromethane (10 ml) to yield 210 mg of product as an off-white solid. ¹H NMR (300 MHz, DMSO-d₆): δ 1.18 (t, J=7.2 Hz, 3H), 2.79 (q, J=7.2 Hz, 2H), 3.16 (s, 3H), 3.46 (s, 3H), 4.45 (s, 2H), 6.28 (d, J=6.0 Hz, 2H), 7.84 (t, J=7.8 Hz, 1H), 8.02 (d, J=8.4 Hz, 1H), 8.08 (s, 1H), 7.98-8.13 (m, 3H); ESI (m/z): 634.79 (M−H)⁻.

Example 18

Disodium[2-{[(6-ethyl-1,3-dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methyl phosphate

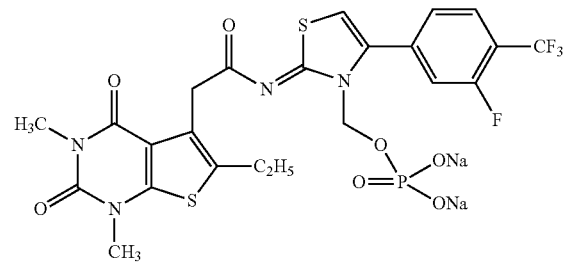

The title compound was prepared according to the general procedure as described in method A for preparation of disodium phosphonate salts by reaction of example 17 (100 mg, 0.159 mmol) with sodium metal (7.59 mg, 0.33 mmol) in dry methanol (1.25 ml) to yield 75 mg of an off-white solid. ¹H NMR (300 MHz, D₂O) δ 1.15-1.35 (m, 3H), 2.65-2.84 (m, 2H), 3.17 (s, 3H), 3.49 (s, 3H), 4.48 (br s, 2H), 6.10-6.20 (m, 2H), 7.50-7.85 (m, 4H). ESI (m/z): 634.80 (M−H)⁻.

Example 19

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl 2,2-dimethylpropanoate

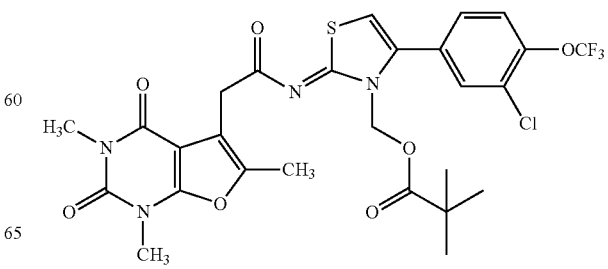

Step 1: Sodium salt of N-{4-[3-chloro-4-(trifluoromethoxy)phenyl]-1,3-thiazol-2-yl}-2-(1,3,6-trimethyl-2,4-dioxo-1,2,3,4-tetrahydrofuro[2,3-d]pyrimidin-5-yl)acetamide: The title compound was prepared according to the general procedure as described in step 1 of method B for the preparation of phosphate derivatives by the reaction of N-{4-[3-Chloro-4-(trifluoromethoxy)phenyl]-1,3-thiazol-2-yl}-2-(1,3,6-trimethyl-2,4-dioxo-1,2,3,4-tetrahydrofuro[2,3-d]pyrimidin-5-yl)acetamide (50 g, 0.09 mol) in dry ethanol (300 ml), sodium tert-butoxide solution (9.07 g, 0.09 mol) and n-pentane (800 ml) to obtain 54 g of the desired product. $^1$H NMR (300 MHz, DMSO-d$_6$) δ 2.25 (s, 3H), 3.12 (s, 3H), 3.35 (s, 3H), 3.42 (s, 2H), 7.24 (s, 1H), 7.42 (d, J=6.9 Hz, 1H), 7.86 (d, J=6.9 Hz, 1H), 8.06 (s, 1H).

Step 2: [4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl 2,2-dimethylpropanoate: The title compound was prepared by the reaction of sodium salt of N-{4-[3-chloro-4-(trifluoromethoxy)phenyl]-1,3-thiazol-2-yl}-2-(1,3,6-trimethyl-2,4-dioxo-1,2,3,4-tetrahydrofuro[2,3-d]pyrimidin-5-yl)acetamide (2.0 g, 0.0036 mol) with chloromethyl pivalate (0.82 g, 0.005455 mol) in dry acetone (60 ml) to yield 390 mg of product as an off white solid. $^1$H NMR (300 MHz, CDCl$_3$) δ 1.22 (s, 9H), 2.34 (s, 3H), 3.33 (s, 3H), 3.53 (s, 3H), 4.11 (s, 2H), 6.49 (s, 2H), 7.24 (s, 1H), 7.36 (d, J=7.8 Hz, 1H), 7.79 (d, J=8.7 Hz, 1H), 7.98 (s, 1H). ESI-MS (m/z): 642.75 (M+H)$^+$.

Example 20

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl] methyl glycinate hydrochloride

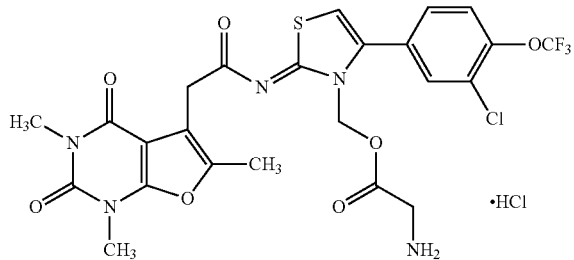 [SMILES: Cc1oc2c(c1CC(=O)/N=c1\scc(-c3ccc(OC(F)(F)F)c(Cl)c3)n1COC(=O)CN)c(=O)n(C)c(=O)n2C ; Cl]

Step 1: [4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl N-(tert-butoxycarbonyl)glycinate: The title compound was prepared by coupling N-{4-[3-Chloro-4-(trifluoromethoxy)phenyl]-1,3-thiazol-2-yl}-2-(1,3,6-trimethyl-2,4-dioxo-1,2,3,4-tetrahydrofuro[2,3-d]pyrimidin-5-yl)acetamide (2.08 g, 6.615 mmol) with intermediate 3 (732 mg, 1.984 mmol) using sodium hydride (60% dispersion in mineral oil, 113 mg, 2.83 mmol) in dry DMF (20 ml) according to step 1 of general procedure described for the preparation of amino acid derivatives to yield 380 mg of product as an off-white solid. $^1$H NMR (300 MHz, CDCl$_3$): δ 1.40 (br s, 9H), 2.36 (s, 3H), 3.32 (s, 3H), 3.53 (s, 3H), 4.02 (d, J=6.0 Hz, 2H), 4.09 (s, 2H), 5.17-5.24 (m, 1H), 6.63 (br s, 2H), 7.25 (s, 1H), 7.36 (d, J=8.1 Hz, 1H), 7.79 (d, J=6.9 Hz, 1H), 7.97 (s, 1H); APCI (m/z): 715.80 (M+H)$^+$.

Step 2: [4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl glycinate Hydrochloride: The title compound was prepared by deprotection of step 1 intermediate (295 mg, 0.637 mmol) with saturated solution of hydrochloride in dry ethyl acetate (8.0 ml) according to step 2 of general procedure described for the preparation of amino acid derivatives to yield 190 mg of product as an off-white solid. $^1$H NMR (300 MHz, DMSO-d$_6$): δ 2.33 (s, 3H), 3.16 (s, 3H), 3.43 (m, 3H), 4.01 (s, 2H), 4.23 (s, 2H), 6.67 (s, 2H), 7.65 (d, J=8.4 Hz, 1H), 8.00-8.05 (m, 2H), 8.25 (s, 1H), 8.27-8.40 (m, 3H); APCI (m/z): 616.15 (M+H)$^+$.

Example 21

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl] methyl L-valinate hydrochloride

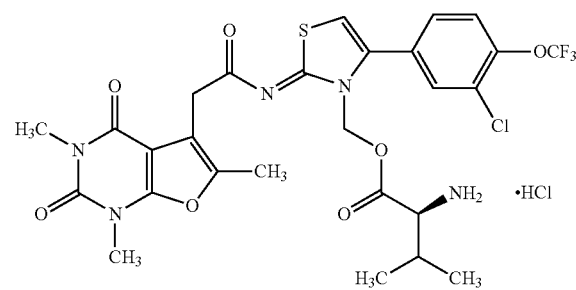 [SMILES: Cc1oc2c(c1CC(=O)/N=c1\scc(-c3ccc(OC(F)(F)F)c(Cl)c3)n1COC(=O)[C@@H](N)C(C)C)c(=O)n(C)c(=O)n2C ; Cl]

Step 1: [4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl N-(tert-butoxycarbonyl)-L-valinate: The title compound was prepared by coupling N-{4-[3-chloro-4-(trifluoromethoxy)phenyl]-1,3-thiazol-2-yl}-2-(1,3,6-trimethyl-2,4-dioxo-1,2,3,4-tetrahydrofuro[2,3-d]pyrimidin-5-yl)acetamide (8.00 g, 15.126 mmol) with intermediate 5 (18.91 g, 52.941 mmol) using sodium hydride (60% dispersion in mineral oil, 907.5 mg, 22.68 mmol) in dry DMF (80 ml) according to step 1 of general procedure described for the preparation of amino acid derivatives to yield 3.68 g of product as an off-white solid. $^1$H NMR (300 MHz, CDCl$_3$): δ 0.87 (t, J=6.0 Hz, 3H), 0.95 (t, J=6.0 Hz, 3H), 1.39 (s, 9H), 2.03-2.19 (m, 2H), 2.37 (s, 3H), 3.33 (s, 3H), 3.53 (s, 3H), 4.01-4.17 (m, 2H), 4.20-4.30 (m, 1H), 5.21 (d, J=9.0 Hz, 1H), 6.42-6.70 (m, 2H), 7.26 (s, 1H), 7.35 (d, J=9.0 Hz, 1H), 7.78 (d, J=9.0 Hz, 1H), 7.97 (s, 1H); APCI (m/z): 757.55 (M+H)$^+$.

Step 2: [4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl L-valinate hydrochloride: The title compound was prepared according to step 2 of general procedure described for the preparation of amino acid derivatives by deprotection of step 1 intermediate (3.60 g, 4.755 mmol) with saturated solution of hydrochloride in dry ethyl acetate (200 ml) to yield 2.905 g of product as a white solid. $^1$H NMR (300 MHz, DMSO-d$_6$): δ 0.92 (t, J=6.6 Hz, 6H), 2.16-2.24 (m, 1H), 2.34 (s, 3H), 3.16 (s, 3H), 3.43 (s, 3H), 4.02 (d, J=6.0 Hz, 1H), 4.24-4.35 (m, 2H), 6.63 (br s, 2H), 7.65 (d, J=9.0 Hz, 1H), 7.98-8.04 (m, 2H), 8.22 (s, 1H), 8.43-8.60 (m, 3H); APCI (m/z): 658.24 (M+H)$^+$.

Example 22

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl] methyl L-isoleucinate hydrochloride

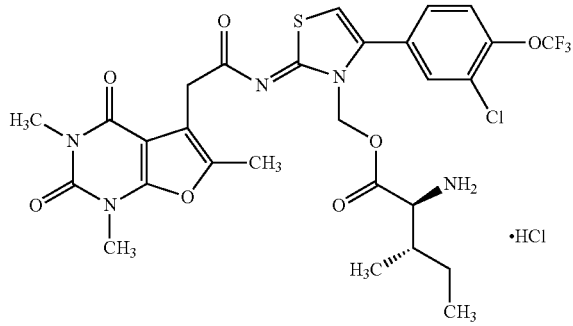 [SMILES: CC[C@H](C)[C@H](N)C(=O)OCn1c(-c2ccc(OC(F)(F)F)c(Cl)c2)cs/c1=N\C(=O)Cc1c(C)oc2c1c(=O)n(C)c(=O)n2C ; Cl]

Step-1: [4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl N-(tert-butoxycarbonyl) L-isoleucinate: The title compound was prepared by the reaction of sodium salt of N-{4-[3-Chloro-4-(trifluoromethoxy)phenyl]-1,3-thiazol-2-yl}-2-(1,3,6-trimethyl-2,4-dioxo-1,2,3,4-tetrahydrofuro[2,3-d]pyrimidin-5-yl)acetamide (1.0 g, 0.0018 mol) in dry acetone (40 ml) with intermediate 6 (2.36 g, 0.0063 mol) in dry acetone (10 ml) to obtain 210 mg of product as a pale yellow solid. $^1$H NMR (300 MHz, CDCl$_3$) δ 0.74 (t, J=7.5 Hz, 3H), 0.89 (d, J=6.9 Hz, 3H), 1.25 (s, 9H), 1.80-1.87 (m, 2H), 2.36 (s, 3H), 3.33 (s, 3H), 3.50-3.57 (m, 5H), 3.73 (s, 2H), 4.26-4.33 (m, 1H), 5.19 (d, J=9.0 Hz, 1H), 6.49 (d, J=12.2 Hz, 1H), 6.64 (d, J=11.7 Hz, 1H), 7.36 (d, J=8.1 Hz, 1H), 7.71-7.79 (m, 1H), 11.40 (br s, 1H); ESI-MS (m/z): 772.01 (M+H)$^+$.

Step-2: [4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl L-isoleucinate hydrochloride: The title compound was prepared according to step 2 of general procedure described for the preparation of amino acid derivatives by deprotection of step 1 intermediate (200 mg, 0.00025 mol) with saturated solution ethyl acetate-HCl (8.0 ml) in ethyl acetate (8.0 ml) to yield 75 mg of the desired product as an off white solid. $^1$H NMR (300 MHz, DMSO-d$_6$) δ 0.72 (t, J=7.5 Hz, 3H), 0.87 (d, J=6.9 Hz, 3H), 1.16-1.1.24 (m, 2H), 1.87-1.95 (m, 1H), 2.33 (s, 3H) 3.16 (s, 3H), 3.43 (s, 3H), 4.06-4.13 (m, 1H), 4.24-4.30 (m, 2H), 6.62 (br s, 2H), 7.66 (d, J=8.7 Hz, 1H), 7.97-8.04 (m, 2H), 8.22 (s, 1H), 8.46 (br s, 3H); ESI-MS (m/z): 671.94 (M)$^+$.

Example 23

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl] methyl piperidine-4-carboxylate hydrochloride

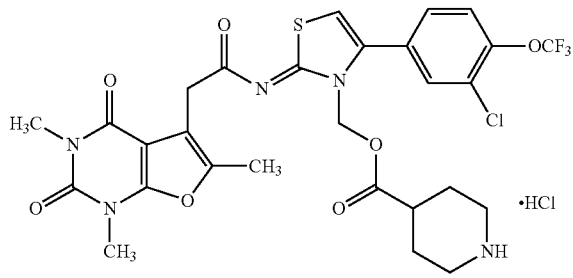 [SMILES: Cc1oc2c(c1CC(=O)/N=c1\scc(-c3ccc(OC(F)(F)F)c(Cl)c3)n1COC(=O)C1CCNCC1)c(=O)n(C)c(=O)n2C ; Cl]

Step 1: 1-tert-Butyl 4-{[4-[3-chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl}piperidine-1,4-dicarboxylate: The title compound was prepared according to step 1 of general procedure described for the preparation of amino acid derivatives by coupling N-{4-[3-chloro-4-(trifluoromethoxy)phenyl]-1,3-thiazol-2-yl}-2-(1,3,6-trimethyl-2,4-dioxo-1,2,3,4-tetrahydrofuro[2,3-d]pyrimidin-5-yl)acetamide (300 mg, 0.567 mmol) with intermediate 8 (732 mg, 1.984 mmol) using sodium hydride (60% dispersion in mineral oil, 34 mg, 0.850 mmol) in dry DMF (3 ml) to yield 101 mg of product as an off-white solid; $^1$H NMR (300 MHz, CDCl$_3$): δ 1.45 (s, 9H), 1.56-1.71 (m, 2H), 1.87-2.03 (m, 2H), 2.35 (s, 3H), 2.50-2.62 (m, 1H), 2.77-2.87 (s, 2H), 3.32 (s, 3H), 3.53 (s, 3H), 3.95-4.03 (m, 2H), 4.09 (s, 2H), 6.53 (br s, 2H), 7.24-7.28 (m, 1H), 7.36 (d, J=6.0 Hz, 1H), 7.77 (d, J=6.0 Hz, 1H), 7.98 (s, 1H); ESI (m/z): 769.88 (M+H)$^+$.

Step 2: [4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl piperidine-4-carboxylate hydrochloride: The title compound was prepared according to step 2 of general procedure described for the preparation of amino acid derivatives by deprotection of Step 1 intermediate (97 mg, 0.125 mmol) with saturated solution of hydrochloride in dry ethyl acetate (5 ml) to yield 61 mg of product as a white solid; $^1$H NMR (300 MHz, DMSO-d$_6$): δ 1.71-1.82 (m, 2H), 1.96-2.08 (m, 2H), 2.32 (s, 3H), 2.19-2.91 (m, 4H), 3.13-3.24 (m, 4H), 3.43 (s, 3H), 4.21 (s, 2H), 6.49 (s, 2H), 7.66 (d, J=7.8 Hz, 1H), 7.99-8.03 (m, 2H), 8.21 (s, 1H), 8.40-8.50 (m, 1H), 8.69-8.79 (m, 1H); ESI (m/z): 670 (M)$^+$.

Example 24

4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl] methyl L-phenylalaninate hydrochloride

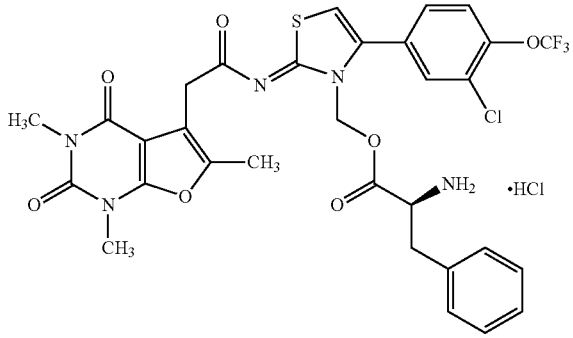 [SMILES: Cc1oc2c(c1CC(=O)/N=c1\scc(-c3ccc(OC(F)(F)F)c(Cl)c3)n1COC(=O)[C@@H](N)Cc1ccccc1)c(=O)n(C)c(=O)n2C ; Cl]

Step-1: [4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl N-(tert-butoxycarbonyl)-L-phenylalaninate: The title compound was prepared by coupling reaction of sodium salt of N-{4-[3-chloro-4-(trifluoromethoxy)phenyl]-1,3-thiazol-2-yl}-2-(1,3,6-trimethyl-2,4-dioxo-1,2,3,4-tetrahydrofuro[2,3-d]pyrimidin-5-yl)acetamide (3.0 g, 0.0018 mol) with intermediate 9 (2.36 g, 0.0063 mol) in dry acetone (75 ml) to yield 1.2 g of product as an off white solid. $^1$H NMR (300 MHz, CDCl$_3$) δ 1.36 (br s, 9H), 2.34 (s, 3H), 3.07 (d, J=6.3 Hz, 2H), 3.31 (s, 3H), 3.47-3.55 (m, 3H), 3.94-4.00 (m, 2H), 4.60-4.68 (m, 2H), 5.25 (d, J=7.8 Hz, 1H), 6.46-6.52 (m, 1H), 6.64-6.70 (m, 1H), 7.07-7.15 (m, 5H), 7.36 (d, J=8.4 Hz, 1H), 7.79 (d, J=8.7 Hz, 1H), 7.97 (s, 1H); APCI-MS (m/z): 806.05 (M+H)$^+$.

Step-2: [4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl L-phenylalaninate hydrochloride: The title compound was prepared according to step 2 of general procedure described for the preparation of amino acid derivatives by deprotetion of step 1 intermediate (500 mg, 0.00062 mol) using saturated ethyl acetate-HCl (25.0 ml) to yield 350 mg of pure product as an off white solid; $^1$H NMR (300 MHz, DMSO-$d_6$) δ 2.32 (s, 3H), 3.15 (s, 3H), 3.19-3.25 (m, 2H), 3.43 (s, 3H), 4.11 (br s, 2H), 4.39 (br s, 1H), 6.61 (br s, 2H), 7.07-7.18 (m, 5H), 7.66 (d, J=8.4 Hz, 1H), 8.00-8.06 (m, 2H), 8.23 (s, 1H), 8.73 (br s, 3H). APCI-MS (m/z): 705.93 (M)$^+$.

Example 25

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl dihydrogen phosphate

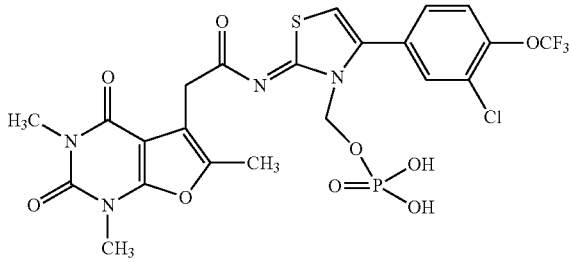 [SMILES: Cc1oc2c(c1CC(=O)/N=c1\scc(-c3ccc(OC(F)(F)F)c(Cl)c3)n1COP(=O)(O)O)c(=O)n(C)c(=O)n2C]

Step 1: Di-tert-butyl[4-[3-chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl phosphate: The title compound was prepared according to the general procedure as described in method C for the preparation of phosphate derivatives by the reaction of sodium salt of N-{4-[3-chloro-4-(trifluoromethoxy)phenyl]-1,3-thiazol-2-yl}-2-(1,3,6-trimethyl-2,4-dioxo-1,2,3,4-tetrahydrofuro[2,3-d]pyrimidin-5-yl)acetamide (50 g, 0.09 mol) with di-tert-butyl chloromethyl phosphate (Intermediate 1) (58.6 g, 0.23 mol) in presence of sodium iodide (10.8 g, 0.072 mol) in dry acetone (1250 ml) to obtain 50 g of a product as a pale yellow solid. Alternatively the title compound was also prepared according to the general procedure as described in step 2 of method B for the preparation of phosphate derivatives by coupling N-{4-[3-chloro-4-(trifluoromethoxy)phenyl]-1,3-thiazol-2-yl}-2-(1,3,6-trimethyl-2,4-dioxo-1,2,3,4-tetrahydrofuro[2,3-d]pyrimidin-5-yl)acetamide (500 mg, 0.945 mmol) with freshly prepared di-tert-butyl iodomethyl phosphate (Intermediate 2) (1.16 g, 3.307 mmol) using sodium hydride (57 mg, 1.418 mmol) in dry DMF (5 ml) to yield 197 mg of product as an off-white solid; $^1$H NMR (300 MHz, CDCl$_3$): δ 1.49 (br s, 18H), 2.36 (s, 3H), 3.32 (s, 3H), 3.53 (s, 3H), 4.18 (s, 2H), 6.43 (d, J=6.3 Hz, 2H), 7.22-7.29 (m, 1H), 7.34 (d, J=8.4 Hz, 1H), 7.78 (t, J=8.7 Hz, 1H), 8.05 (s, 1H); ESI (m/z): 751 (M+H)$^+$.

Step 2: [4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl dihydrogen phosphate The title compound was prepared according to the general procedure as described in method B for the hydrolysis of phosphate esters by hydrolysis of step 1 intermediate (50 g, 0.066 mol) in acetone (4000 ml) and water (4000 ml) to give 22 g of the title compound as an off white solid. Alternatively the title compound was prepared according to the general procedure as described in method A for the hydrolysis of phosphate esters by hydrolysis of Step 1 intermediate (63 mg, 0.083 mmol) with trifluoro acetic acid (20 μl, 0.251 mmol) in dichloromethane (750 μl) to yield 11 mg of product as a white solid; $^1$H NMR (300 MHz, DMSO-$d_6$): δ 2.30 (s, 3H), 3.14 (s, 3H), 3.41 (s, 3H), 4.25 (s, 2H), 6.24 (d, J=6.0 Hz, 2H), 7.61 (d, J=8.4 Hz, 1H), 7.96 (s, 1H), 8.05 (d, J=8.7 Hz, 1H), 8.27 (s, 1H); APCI-MS (m/z): 639.11 (M+H)$^+$.

Example 26

Disodium[4-[3-chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3 (2H)-yl]methyl phosphate

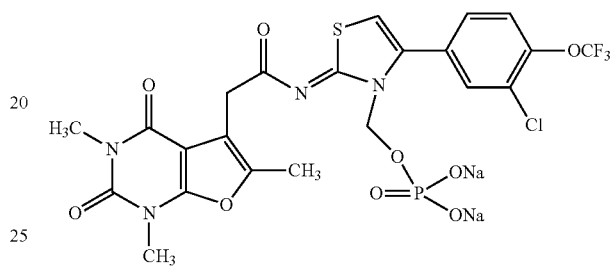

The title compound was prepared according to the general procedure as described in method C preparation of disodium phosphonate salts by reaction of Example 25 (22 g, 0.034 mol) with sodium tert-butoxide (8.28 g, 0.0862 mol) in dry methanol (550 ml) to obtain 15 g of product as an off white solid. $^1$H NMR (300 MHz, D$_2$O) δ 2.32 (s, 3H), 3.17 (s, 3H), 3.47 (s, 3H), 4.26 (s, 2H), 6.06 (br s, 2H), 7.48 (s, 2H), 7.81 (s, 1H), 8.00 (s, 1H). ESI-MS (m/z): 636.99 (M−H)$^-$.

Example 27

4-[2,3-Difluoro-4-(trifluoromethyl)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl dihydrogen phosphate

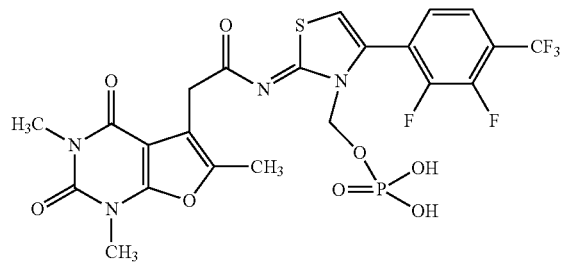 [SMILES: Cc1oc2c(c1CC(=O)/N=c1\scc(-c3ccc(C(F)(F)F)c(F)c3F)n1COP(=O)(O)O)c(=O)n(C)c(=O)n2C]

Step 1: Sodium salt of N1-[4-(2,3-Difluoro-4-trifluoromethylphenyl)-1,3-thiazol-2-yl]-2-(1,3,6-trimethyl-2,4-dioxo-1,2,3,4-tetrahydrofuro[2,3-d]pyrimidin-5-yl)acetamide: The title compound was prepared according to the general procedure as described in step 1 of method B for the preparation of phosphate derivatives by reaction of N1-[4-(2,3-Difluoro-4-trifluoromethylphenyl)-1,3-thiazol-2-yl]-2-(1,3,6-trimethyl-2,4-dioxo-1,2,3,4-tetrahydrofuro[2,3-d]pyrimidin-5-yl)acetamide (2.0 g, 3.891 mmol) with sodium tert-butoxide (411 mg, 4.28 mmol) in dry ethanol (24 ml) as to yield 2.0 g of product as an off-white solid.

Step 2: Di-tert-butyl ((4-(2,3-difluoro-4-(trifluoromethyl)phenyl)-2-((2-(1,3,6-trimethyl-2,4-dioxo-1,2,3,4-tetrahydrofuro[2,3-d]pyrimidin-5-yl)acetyl)imino)thiazol-3 (2H)-yl)methyl) phosphate: The title compound was prepared according to the general procedure as described in method C for the preparation of phosphate derivatives by coupling reaction of sodium salt of N1-[4-(2,3-Difluoro-4-trifluoromethylphenyl)-1,3-thiazol-2-yl]-2-(1,3,6-trimethyl-2,4-dioxo-1,2,3,4-tetrahydrofuro[2,3-d]pyrimidin-5-yl)acetamide (2.0 g, 3.73 mmol) with di-tert-butyl chloromethyl phosphate (Intermediate 1) (2.41 g, 9.328 mmol) in presence of sodium iodide (559 mg, 3.731 mmol) in dry acetone (50 ml) to obtain 3.0 g of a product as a pale yellow solid; ESI-MS (m/z): 736.70 (M+H)$^+$.

Step 3: 4-[2,3-Difluoro-4-(trifluoromethyl)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl dihydrogen phosphate: The title compound was prepared according to the general procedure as described in method B for the hydrolysis of phosphate esters by hydrolysis of step 2 intermediate (3.0 g) using acetone (100 ml) and water (100 ml) to give 400 mg of product as a pale yellow solid. $^1$H NMR (300 MHz, DMSO-d$_6$): δ 2.29 (s, 3H), 3.13 (s, 3H), 3.41 (s, 3H), 4.27 (s, 2H), 6.22 (d, J=5.4 Hz, 2H), 7.66 (d, J=7.2 Hz, 1H), 7.87 (s, 1H), 8.17 (t, J=7.5 Hz, 1H); APCI-MS (m/z): 622.94.11 (M−H)$^-$.

Example 28

4-(2,4-Difluoro-3-(trifluoromethyl)phenyl)-2-((2-(2,5,7-trimethyl-4,6-dioxo-4,5,6,7-tetrahydro-2H-pyrazolo[3,4-d]pyrimidin-3-yl)acetyl)imino)thiazol-3 (2H)-yl)methyl dihydrogen phosphate

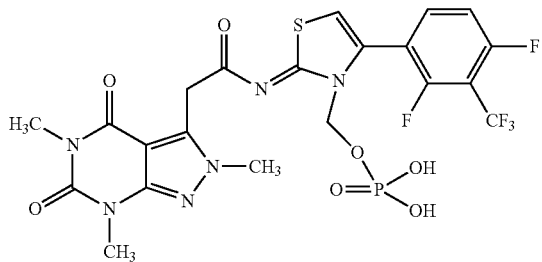 [SMILES: Cn1nc2c(c1CC(=O)/N=c1\scc(-c3ccc(F)c(C(F)(F)F)c3F)n1COP(=O)(O)O)c(=O)n(C)c(=O)n2C]

Step 1: Sodium salt N-(4-(2,4-difluoro-3-(trifluoromethyl)phenyl)thiazol-2-yl)-2-(2,5,7-trimethyl-4,6-dioxo-4,5,6,7-tetrahydro-2H-pyrazolo[3,4-d]pyrimidin-3-yl)acetamide:
The title compound was prepared according to the general procedure as described in step 1 of method B for the preparation of phosphate derivatives by the reaction of N-(4-(2,4-difluoro-3-(trifluoromethyl)phenyl)thiazol-2-yl)-2-(2,5,7-trimethyl-4,6-dioxo-4,5,6,7-tetrahydro-2H-pyrazolo[3,4-d]pyrimidin-3-yl)acetamide (500 mg, 0.96 mmol) with sodium-tert-butoxide (93 mg, 0.996 mmol) in dry THF (3 ml) and hexane (10 ml) to yield 503 mg of product as an off-white solid. $^1$H NMR (300 MHz, DMSO-d$_6$): δ 3.18 (s, 3H), 3.37 (s, 3H), 3.78 (s, 2H), 3.97 (s, 2H), 7.08 (s, 1H), 7.38 (t, J=9.9 Hz, 1H), 8.38 (t, t, J=8.4 Hz, 1H).

Step 2: Di-tert-butyl[4-[2,4-difluoro-3-(trifluoromethyl)phenyl]-2-{[(2,5,7-trimethyl-4,6-dioxo-4,5,6,7-tetrahydro-2H-pyrazolo[3,4-d]pyrimidin-3-yl)acetyl]imino}-1,3-thiazol-3(2H)-yl]methyl phosphate: The title compound was prepared according to the general procedure as described in step 2 of method B for the preparation of phosphate derivatives by the reaction of sodium salt of N-(4-(2,4-difluoro-3-(trifluoromethyl)phenyl)thiazol-2-yl)-2-(2,5,7-trimethyl-4,6-dioxo-4,5,6,7-tetrahydro-2H-pyrazolo[3,4-d]pyrimidin-3-yl)acetamide (500 mg, 0.93 mmol) with freshly prepared di-tert-butyl iodomethyl phosphate (Intermediate 2) (489 mg, 1.39 mmol) dry DMF (5 ml) to yield 460 mg of product as a white solid. The title compound was also prepared according to the general procedure as described in method A by coupling of N-(4-(2,4-difluoro-3-(trifluoromethyl)phenyl)thiazol-2-yl)-2-(2,5,7-trimethyl-4,6-dioxo-4,5,6,7-tetrahydro-2H-pyrazolo[3,4-d]pyrimidin-3-yl)acetamide (2.50 g, 4.86 mmol) with freshly prepared di-tert-butyl iodomethyl phosphate (Intermediate 2) (5.95 g, 17.02 mmol) in the presence of sodium hydride (60% dispersion in mineral oil, 291 mg, 7.29 mmol) in dry DMF (25 ml) to yield 1.35 g of pure product as an off-white solid. $^1$H NMR (300 MHz, CDCl$_3$): δ 1.44 (s, 18H), 3.34 (s, 3H), 3.51 (s, 3H), 3.92 (s, 3H), 4.74 (s, 2H), 6.44 (d, J=9.6 Hz, 2H), 7.09 (t, J=9.3 Hz, 1H), 7.51 (s, 1H), 8.45 (q, J=9.0 Hz, 1H). ESI (m/z): 736.56 (M+H)$^+$.

Step 3: 4-(2,4-Difluoro-3-(trifluoromethyl)phenyl)-2-((2-(2,5,7-trimethyl-4,6-dioxo-4,5,6,7-tetrahydro-2H-pyrazolo[3,4-d]pyrimidin-3-yl)acetyl)imino)thiazol-3 (2H)-yl)methyl dihydrogen phosphate: The title compound was prepared according to the general procedure as described in method A for the hydrolysis of phosphate esters by hydrolysis of step 2 intermediate (1.33 g, 1.807 mmol) in dry dichloromethane (27 ml) using trifluoroacetic acid (415 μl, 1.99 mmol) to yield 740 mg of product as a white solid.

Alternatively the title compound was also prepared according to the general procedure as described in method B for the hydrolysis of phosphate esters by hydrolysis of step 1 intermediate (200 mg, 0.271 mmol) using acetone (16 ml) and water (16 ml) to yield 75 mg of product as a white solid. $^1$H NMR (300 MHz, DMSO-d$_6$+2 drops of Et$_3$N): δ 3.18 (s, 3H), 3.38 (s, 3H), 3.85 (s, 3H), 4.84 (s, 2H), 6.26 (d, J=7.2 Hz, 2H), 7.51 (t, J=9.6 Hz, 1H), 7.80 (s, 1H), 8.56 (q, J=8.1 Hz, 1H); ESI (m/z): 622.95 (M−H)$^-$.

Example 29

Disodium-(4-(2,4-difluoro-3-(trifluoromethyl)phenyl)-2-((2-(2,5,7-trimethyl-4,6-dioxo-4,5,6,7-tetrahydro-2H-pyrazolo[3,4-d]pyrimidin-3-yl)acetyl)imino)thiazol-3 (2H)-yl)methyl phosphate

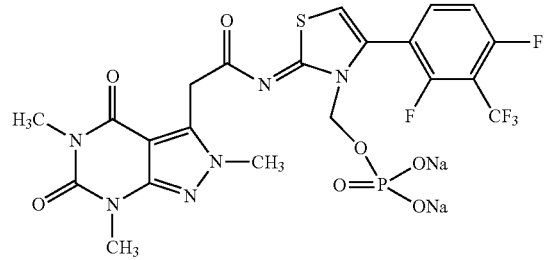

The title compound was prepared according to the general procedure as described in method B for preparation of disodium phosphonate salts by the reaction of Example 28 (715 mg, 1.145 mmol) with sodium carbonate (121.45 mg, 1.145 mmol) in acetonitrile (57 ml) and water (38 ml) to yield 660 mg of product as an off-white solid. $^1$H NMR (300 MHz, D$_2$O) δ 3.22 (s, 3H), 3.41 (s, 3H), 3.85 (s, 3H), 4.44-4.55 (m, 2H), 5.94-6.20 (m, 2H), 7.21 (t, J=9.6 Hz, 1H), 7.45-7.60 (m, 1H), 8.20-8.43 (m, 1H). ESI (m/z): 622.76 (M−H)$^-$.

Example 30

(4-(3,4-Dichlorophenyl)-2-((2-(1,3-dimethyl-2,6-dioxo-2,3-dihydro-1H-purin-7(6H)-yl)acetyl)imino)thiazol-3(2H)-yl)methyl dihydrogen phosphate

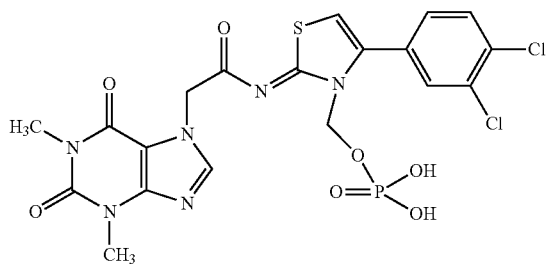 [SMILES: Cn1c(=O)c2c(ncn2CC(=O)/N=c2\scc(-c3ccc(Cl)c(Cl)c3)n2COP(=O)(O)O)n(C)c1=O]

Step 1: Di-tert-butyl ((4-(3,4-dichlorophenyl)-2-((2-(1,3-dimethyl-2,6-dioxo-2,3-dihydro-1H-purin-7(6H)-yl)acetyl)imino)thiazol-3(2H)-yl)methyl) phosphate: The title compound was prepared according to the general procedure as described in method A for the preparation of phosphate derivatives by coupling N-[4-(3,4-dichlorophenyl)-1,3-thiazol-2-yl]-2-(1,3-dimethyl-2,6-dioxo-1,2,3,6-tetrahydro-7H-purin-7-yl)acetamide (150 mg, 0.322 mmol) with freshly prepared di-tert-butyl iodomethyl phosphate (Intermediate 2) (395.16 mg, 1.129 mmol) in the presence of sodium hydride (60% dispersion in mineral oil, 20 mg, 0.483 mmol) in dry DMF (2 ml) with to yield 135 mg of pure product as an off-white solid. $^1$H NMR (300 MHz, CDCl$_3$): δ 1.48 (br s, 18H), 3.35 (s, 3H), 3.47 (s, 2H), 3.62 (s, 3H), 5.71 (s, 2H), 6.36 (br s, 2H), 7.42-7.50 (m, 1H), 7.60-7.72 (m, 1H), 8.02 (s, 1H).

Step 2: (4-(3,4-Dichlorophenyl)-2-((2-(1,3-dimethyl-2,6-dioxo-2,3-dihydro-1H-purin-7(6H)-yl)acetyl)imino)thiazol-3(2H)-yl)methyl dihydrogen phosphate: The title compound was prepared according to the general procedure as described in method A for the hydrolysis of phosphate esters by hydrolysis of Step 1 intermediate (40 mg, 0.0582 mmol) in dry dichloromethane (1 ml) using trifluoroacetic acid (19.91 mg, 0.175 mmol) to yield 23 mg of product as a white solid. $^1$H NMR (300 MHz, DMSO-d$_6$): δ 3.19 (s, 3H), 3.47 (s, 3H), 5.80 (s, 2H), 6.17-6.23 (m, 2H), 7.71 (d, J=8.7 Hz, 1H), 7.96-8.03 (m, 2H), 8.10 (s, 1H), 8.25 (s, 1H); ESI (m/z): 574.95 (M–H)$^-$.

Example 31

[4-[2,3-Difluoro-4-(trifluoromethyl)phenyl]-2-{[(5,7-dimethyl-4,6-dioxo-4,5,6,7-tetrahydro[1,2]thiazolo[5,4-d]pyrimidin-3-yl)acetyl]imino}-1,3-thiazol-3(2H)-yl]methyl dihydrogen phosphate

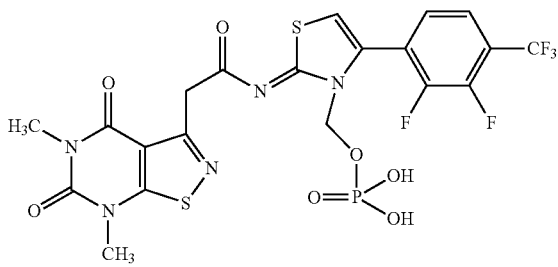

Step 1: Sodium salt of N-{4-[2,3-Difluoro-4-(trifluoromethyl)phenyl]-1,3-thiazol-2-yl}-2-(5,7-dimethyl-4,6-dioxo-4,5,6,7-tetrahydro[1,2]thiazolo[5,4-d]pyrimidin-3-yl)acetamide: The title compound was prepared according to the general procedure as described in step 1 of method B for the preparation of phosphate derivatives by the reaction of N-{4-[2,3-difluoro-4-(trifluoromethyl)phenyl]-1,3-thiazol-2-yl}-2-(5,7-dimethyl-4,6-dioxo-4,5,6,7-tetrahydro[1,2]thiazolo[5,4-d]pyrimidin-3-yl)acetamide (1.95 g, 3.771 mmol) with sodium-tert-butoxide (0.362 g, 3.771 mmol) in dry THF (12 ml) and hexane (40 ml) to yield 2.00 g of product as an off-white solid. $^1$H NMR (300 MHz, DMSO-d$_6$): δ 3.22 (s, 3H), 3.48 (s, 3H), 3.98 (s, 2H), 7.25 (s, 1H), 7.59 (t, J=8.1 Hz, 1H), 8.03 (t, t, J=7.2 Hz, 1H).

Step 2: Di-tert-butyl 4-[2,3-difluoro-4-(trifluoromethyl)phenyl]-2-{[(5,7-dimethyl-4,6-dioxo-4,5,6,7-tetrahydro[1,2]thiazolo[5,4-d]pyrimidin-3-yl)acetyl]imino}-1,3-thiazol-3(2H)-yl]methyl phosphate: The title compound was prepared according to the general procedure as described in step 2 of method B for the preparation of phosphate derivatives by the reaction of sodium salt of N-{4-[2,3-difluoro-4-(trifluoromethyl)phenyl]-1,3-thiazol-2-yl}-2-(5,7-dimethyl-4,6-dioxo-4,5,6,7-tetrahydro[1,2]thiazolo[5,4-d]pyrimidin-3-yl)acetamide (2.0 g, 3.71 mmol) with freshly prepared di-tert-butyl iodomethyl phosphate (Intermediate 2) (1.948 g, 5.56 mol) in dry DMF (20 ml) to yield 1.035 g of product as a white solid. Alternatively the title compound was also prepared according to the general procedure as described in method A for the preparation of phosphate derivatives by coupling N-{4-[2,3-difluoro-4-(trifluoromethyl)phenyl]-1,3-thiazol-2-yl}-2-(5,7-dimethyl-4,6-dioxo-4,5,6,7-tetrahydro[1,2]thiazolo[5,4-d]pyrimidin-3-yl)acetamide (500 mg, 0.967 mmol) with freshly prepared di-tert-butyl iodomethyl phosphate (Intermediate 2) (1.18 g, 3.38 mmol) in presence of sodium hydride (60% dispersion in mineral oil, 58 mg, 1.45 mmol) in dry DMF (5 ml) to yield 135 mg of product as an off-white solid. $^1$H NMR (300 MHz, CDCl$_3$): δ 1.46 (s, 18H), 3.36 (s, 3H), 3.57 (s, 3H), 4.66 (s, 2H), 6.38 (s, 2H), 7.40 (t, J=7.8 Hz, 1H), 7.64 (s, 1H), 8.15 (t, J=7.5 Hz, 1H); ESI-MS (m/z) 739.06 (M–H)$^-$.

Step 3: (4-(2,3-Difluoro-4-(trifluoromethyl)phenyl)-2-((2-(5,7-dimethyl-4,6-dioxo-4,5,6,7-tetrahydroisothiazolo[5,4-d]pyrimidin-3-yl)acetyl)imino)thiazol-3 (2H)-yl)methyl dihydrogen phosphate: The title compound was prepared according to the general procedure as described in method A for the hydrolysis of phosphate esters by hydrolysis of step 2 intermediate (800 mg, 1.08 mmol) in dry dichloromethane (16 ml) using trifluoroacetic acid (250 μl, 3.247 mmol) to yield 460 mg of product as a white solid. Alternatively the title compound was also prepared according to the general procedure as described in method B for the hydrolysis of phosphate esters by hydrolysis of Step 2 intermediate (200 mg) in acetone (16 ml) and water (16 ml) to yield 100 mg of title compound as a white solid. $^1$H NMR (300 MHz, DMSO-d$_6$): δ 3.20 (s, 3H), 3.49 (s, 3H), 4.68 (s, 2H), 6.21 (d, J=6.3 Hz, 2H), 7.70 (t, J=7.2 Hz, 1H), 7.93 (s, 1H), 8.18 (t, J=7.2 Hz, 1H), 10.00-12.00 (m 2H); ESI (m/z): 627.64 (M+H)$^+$.

Example 32

Disodium-(4-(2,3-difluoro-4-(trifluoromethyl)phenyl)-2-((2-(5,7-dimethyl-4,6-dioxo-4,5,6,7-tetrahydroisothiazolo[5,4-d]pyrimidin-3-yl)acetyl)imino)thiazol-3 (2H)-yl)methyl phosphate

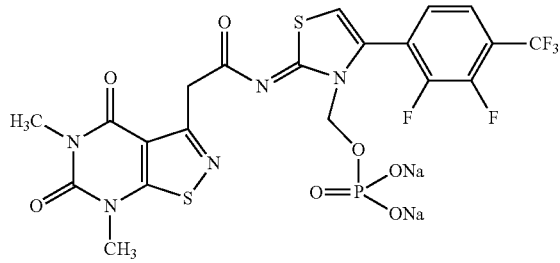

The title compound was prepared according to the general procedure as described in method B for preparation of disodium phosphonate salts by the reaction of Example 31 (100 mg, 0.159 mmol) with sodium carbonate (16.90 mg, 0.159 mmol) in acetonitrile (8 ml) and water (6 ml) to yield 95 mg of product as an off-white solid. $^1$H NMR (300 MHz, $D_2O$) δ 3.23 (br s, 3H), 3.52 (br s, 3H), 4.44-4.50 (m, 2H), 6.06 (br s, 2H), 7.52 (br s, 1H), 7.72 (br s, 1H), 8.07 (br s, 1H). ESI (m/z): 625.78 (M−H)$^-$.

Pharmacological Activity

The illustrative examples of the present invention were screened for TRPA1 activity according to a modified procedure described in (a) Tóth, A. et al. *Life Sciences*, 2003, 73, 487-498. (b) McNamara C, R. et al, *Proc. Natl. Acad. Sci. U.S.A.*, 2007, 104, 13525-13530. The screening of the compounds can be carried out by other methods and procedures known to persons skilled in the art.

Screening for TRPA1 Antagonist Using the $^{45}$Calcium Uptake Assay:

The inhibition of TRPA1 receptor activation was measured as inhibition of allyl isothiocyanate (AITC) induced cellular uptake of radioactive calcium.

Test compounds were dissolved in 100% DMSO to prepare 10 mM stock and then diluted using plain medium with 0.1% BSA and 1.8 mM $CaCl_2$ to get the desired concentration. The final concentration of DMSO in the reaction was 0.5% (v/v). Human TRPA1 expressing CHO cells were grown in F-12 DMEM medium with 10% FBS, 1% penicillin-streptomycin solution, and 400 µg/ml of G-418. Cells were seeded 24 h prior to the assay in 96 well plates so as to get ~50,000 cells per well on the day of experiment. Cells were treated with the test compounds for 10 minutes followed by the addition of AITC at a final concentration of 30 µM and 5 µCi/ml $^{45}Ca^{+2}$ for 3 minutes. Cells were washed and lysed using a buffer containing 1% Triton X-100, 0.1% deoxycholate and 0.1% SDS. Radioactivity in the lysate was measured in a Packard TopCount after addition of liquid scintillant. (Toth et al, *Life Sciences* (2003) 73, 487-498; McNamara C R et al, *Proceedings of the National Academy of Sciences*, (2007) 104, 13525-13530).

Concentration response curves were plotted as a % of maximal response obtained in the absence of test antagonist. $IC_{50}$ values can be calculated from concentration response curve by nonlinear regression analysis using GraphPad PRISM software.

The compounds prepared were tested using the above assay procedure and the results obtained are given in Table 2. Percentage inhibition at concentrations of 1.0 µM and 10.0 µM are given in the table along with $IC_{50}$ (nM) details for selected examples. The $IC_{50}$ (nM) values of the compounds are set forth in Table 1, wherein "A" refers to an $IC_{50}$ value of less than 100 nM, "B" refers to $IC_{50}$ value in range of 100.01 to 500.0 nM and "C" refers to $IC_{50}$ value of greater than 500 nM.

TABLE 2

| Example No. | Percentage inhibition at 1.0 µM | Percentage inhibition at 10.0 µM | Human $IC_{50}$ value (nM) |
|---|---|---|---|
| Example 1 | 68.06 | 90.29 | B |
| Example 2 | 54.82 | 70.18 | C |
| Example 3 | 100.00 | 99.93 | A |
| Example 5 | 98.64 | 99.88 | A |
| Example 6 | 89.77 | 98.60 | B |
| Example 7 | 98.58 | 99.61 | A |
| Example 8 | 96.50 | 98.32 | A |
| Example 9 | 80.07 | 94.79 | B |
| Example 10 | 90.52 | 89.34 | B |
| Example 12 | — | — | B |
| Example 11 | 53.43 | 99.76 | C |
| Example 13 | 75.29 | 99.34 | C |
| Example 14 | — | — | B |
| Example 15 | 81.24 | 98.45 | B |
| Example 16 | 48.18 | 92.73 | C |
| Example 17 | 20.77 | 96.75 | C |
| Example 18 | 30.01 | 88.70 | C |
| Example 19 | 70.27 | 96.70 | B |
| Example 20 | 96.67 | 96.24 | A |
| Example 21 | 93.78 | 99.87 | A |
| Example 22 | 99.15 | 99.58 | B |
| Example 23 | 91.18 | 97.80 | B |
| Example 24 | 98.12 | 99.78 | A |
| Example 25 | 46.47 | 97.77 | C |
| Example 26 | 12.64 | 96.25 | C |
| Example 27 | 93.85 | 99.33 | A |
| Example 28 | 29.48 | 92.44 | C |
| Example 29 | — | — | C |
| Example 31 | 60.05 | 99.17 | C |
| Example 32 | 13.85 | 80.95 | C |

Determination of Solubility by Shake Flask Method

About 1 mg of test substance was taken in test tube and water was added in the increment of 1 ml with shaking after addition of media (water). Solubility was observed visually also. After completion of addition of 10 ml volume of media (water), test tube containing sample solution were put on a mechanical shaker set at 37° C. and 200 rpm for shaking up to 15 minute. After shaking, content of flask was filtered through 0.45µ filter. This filtered solution is analyzed using HPLC method for quantification. A sample solution of 1 mg in 10 ml of DMSO is used as reference standard for quantifying dissolved test substance in media. Solubility is expressed as mcg/ml.

Aqueous solubility of 'P' substituted thiazole compounds and the parent thiazole compounds were determined using the above described procedure and the results are given Table 3.

TABLE 3

Solubility data of 'P' substituted thiazole compounds and parent thiazole compounds.

Solubility in water (µg/ml)

| Example No | ('P' substituted thiazole) | (parent thiazole) |
|---|---|---|
| 10 | >29.0 | <0.2 |
| 13 | >2.5 | <0.2 |
| 14 | >1200 | <0.2 |
| 28 | >30.0 | <0.1 |
| 29 | >110.0 | <0.1 |
| 25 | >10.0 | <1.1 |
| 26 | >75.0 | <1.1 |

Pharmacokinetic (PK) Studies

PK values were obtained in male rats (strain: Sprague Dawley) orally dosed with the compounds of the present invention as suspension. Accurately weighed quantity of compound of present invention (corrected for purity and salt factor) was transferred into a clean and dry mortar. To this mortar was added 2.5 µL/mL Tween 80 and triturated until the compound gets properly wet. To this, 0.5% (w/v) methyl cellulose suspension was added in geometric proportions and triturated thoroughly to form a uniform suspension.

Experimental Procedure

Animals were provided with food and water ad libitum through out the study period. Animals were dosed orally with the compounds using a gavage needle at 10 mL/kg body weight. Blood samples (250 µl approx.) were collected from male Sprague Dawley retro orbital sinus using rat capillary tubes into 0.6 mL eppendorf tubes with tripotassium ethylenediaminetetraacetic acid (K3 EDTA) (25 µL) as anticoagulant. Samples were collected at 0.5, 1.0, 2.0, 4.0, 6.0, 8.0, 12.0 and 24.0 hr post dosing for compounds. Then samples were centrifuged immediately at 1000 g for 10 min. at 4° C. Plasma samples were separated and stored at −70° C. till analysis. Samples were processed and analyzed using LCMS/MS. Pharmacokinetic parameters were calculated using Winonlin software. Table 4 provides the pK values ($C_{max}$, AUC) obtained in these studies.

TABLE 4

Rat PK profile of P' substituted thiazole compounds and parent thiazole compounds:

| | ('P' substituted thiazole) | | (parent thiazole) | |
|---|---|---|---|---|
| Example No. | $C_{max}$ (ng/mL) | $AUC_{0-24}$ (ng h/mL) | $C_{max}$ (ng/mL) | $AUC_{0-24}$ (ng h/mL) |
| 5 | >2500 | >40000 | <1250 | <14000 |
| 7 | >5000 | >70000 | <1250 | <14000 |
| 13 | >500 | >8000 | <1250 | <14000 |
| 14 | >4000 | >50000 | <1250 | <14000 |
| 20 | >4000 | >15000 | <1250 | <13000 |
| 21 | >5000 | >50000 | <1250 | <13000 |
| 23 | >1000 | >8000 | <1250 | <13000 |
| 25 | >2000 | >25000 | <1250 | <13000 |
| 28 | >1500 | >25000 | <1500 | <17000 |
| 29 | >7500 | >100000 | <1500 | <17000 |
| 31 | >7000 | >70000 | <1250 | <12500 |
| 32 | >7500 | >100000 | <1250 | <12500 |

The invention claimed is:

1. A compound selected from
   [2-{[(1,3-Dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methyl-2-methyl propanoate;
   [4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl-2-methylpropanoate;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl 2,2-dimethylpropanoate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl L-prolinate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl L-prolinate hydrochloride;

[2-{[(1,3-Dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methylpiperidine-4-carboxylate;

[2-{[(1,3-Dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methylpiperidine-4-carboxylate hydrochloride;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl piperidine-4-carboxylate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl piperidine-4-carboxylate hydrochloride;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl piperidine-4-carboxylate;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl piperidine-4-carboxylate hydrochloride;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl glycinate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl glycinate hydrochloride;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl L-alaninate;

[4[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl L-alaninate hydrochloride;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl L-valinate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl L-valinate hydrochloride;

[2-{[(1,3-Dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methyl L-isoleucinate;

[2-{[(1,3-Dimethyl-2,4-dioxo-1,2,3,4-tetrahydrothieno[2,3-d]pyrimidin-5-yl)acetyl]imino}-4-[3-fluoro-4-(trifluoromethyl)phenyl]-1,3-thiazol-3(2H)-yl]methyl L-isoleucinate hydrochloride;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl L-isoleucinate;

[4-[2,4-Difluoro-3-(trifluoromethyl)phenyl]-2-{[(1,3-dimethyl-2,4-dioxo-1,2,3,4-tetrahydrothieno[2,3-d]pyrimidin-5-yl)acetyl]imino}-1,3-thiazol-3(2H)-yl]methyl L-isoleucinate hydrochloride;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl glycinate;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl glycinate hydrochloride;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl L-valinate;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl L-valinate hydrochloride;

[4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl L-isoleucinate;

[4[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl L-isoleucinate hydrochloride;

4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl L-phenylalaninate;

4-[3-Chloro-4-(trifluoromethoxy)phenyl]-2-{[(1,3,6-trimethyl-2,4-dioxo-1,2,3,4-tetrahydrofuro[2,3-d]pyrimidin-5-yl)acetyl]imino}-1,3-thiazol-3(2H)-yl]methyl L-phenylalaninate hydrochloride;

or a pharmaceutically acceptable salt thereof.

2. A compound of formula

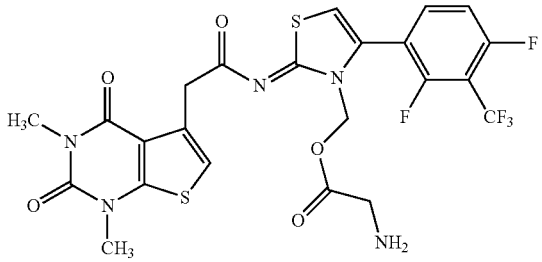 [SMILES: Cn1c(=O)c2c(CC(=O)/N=c3\scc(-c4ccc(F)c(C(F)(F)F)c4F)n3COC(=O)CN)csc2n(C)c1=O]

or a pharmaceutically acceptable salt thereof.

3. A compound of formula

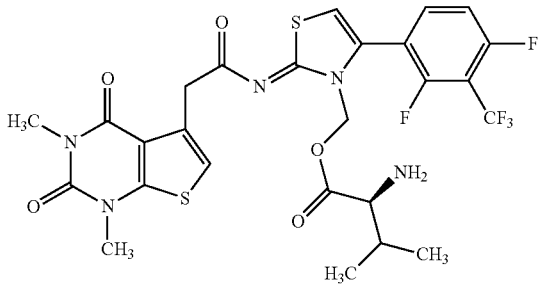 [SMILES: CC(C)[C@H](N)C(=O)OCn1c(-c2ccc(F)c(C(F)(F)F)c2F)cs/c1=N\C(=O)Cc1csc2c1c(=O)n(C)c(=O)n2C]

or a pharmaceutically acceptable salt thereof.

4. A compound of formula
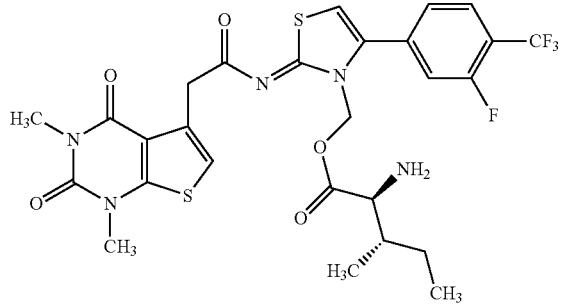 [SMILES: CC[C@H](C)[C@H](N)C(=O)OCn1c(-c2ccc(C(F)(F)F)c(F)c2)cs/c1=N\C(=O)Cc1csc2c1c(=O)n(C)c(=O)n2C]
or a pharmaceutically acceptable salt thereof.
5. A compound of formula
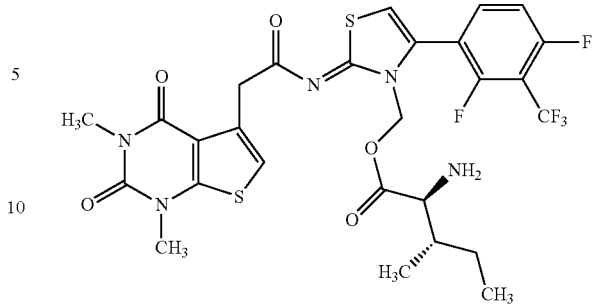
or a pharmaceutically acceptable salt thereof.
6. A pharmaceutical composition comprising one or more compounds of claim 1, and one or more pharmaceutically acceptable excipients, carriers, diluents or mixture thereof.
* * * * *